(12) United States Patent
Irvine et al.

(10) Patent No.: US 9,393,199 B2
(45) Date of Patent: Jul. 19, 2016

(54) METHODS AND COMPOSITIONS FOR LOCALIZED AGENT DELIVERY

(71) Applicant: Massachusetts Institute of Technology, Cambridge, MA (US)

(72) Inventors: Darrell J. Irvine, Arlington, MA (US); Matthias Stephan, Boston, MA (US); Jaehyun Moon, Ann Arbor, MI (US); Anna Bershteyn, Seattle, WA (US)

(73) Assignee: Massachusetts Institute Of Technology, Cambridge, MA (US)

( * ) Notice: Subject to any disclaimer, the term of this patent is extended or adjusted under 35 U.S.C. 154(b) by 204 days.

(21) Appl. No.: 13/910,937

(22) Filed: Jun. 5, 2013

(65) Prior Publication Data
US 2014/0017170 A1  Jan. 16, 2014

Related U.S. Application Data

(63) Continuation of application No. 13/130,845, filed as application No. PCT/US2009/006290 on Nov. 24, 2009.

(60) Provisional application No. 61/200,160, filed on Nov. 24, 2008.

(51) Int. Cl.
| | |
|---|---|
| *A61K 9/127* | (2006.01) |
| *A61K 35/17* | (2015.01) |
| *A61K 38/19* | (2006.01) |
| *A61K 9/51* | (2006.01) |
| *A61K 31/7105* | (2006.01) |
| *A61K 31/711* | (2006.01) |
| *A61K 38/20* | (2006.01) |
| *A61K 45/06* | (2006.01) |
| *A61K 47/48* | (2006.01) |
| *B82Y 5/00* | (2011.01) |
| *C12N 5/00* | (2006.01) |
| *C12N 5/0783* | (2010.01) |
| *C12N 5/0789* | (2010.01) |
| *C12N 15/87* | (2006.01) |
| *A61K 39/00* | (2006.01) |
| *A61K 39/395* | (2006.01) |
| *A61K 47/46* | (2006.01) |
| *A61K 35/12* | (2015.01) |

(52) U.S. Cl.
CPC ............ *A61K 9/127* (2013.01); *A61K 9/5146* (2013.01); *A61K 9/5153* (2013.01); *A61K 31/711* (2013.01); *A61K 31/7105* (2013.01); *A61K 38/2086* (2013.01); *A61K 39/00* (2013.01); *A61K 39/395* (2013.01); *A61K 45/06* (2013.01); *A61K 47/46* (2013.01); *A61K 47/48776* (2013.01); *A61K 47/48815* (2013.01); *A61K 47/48915* (2013.01); *B82Y 5/00* (2013.01); *C12N 5/0006* (2013.01); *C12N 5/0636* (2013.01); *C12N 5/0647* (2013.01); *C12N 15/87* (2013.01); *A61K 2035/124* (2013.01)

(58) Field of Classification Search
CPC ........ A61K 9/127; A61K 35/17; A61K 38/19; C12N 5/0636; C12N 5/0638
USPC .............................................. 424/93.71, 450
See application file for complete search history.

(56) References Cited

U.S. PATENT DOCUMENTS

| | | | |
|---|---|---|---|
| 5,464,629 A | 11/1995 | Monshipouri et al. | |
| 5,753,261 A | 5/1998 | Fernandez et al. | |
| 6,117,982 A | 9/2000 | Chang | |
| 6,120,751 A | 9/2000 | Unger | |
| 6,194,388 B1 | 2/2001 | Krieg et al. | |
| 6,197,298 B1 | 3/2001 | Chang | |
| 6,319,715 B1 | 11/2001 | Luo et al. | |
| 6,544,549 B1 | 4/2003 | Boni et al. | |
| 6,693,086 B1 | 2/2004 | Dow et al. | |
| 7,223,544 B2 | 5/2007 | Luo et al. | |
| 7,402,431 B2 | 7/2008 | Har-Noy | |
| 2001/0038859 A1* | 11/2001 | Maskiewicz et al. | 424/499 |
| 2001/0043929 A1* | 11/2001 | Zalipsky et al. | 424/178.1 |
| 2002/0151004 A1 | 10/2002 | Craig | |
| 2003/0054027 A1 | 3/2003 | Unger | |
| 2003/0235619 A1 | 12/2003 | Allen et al. | |
| 2004/0247624 A1 | 12/2004 | Unger et al. | |
| 2005/0042298 A1 | 2/2005 | Pardridge et al. | |
| 2005/0130180 A1 | 6/2005 | Luo et al. | |
| 2005/0214274 A1* | 9/2005 | Har-Noy | 424/93.71 |
| 2005/0266067 A1 | 12/2005 | Sengupta et al. | |
| 2006/0270030 A1* | 11/2006 | Voigt et al. | 435/325 |
| 2006/0275371 A1 | 12/2006 | Dai et al. | |

(Continued)

FOREIGN PATENT DOCUMENTS

| | | |
|---|---|---|
| WO | WO 2004/032970 A2 | 4/2004 |
| WO | 2007/034479 A2 | 3/2007 |

OTHER PUBLICATIONS

Konigsberg et al, Biochimica et Biophysica Acta 1370:243-251, 1998.*
Beisiegel et al, Nature 341:162-164, 1989.*
Chen et al., Characterization of PLGA micro-spheres for the controlled delivery of IL-1a for tumor immunotherapy. J Controlled Rel. 1997;43:261-72.
Immordino et al., Stealth liposomes: review of the basic science, rationale, and clinical applications, existing and potential. Int J Nanomedicine. 2006;1(3):297-315.
Akagi et al., [Development of vaccine adjuvants using polymeric nanoparticles and their potential applications for anti-HIV vaccine]. Yakugaku Zasshi. Feb. 2007;127(2):307-17.
Akin et al., Bacteria-mediated delivery of nanoparticles and cargo into cells. Nat Nanotechnol. Jul. 2007;2(7):441-9. doi: 10.1038/nnano 2007.149. Epub Jun. 10, 2007.

(Continued)

*Primary Examiner* — Kevin Hill
(74) *Attorney, Agent, or Firm* — Nelson Mullins Riley & Scarborough LLP; Amy E. Mandragouras, Esq.

(57) ABSTRACT

The invention provides compositions and methods for delivering agents to localized regions, tissues, or organs in vivo by conjugating agent-loaded nanoparticles to cells having homing capability. The agents may be therapeutic or diagnostic agents such as cancer chemotherapeutic agents and imaging agents respectively.

66 Claims, 21 Drawing Sheets

(56) References Cited

U.S. PATENT DOCUMENTS

| | | | |
|---|---|---|---|
| 2007/0059318 A1 | 3/2007 | Balu-Iyer et al. | |
| 2007/0148246 A1 | 6/2007 | Luo et al. | |
| 2007/0298093 A1 | 12/2007 | Konur et al. | |
| 2008/0014144 A1* | 1/2008 | Saltzman et al. | 424/9.1 |
| 2008/0267986 A1 | 10/2008 | Pfeifer et al. | |
| 2008/0279836 A1 | 11/2008 | Har-Noy | |
| 2010/0226973 A1 | 9/2010 | Fujii et al. | |
| 2010/0323018 A1 | 12/2010 | Irvine et al. | |
| 2010/0324124 A1 | 12/2010 | Irvine et al. | |
| 2011/0177156 A1 | 7/2011 | Szoka et al. | |
| 2011/0229529 A1 | 9/2011 | Irvine et al. | |
| 2011/0229556 A1 | 9/2011 | Irvine et al. | |
| 2011/0293705 A1 | 12/2011 | Irvine et al. | |
| 2012/0003295 A1 | 1/2012 | Jiang et al. | |
| 2012/0121688 A1 | 5/2012 | Ishii et al. | |
| 2012/0177724 A1 | 7/2012 | Irvine et al. | |

OTHER PUBLICATIONS

Allen et al., Anti-CD19-targeted liposomal doxorubicin improves the therapeutic efficacy in murine B-cell lymphoma and ameliorates the toxicity of liposomes with varying drug release rates. Clin Cancer Res. May 1, 2005;11(9):3567-73.

Allen et al., Drug delivery systems: entering the mainstream. Science. Mar. 19, 2004;303(5665):1818-22.

Alving, Lipopolysaccharide, lipid A, and liposomes containing lipid A as immunologic adjuvants. Immunobiology. Apr. 1993;187(3-5):430-46.

Alving, Liposomes as carriers of antigens and adjuvants. J Immunol Methods. Jun. 24, 1991;140(1):1-13.

Babensee et al., Differential levels of dendritic cell maturation on different biomaterials used in combination products. J Biomed Mater Res A. Sep. 15, 2005;74(4):503-10. Epub Jul. 11, 2005. (Winner of the Young Investigator Award, 30th Ann Mtg Soc Biomater, Memphis, TN, Apr. 27-30, 2005.).

Bal et al., Efficient induction of immune responses through intradermal vaccination with N-trimethyl chitosan containing antigen formulations. J Control Release. Mar. 19, 2010;142(3):374-83. doi: 10.1016/j.jconrel.2009.11.018. Epub Nov. 22, 2009.

Barral et al., B cell receptor-mediated uptake of CD1d-restricted antigen augments antibody responses by recruiting invariant NKT cell help in vivo. Proc Natl Acad Sci U S A. Jun. 17, 2008;105(24):8345-50. doi:10.1073/pnas.0802968105. Epub Jun. 11, 2008.

Bennewitz et al., The effect of the physical form of poly(lactic-co-glycolic acid) carriers on the humoral immune response to co-delivered antigen. Biomaterials. Jun. 2005;26(16):2991-9. Epub Sep. 30, 2004.

Bershteyn et al. Lipid-coated nano-and microparticles for vaccine design. Materials Research Society fall meeting. 2009. 7 pages.

Bershteyn et al., Polymer-supported lipid shells, onions, and flowers. Soft Matter. 2008;4(9):1787-1791.

Bershteyn et al., Robust IgG responses to nanograms of antigen using a biomimetic lipid-coated particle vaccine. J Control Release. Feb. 10, 2012;157(3):354-65. Epub Jul. 24, 2011.

Bershteyn et al., Versatile lipid-based vaccine carriers elicit CTL and antibody responses to surface-conjugated or encapsulated antigen. Keystone Symposium. Poster Presentation. 2010. 1 page.

Berstheyn et al., Versatile lipid-bases vaccine carriers elicit CTL and antibody responses to surface-conjugated or encapsulated antigen. Keystone Symposium. Abstract. 2010. 1 page.

Bhowmick et al., Comparison of liposome based antigen delivery systems for protection against Leishmania donovani. J Controlled Release. Jan. 25, 2010;141(2):199-207. Epub Oct. 7, 2009.

Cashion et al., Biomimetic design and performance of polymerizable lipids. Acc Chem Res. Aug. 18, 2009;42(8):1016-25. Epub May 19, 2009. doi: 10.1021/ar800191s.

Chacón et al., Optimized preparation of poly d,l (lactic-glycolic) microspheres and nanoparticles for oral administration. Int J Pharm. Sep. 6, 1996;141(1-2):81-91. Abstract only.

Chambers et al., Long circulating nanoparticles via adhesion on red blood cells: mechanism and extended circulation. Exp Biol Med (Maywood). Jul. 2007;232(7):958-66.

Chambers et al., Prolonged circulation of large polymeric nanoparticles by non-covalent adsorption on erythrocytes. J Control Release. Nov. 5, 2004;100(1):111-9. Abstract only.

Cole et al., Tumor-targeted, systemic delivery of therapeutic viral vectors using hitchhiking on antigen-specific T cells. Nat Med. Oct. 2005;11(10):1073-81. Epub Sep. 18, 2005. Abstract only.

Collins et al., Processing of exogenous liposome-encapsulated antigens in vivo generates class I MHC-restricted T cell responses. J Immunol. Jun. 1, 1992;148(11):3336-41.

Davis et al., Nanoparticle therapeutics: an emerging treatment modality for cancer. Nat Rev Drug Discov. Sep. 2008;7(9):771-82. Doi: 10.1038/nrd2614. Abstract only.

Demento et al., Inflammasome-activating nanoparticles as modular systems for optimizing vaccine efficacy. Vaccine. May 18, 2009;27(23):3013-21. doi: 10.1016/j.vaccine.2009.03.034. Epub Apr. 3, 2009. Author manuscript available in PMC May 18, 2010 is provided.

Diwan et al., Dose sparing of CpG oligodeoxynucleotide vaccine adjuvants by nanoparticle delivery. Curr Drug Deliv. Oct. 2004;1(4):405-12. Abstract only.

Dou et al., Development of a macrophage-based nanoparticle platform for antiretroviral drug delivery. Blood. Oct. 15, 2006;108(8):2827-35. Epub Jun. 29, 2006. Erratum in: Blood. Mar. 1, 2007;109(5):1816.

Drummond et al., Optimizing liposomes for delivery of chemotherapeutic agents to solid tumors. Pharmacol Rev. Dec. 1999;51(4):691-743.

Dudley et al., Cancer regression and autoimmunity in patients after clonal repopulation with antitumor lymphocytes. Science. Oct. 25, 2002;298(5594):850-4. Epub Sep. 19, 2002. Author manuscript available in PMC Jan. 5, 2007 is provided.

Elamanchili et al., Characterization of poly(D,L-lactic-co-glycolic acid) based nanoparticulate system for enhanced delivery of antigens to dendritic cells. Vaccine. Jun. 23, 2004;22(19):2406-12. Abstract only.

Fifis et al., Size-dependent immunogenicity: therapeutic and protective properties of nano-vaccines against tumors. J Immunol. Sep. 1, 2004;173(5):3148-54.

Fischer et al., Nanotoxicity: the growing need for in vivo study. Curr Opin Biotechnol. Dec. 2007;18(6):565-71. Epub Dec. 21, 2007.

Friede et al., Induction of immune response against a short synthetic peptide antigen coupled to small neutral liposomes containing monophosphoryl lipid A. Mol Immunol. Apr. 1993;30(6):539-47.

Gabizon et al., Prolonged circulation time and enhanced accumulation in malignant exudates of doxorubicin encapsulated in polyethylene-glycol coated liposomes. Cancer Res. Feb. 15, 1994;54(4):987-92.

Garinot et al., PEGylated PLGA-based nanoparticles targeting M cells for oral vaccination. J Control Release. Jul. 31, 2007;120(3):195-204. Epub May 22, 2007.

Green et al., Combinatorial Modification of Degradable Polymers Enables Transfection of Human Cells Comparable to Adenovirus. Advanced Materials. Oct. 2007;19(19):2836-42. Epub Sep. 6, 2007. Abstract only.

Gregoriadis et al., Liposomes as immunological adjuvants and vaccine carriers. J Control Release. Aug. 1996;41(1-2):49-56.

Hamdy et al., Enhanced antigen-specific primary CD4+ and CD8+ responses by codelivery of ovalbumin and toll-like receptor ligand monophosphoryl lipid A in poly(D,L-lactic-co-glycolic acid) nanoparticles. J Biomed Mater Res A. Jun. 1, 2007;81(3):652-62. Epub Dec. 22, 2006.

Heffernan et al., The stimulation of CD8+ T cells by dendritic cells pulsed with polyketal microparticles containing ion-paired protein antigen and poly(inosinic acid)-poly(cytidylic acid). Biomaterials. Feb. 2009;30(5):910-8. doi: 10.1016/j.biomaterials.2008.10.034. Epub Nov. 25, 2008.

Heit et al., Antigen co-encapsulated with adjuvants efficiently drive protective T cell immunity. Eur J Immunol. Aug. 2007;37(8):2063-74.

(56) References Cited

OTHER PUBLICATIONS

Hori et al., Injectable dendritic cell-carrying alginate gels for immunization and immunotherapy. Biomaterials. Sep. 2008;29(27):3671-82. doi: 10.1016/j.biomaterials.2008.05.033. Epub Jun. 20, 2008.
Hotz et al., Vesicle-templated polymer hollow spheres. Langmuir. Mar. 1998;14(5):1031-6. Epub Feb. 3, 1998.
Hu et al., Cytosolic delivery of membrane-impermeable molecules in dendritic cells using pH-responsive core-shell nanoparticles. Nano Lett. Oct. 2007;7(10):3056-64. Epub Sep. 21, 2007. Abstract only.
Irvine, Engineering nanomaterials as vaccine adjuvants and agents for cancer immunotherapy. Seminar at Scripps Res Institute Apr. 28, 2011. 57 slides.
Irvine, Engineering nanoparticle delivery for vaccines and immunotherapy. Nanotechnology in Infectious Disease meeting, Atlanta, GA. 2010. 33 pages.
Jeong et al., Enhanced adjuvantic property of polymerized liposome as compared to a phospholipid liposome. J Biotechnol. Apr. 11, 2002; 94(3):255-263.
Jiang et al., Biodegradable poly(lactic-co-glycolic acid) microparticles for injectable delivery of vaccine antigens. Adv Drug Deliv Rev. Jan. 10, 2005;57(3):391-410.
June, Principles of adoptive T cell cancer therapy. J Clin Invest. May 2007;117(5):1204-12.
Kaiser-Schulz et al., Polylactide-coglycolide microspheres co-encapsulating recombinant tandem prion protein with CpG-oligonucleotide break self-tolerance to prion protein in wild-type mice and induce CD4 and CD8 T cell responses. J Immunol. Sep. 1, 2007;179(5):2797-807.
Kirby et al., Dehydration-rehydration vesicles: a simple method for high yield drug entrapment in liposomes. Nat Biotechnol. Nov. 1984;2(11):979-84.
Kirpotin et al., Antibody targeting of long-circulating lipidic nanoparticles does not increase tumor localization but does increase internalization in animal models. Cancer Res. Jul. 1, 2006;66(13):6732-40.
Kwon et al., In vivo targeting of dendritic cells for activation of cellular immunity using vaccine carriers based on pH-responsive microparticles. Proc Natl Acad Sci U S A. Dec. 20, 2005;102(51):18264-8. Epub Dec. 12, 2005.
Lachman et al., Cytokine-containing liposomes as vaccine adjuvants. Eur Cytokine Netw. Dec. 1996;7(4):693-8.
Lavelle et al., The stability and immunogenicity of a protein antigen encapsulated in biodegradable microparticles based on blends of lactide polymers and polyethylene glycol. Vaccine. Feb. 12, 1999;17(6):512-29.
Lee et al., Multifunctional nanoarchitectures from DNA-based ABC monomers. Nat Nanotechnol. Jul. 2009;4(7):430-6. Epub May 3, 2009. Advanced online publication.
Li et al., PEGylated PLGA nanoparticles as protein carriers: synthesis, preparation and biodistribution in rats. J Control Release. Apr. 2, 2001;71(2):203-11. Abstract only.
Li et al., Purification of melanoma reactive T cell by using a monocyte-based solid phase T-cell selection system for adoptive therapy. J Immunother. Jan. 2008;31(1):81-8. Abstract only.
Lutsiak et al., Analysis of poly(D,L-lactic-co-glycolic acid) nanosphere uptake by human dendritic cells and macrophages in vitro. Pharm Res. Oct. 2002;19(10):1480-7.
Maeda et al., Tumor vascular permeability and the EPR effect in macromolecular therapeutics: a review. J Control Release. Mar. 1, 2000;65(1-2):271-84. Abstract only.
Maloy et al., Induction of mucosal and systemic immune responses by immunization with ovalbumin entrapped in poly(lactide-coglycolide) microparticles. Immunology. Apr. 1994;81(4):661-7.
Martínez Gómez et al., A protective allergy vaccine based on CpG- and protamine-containing PLGA microparticles. Pharm Res. Oct. 2007;24(10):1927-35. Epub May 31, 2007.
Matsumura et al., A new concept for macromolecular therapeutics in cancer chemotherapy: mechanism of tumoritropic accumulation of proteins and the antitumor agent smancs. Cancer Res. Dec. 1986;46(12 Pt 1):6387-92.

McKee et al., How do adjuvants work? Important considerations for new generation adjuvants. Immunity. Nov. 2007;27(5):687-90.
Moghimi et al., Long-circulating and target-specific nanoparticles: theory to practice. Pharmacol Rev. Jun. 2001;53(2):283-318.
Mohammed et al., Lyophilisation and sterilisation of liposomal vaccines to produce stable and sterile products. Methods. Sep. 2006;40(1):30-8.
Moon et al., Engineering nano- and microparticles to tune immunity. Adv Mater. Jul. 24, 2012;24(28):3724-46. doi: 10.1002/adma. 201200446. Epub May 29, 2012. Abstract only.
Moon et al., Enhancing humoral responses to a malaria antigen with nanoparticle vaccines that expand Tfh cells and promote germinal center induction. Proc Natl Acad Sci U S A. Jan. 24, 2012;109(4):1080-5. Epub Jan. 12, 2012.
Moon et al., Interbilayer-crosslinked multilamellar vesicles as synthetic vaccines for potent humoral and cellular immune responses. Nat Mater. Mar. 2011;10(3):243-51. Epub Feb. 20, 2011.
Mundargi et al., Nano/micro technologies for delivering macromolecular therapeutics using poly(D,L-lactide-co-glycolide) and its derivatives. J Control Release. Feb. 11, 2008;125(3):193-209. Epub Oct. 22, 2007.
Murcia et al., Design of quantum dot-conjugated lipids for long-term, high-speed tracking experiments on cell surfaces. J Am Chem Soc. Nov. 12, 2008;130(45):15054-62. Epub Oct. 21, 2008. Author manuscript available in PMC Nov. 12, 2009 is provided.
O'Hagan et al., Induction of potent immune responses by cationic microparticles with adsorbed human immunodeficiency virus DNA vaccines. J Virol. Oct. 2001;75(19):9037-43.
O'Hagan et al., Microparticles as potentially orally active immunological adjuvants. Vaccine. Oct. 1989;7(5):421-4.
O'Hagan et al., Microparticles as vaccine adjuvants and delivery systems. Expert Rev Vaccines. Apr. 2003;2(2):269-83.
O'Hagan et al., Poly(lactide-co-glycolide) microparticles for the development of single-dose controlled-release vaccines. Adv Drug Deliv Rev. Jul. 6, 1998;32(3):225-246.
Owens et al., Opsonization, biodistribution, and pharmacokinetics of polymeric nanoparticles. Int J Pharm. Jan. 3, 2006;307(1):93-102. Epub Nov. 21, 2005. Abstract only.
Park et al., Anti-HER2 immunoliposomes:enhanced efficacy attributable to targeted delivery. Clin Cancer Res. Apr. 2002;8(4):1172-81.
Paulos et al., Toll-like receptors in tumor immunotherapy. Clin Cancer Res. Sep. 15, 2007;13(18 Pt 1):5280-9.
Popescu et al., A novel proteoliposomal vaccine elicits potent anti-tumor immunity in mice. Blood. Jun. 15, 2007;109(12):5407-10. Epub Mar. 9, 2007.
Prokop et al., Hydrogel-based colloidal polymeric system for protein and drug delivery: physical and chemical characterization, permeability control and applications. Filled Elastomers Drug Delivery Systems. Advances in Polymer Science. 2002;160:119-73.
Puri et al., HER2-specific affibody-conjugated thermosensitive liposomes (Affisomes) for improved delivery of anticancer agents. J Liposome Res. 2008;18(4):293-307. Author manuscript available in PMC Jul. 17, 2012 is provided.
Qiao et al., Purging metastases in lymphoid organs using a combination of antigen-nonspecific adoptive T cell therapy, oncolytic virotherapy and immunotherapy. Nat Med. Jan. 2008;14(1):37-44. Epub Dec. 9, 2007. Abstract only.
Reddy et al., Exploiting lymphatic transport and complement activation in nanoparticle vaccines. Nature Biotechnology. Oct. 2007;25(10):1159-64. Epub Sep. 16, 2007.
Reddy et al., In vivo cytotoxic T lymphocyte induction with soluble proteins administered in liposomes. J Immunol. Mar. 1, 1992;148(5):1585-9.
Reed et al., New horizons in adjuvants for vaccine development. Trends Immunol. Jan. 2009;30(1):23-32. doi:10.1016/j.it.2008.09. 006. Epub Dec. 6, 2008.
Rosenberg et al., Adoptive cell transfer: a clinical path to effective cancer immunotherapy. Nat Rev Cancer. Apr. 2008;8(4):299-308. Doi: 10.1038/nrc2355. Author manuscript available in PMC Sep. 25, 2008 is provided.
Rubinstein et al., Converting IL-15 to a superagonist by binding to soluble IL-15R{alpha}. Proc Natl Acad Sci U S A. Jun. 13, 2006;103(24):9166-71. Epub Jun. 6, 2006.

(56) References Cited

OTHER PUBLICATIONS

Sahaf et al., Lymphocyte surface thiol levels. Proc Natl Acad Sci U S A. Apr. 1, 2003;100(7):4001-5. Epub Mar. 17, 2003.
Schlosser et al., TLR ligands and antigen need to be coencapsulated into the same biodegradable microsphere for the generation of potent cytotoxic T lymphocyte responses. Vaccine. Mar. 20, 2008;26(13):1626-37. doi: 10.1016/j.vaccine.2008.01.030. Epub Feb. 6, 2008.
Shi et al., Dendrimer-functionalized shell-crosslinked iron oxide nanoparticles for in-vivo magnetic resonance imaging of tumors. Advanced Materials. May 5, 2008;20(9):1671-8. Abstract only.
Singh et al., Anionic microparticles are a potent delivery system for recombinant antigens from Neisseria meningitidis serotype B. J Pharm Sci. Feb. 2004;93(2):273-82.
Singh et al., Cationic microparticles are an effective delivery system for immune stimulatory cpG DNA. Pharm Res. Oct. 2001;18(10):1476-9.
Singh et al., Cationic microparticles: A potent delivery system for DNA vaccines. Proc Natl Acad Sci U S A. Jan. 18, 2000;97(2):811-6.
Singh et al., Charged polylactide co-glycolide microparticles as antigen delivery systems. Expert Opin Biol Ther. Apr. 2004;4(4):483-91.
Singh et al., Immunogenicity and protection in small-animal models with controlled-release tetanus toxoid microparticles as a single-dose vaccine. Infect Immun. May 1997;65(5):1716-21.
Singh et al., Nanoparticles and microparticles as vaccine-delivery systems. Expert Rev Vaccines. Oct. 2007;6(5):797-808.
Singh et al., Polylactide-co-glycolide microparticles with surface adsorbed antigens as vaccine delivery systems. Curr Drug Deliv. Jan. 2006;3(1):115-20.
Singh et al., Recent advances in vaccine adjuvants. Pharm Res. Jun. 2002;19(6):715-28.
Society for Experimental Biology and Medicine, Nanoparticles hitchhike on red blood cells for drug delivery. RxPG News. Jun. 27, 2007. Last retrieved from http://www.rxpgnews.com/drugdelivery/Nanoparticles-hitchhike-on-red-blood-cells-a-potential-new-method-for-drug-delivery_40324.shtml on Nov. 8, 2012.
Steers et al., Liposome-encapsulated HIV-1 Gag p24 containing lipid A induces effector CD4+ T-cells, memory CD8+ T-cells, and pro-inflammatory cytokines. Vaccine. Nov. 16, 2009;27(49):6939-49. Epub Sep. 11, 2009.
Stephan et al., Enhancing Cell therapies from the Outside In: Cell Surface Engineering Using Synthetic Nanomaterials. Nano Today. Jun. 1, 2001;6(3):309-325. Author manuscript available in PMC Jun. 1, 2012 is provided.
Stephan et al., Synapse-directed delivery of immunomodulators using T-cell-conjugated nanoparticles. Biomaterials. Aug. 2012;33(23):5776-87. doi: 10.1016/j.biomaterials.2012.04.029. Epub May 15, 2012. Abstract only.
Stephan et al., T cell-encoded CD80 and 4-1BBL induce auto- and transcostimulation, resulting in potent tumor rejection. Nat Med. Dec. 2007;13(12):1440-9. Epub Nov. 18, 2007. Abstract only.
Swiston et al., Surface functionalization of living cells with multilayer patches. Nano Lett. Dec. 2008;8(12):4446-53. Epub Ahead of Print Nov. 5, 2008. Abstract only.
Takasaki et al., Micelles as intermediates in the preparation of protein-liposome conjugates. Bioconjug Chem. Mar.-Apr. 2006;17(2):438-50. Epub Jan. 12, 2006.
Tangney et al., The use of Listeria monocytogenes as a DNA delivery vector for cancer gene therapy. Bioeng Bugs. Jul.-Aug. 2010;1(4):284-7. doi: 10.4161/bbug.1.4.11725. Epub Mar. 7, 2010. Abstract only.
Torchilin, Recent advances with liposomes as pharmaceutical carriers. Nat Rev Drug Disc. Feb. 2005;4(2):145-60.
Um et al., Enzyme-catalysed assembly of DNA hydrogel. Nat Mater. Oct. 2006;5(10):797-801. Epub Sep. 24, 2006. Advanced online publication.
Vangala et al., Comparison of vesicle based antigen delivery systems for delivery of hepatitis B surface antigen. J Controlled Release. May 14, 2007;119(1):102-10. Epub Jan. 27, 2007.
Vasir et al., Biodegradable nanoparticles for cytosolic delivery of therapeutics. Adv Drug Deliv Rev. Aug. 10, 2007;59(8):718-28. Epub Jun. 26, 2007. Author manuscript available in PMC Aug. 10, 2008 is provided.
Verma et al., Surface-structure-regulated cell-membrane penetration by monolayer-protected nanoparticles. Nat Mater. Jul. 2008;7(7):588-95. Epub May 25, 2008.
Von Maltzahn et al., In vivo tumor cell targeting with "click" nanoparticles. Bioconjug Chem. Aug. 2008;19(8):1570-8. doi: 10.1021/bc800077y. Epub Jul. 9, 2008. Author manuscript available in PMC Aug. 1, 2009 is provided.
Vonarbourg et al., Parameters influencing the stealthiness of colloidal drug delivery systems. Biomaterials. Aug. 2006;27(24):4356-73. Epub May 2, 2006. Abstract only.
Wakita et al., An indispensable role of type-1 IFNs for inducing CTL-mediated complete eradication of established tumor tissue by CpG-liposome co-encapsulated with model tumor antigen. Int Immunol. Mar. 2006;18(3):425-34. Advance access publication Jan. 13, 2006.
Wilson-Welder et al., Vaccine adjuvants: current challenges and future approaches. J Pharm Sci. Apr. 2009;98(4):1278-316. doi: 10.1002/jps.21523.
Yee et al., Adoptive T cell therapy using antigen-specific CD8+ T cell clones for the treatment of patients with metastatic melanoma: in vivo persistence, migration, and antitumor effect of transferred T cells. Proc Natl Acad Sci U S A. Dec. 10, 2002;99(25):16168-73. Epub Nov. 11, 2002.
Zauner et al., In vitro uptake of polystyrene microspheres: effect of particle size, cell line and cell density. J Control Release. Mar. 12, 2001;71(1):39-51.
Zhang et al., Folate-decorated poly(lactide-co-glycolide)-vitamin E TPGS nanoparticles for targeted drug delivery. Biomaterials. Apr. 2007;28(10):1889-99. Epub Jan. 2, 2007. Abstract only.
Zhao et al., Directed cell migration via chemoattractants released from degradable microspheres. Biomaterials. Aug. 2005;26(24):5048-63. Abstract only.
Zhu et al., Stabilization of proteins encapsulated in injectable poly (lactide- co-glycolide). Nat Biotechnol. Jan. 2008;18(1):52-7.
Chacon et al., "Optimized preparation of poly d,l (lactic-glycolic) microspheres and nanoparticles for oral administration," Int J Pharm., vol. 141(1-2), pp. 81-91 (1996).
Chambers et al., "Prolonged circulation of large polymeric nanoparticles by non-covalent adsorption on erythrocytes," J Control Release, vol. 100(1), pp. 111-119 (2004).
Cole et al., "Tumor-targeted, systemic delivery of therapeutic viral vectors using hitchhiking on antigen-specific T mils," Nat Med., vol. 11, pp. 1073-1081 (2005).
Davis et al., "Nanoparticle therapeutics: an emerging treatment modality for cancer," Nat Rev Drug Discov., vol. 7, pp. 771-782. (2008).
Dinauer, N. et al., "Selective targeting of antibody-conjugated nanoparticles to leukemic cells and primary T-lymphocytes," Biomaterials., vol. 26, pp. 5898-5906 (2005).
Diwan et al., "Dose sparing of CpG oligodeoxynucleotide vaccine adjuvants by nanoparticle delivery," Curr Drug Deliv. vol. 1(4), pp. 405-412 (2004).
Elamanchili et al., "Characterization of poly(D,L-lactic-co-glycolic acid) based nanoparticulate system for enhanced delivery of antigens to dendritic cells.," Vaccine, vol. 22, pp. 2406-2412 (2004).
Gao et al., "Lectin-conjugated PEG-PLA nanoparticles: preparation and brain delivery after intranasal administration," Biomaterials. vol. 27, pp. 3482-3490 (2006).
Green et al., "Combinatorial Modification of Degradable Polymers Enables Transfection of Human Cells Comparable to Adenovirus," Advanced Materials, vol. 19(19), pp. 2836-2842 (2007).
Li et al., "PEGylated PLGA nanoparticles as protein carriers: synthesis, preparation and biodistribution in rats," J Control Release, vol. 71(2) p. 203-211 (2001).
Li et al., "Purification of melanoma reactive T cell by using a monocyte-based solid phase T-cell selection system for adoptive therapy, " J Immunother vol. 31(1), pp. 81-88 (2008).
Lodish et al., "Molecular Cell Biology," Chemical Foundations, Chapter 2, Fifth Eds., pp. 29-57 (2004).

(56) References Cited

OTHER PUBLICATIONS

Lu et al., Cationic albumin-conjugated pegylated nanoparticles as novel drug carrier for brain delivery. J Control Release, vol. 107(3), pp. 428-448 (2005).

Maeda et al., "Tumor vascular permeability and the EPR effect in macromolecular therapeutics: a review," J Control Release, vol. 65(1-2), pp. 271-284 (2000).

Moon et al., "Engineering nano-and microparticles to tune immunity," Adv Materiels, vol. 24(28), pp. 3724-3746. (2012).

Owens, III. et al., "Opsonization, biodistribution, and pharmacokinetics of polymeric nanoparticles.," Int J Pharm. vol. 307(1), pp. 93-102 (2006).

Qiad et al., "Purging metastases in lymphoid organs using a combination of antigen-nonspecific adoptive T cell therapy, oncolytic virotherapy and immunotherapy.," Nat Med. vol. 14(1), pp. 37-44 (2008).

Shi et al., "Dendrimer-functionalized shell-crosslinked iron oxide nanoparticles for in-vivo magnetic resonance imaging of tumors," Advanced Materials, vol. 20(9), 1671-1678 (2008).

Stephan et al., "Synapse-directed delivery of immunomodulators using T -cell-conjugated nanoparticles," Biomaterials, vol. 33(23), pp. 5776-5787 (2012).

Stephan et al., "T cell-encoded CD80 and 4-1BBL induce auto-and transcostimulation, resulting in potent tumor rejection," Nat Med. , vol. 13(12), pp. 1440-1449 (2007).

Swiston et al., "Surface functionalization of living cells with multilayer patches," Nano Letters, vol. 8(12), pp. 4446-4453 (2008).

Tangney M et al., "The use of Listeria monocytogenes as a DNA delivery vector for cancer gene therapy," Bioeng Bugs., vol. 1 (4) , pp. 284-287 (2010).

Vonarbourg et al., "Parameters influencing the stealthiness of colloidal drug delivery systems," Biomaterials., vol. 27(24), pp. 4356-4373 (2006).

Zhang et al., "Folate-decorated poly(lactide-co-glycolide)-vitamin E TPGS nanoparticles for targeted drug delivery," Biomaterials., vol. 28, pp. 1889-1899 (2007).

Zhao et al., "Directed cell migration via chemoattractants released from degradable microspheres," Biomaterials. vol. 26(24), pp. 5048-5063 (2005).

Bottini, Luminescent Silica Nanobeads: Characterization and Evaluation as Efficient Cytoplasmatic Transporters for T-Lymphocytes, JACS, vol. 129(25) pp. 7814-7823 (2007).

Hu et al., "Cytosolic delivery of membrane-impermeable molecules in dendritic cells using pH-responsive core-shell nanoparticles," Nano Lett. vol. 7(10), pp. 3056-3064 (2007).

U.S. Appl. No. 13/130,845, filed Aug. 16, 2011, Darrell J. Irvine.
U.S. Appl. No. 13/130,845, Oct. 16, 2015, K. Hill.
U.S. Appl. No. 13/130,845, Jan. 13, 2015, K. Hill.
U.S. Appl. No. 13/130,845, Sep. 11, 2013, K. Hill.
U.S. Appl. No. 13/130,845, Feb. 26, 2013, K. Hill.
U.S. Appl. No. 13/130,845, Oct. 22, 2012 K. Hill.

* cited by examiner

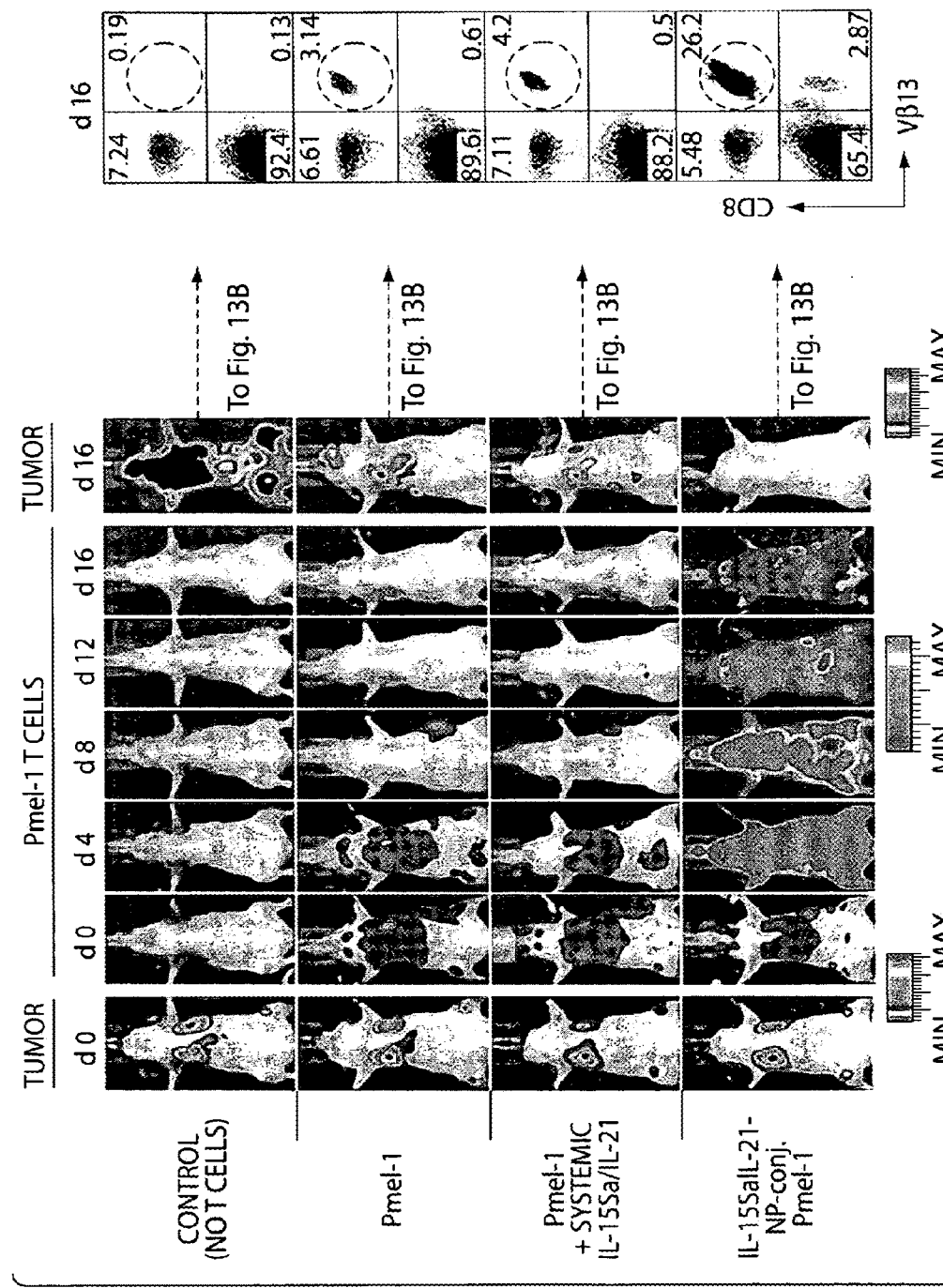

METHODS AND COMPOSITIONS FOR LOCALIZED AGENT DELIVERY

RELATED APPLICATIONS

This application is a continuation of U.S. application Ser. No. 13/130,845, filed on Aug. 16, 2011, which is a national stage filing under 35 U.S.C. §371 of International Application No. PCT/US2009/006290, filed Nov. 24, 2009, which was published under PCT Article 21(2) in English, and which claims priority under 35 U.S.C. §119 from U.S. provisional application Ser. No. 61/200,160, filed Nov. 24, 2008, the entire contents of each of which are incorporated by reference herein.

FEDERALLY SPONSORED RESEARCH

This invention was made with Government support under Grant Nos. R01 EB007280 and R01 CA140476 awarded by the National Institutes of Health. The government has certain rights in this invention.

BACKGROUND OF THE INVENTION

1. Field of Invention

The invention relates to the delivery of agents to localized regions, tissues, or cells in the body using nanoparticles and cells.

2. Discussion of Related Art

Cell-based immunotherapies are in active development for treatment of cancer, and adoptive cell therapy (ACT) of cancer with ex vivo activated/expanded T cells is one of the more promising treatments currently being tested in patients. (Rosenberg et al., Nat Rev Cancer 8(4): 299, 2008; Dudley et al., Science 298(5594): 850, 2002; June et al., J Clin Invest 117(5): 1204, 2007; Stephan et al., Nat Med 13(12): 1440, 2007; Yee et al., Proc Natl Acad Sci USA 99(25): 16168, 2002.) These approaches involve the use of autologous T cells taken from patients that are activated/expanded ex vivo and then reinfused to combat tumors such as metastatic tumors. Strategies that enhance the persistence, in vivo expansion, and effector functions of ACT T cells should increase the frequency of objective responses. (Rosenberg S A et al., Nat Rev Cancer 8(4): 299, 2008; June C H et al., J Clin Invest 117(5): 1204, 2007.) One way to enhance the function of ACT T cells is via genetic engineering of the cells themselves, introducing chimeric receptors or costimulatory molecules. (Stephan et al., Nat Med 13(12): 1440, 2007; Morgan et al., Science 314(5796): 126, 2006; Gade et al., Cancer Res 65(19): 9080, 2005.)

Interleukin-family cytokines such as IL-2 and IL-15 have been of particular interest for promoting the effector functions and proliferation of anti-tumor T cells. IL-2 and IL-15 share some of their properties in triggering T cell proliferation/effector function, and systemic IL-2 has been used to support adoptively transferred T cells in both mouse models and human clinical trials of cancer treatment.

However, IL-2 expands regulatory T cells that can suppress anti-tumor immune responses, is known to promote activation-induced cell death (AICD) in T cells, and has substantial toxicity when administered systemically. (Antony et al., J Immunol 176(9): 5255, 2006; Fontenot et al., Nat Immunol 6(11): 1142, 2005; Oh et al., Proc Natl Acad Sci USA 100(6): 3392, 2003; Waldmann, Nat Rev Immunol 6(8): 595, 2006; Waldmann et al., Immunity 14(2): 105, 2001.)

In contrast, IL-15 supports T cell proliferation and effector functions without promoting AICD. (Oh et al., Proc Natl Acad Sci USA 100(6): 3392, 2003; Waldmann, Nat Rev Immunol 6(8): 595, 2006; Waldmann et al., Immunity 14(2): 105, 2001.) IL-15 signals through a heterotrimeric receptor composed of a dedicated $\alpha$ chain, a shared IL-2/IL-15R$\beta$ chain, and the common $\gamma$ chain used by several interleukins. In an unusual mode of function, physiologic IL-15 signaling has been shown to be largely mediated by presentation of the cytokine in trans: cells bearing the IL-15R$\alpha$ chain bind the cytokine with high affinity and present the cytokine to T cells bearing the $\beta$ and $\gamma$ chains. As a result, IL-15R$\alpha$ chain expression by the responding cells is unnecessary in this context. (Dubois et al., Immunity 17(5): 537, 2002; Stoklasek et al., J Immunol 177(9): 6072, 2006.)

Recently, strategies for re-activating or maintaining the activity of anti-tumor T cells ex vivo have been described, based on striking effects of IL-15 on anti-tumor CD8$^+$ T cells. IL-15 has been used interchangeably with IL-2 as a systemic therapy in preclinical models of ACT, promoting destruction of large melanoma tumors when combined with booster vaccination to drive expansion of adoptively transferred tumor-specific T cells. (Klebanoff et al., Proc Natl Acad Sci USA 101(7): 1969, 2004.) Teague et al. showed that culture of non-functional T cells recovered from tumors with IL-15 overcomes the anergic state observed in these cells, allowing them to proliferate and regain potent effector functions. (Teague et al., Nat Med 12(3): 335, 2006.) However, systemically injected IL-15 has been shown to have a short half life of only ~1 hr, and has limited potency in vivo, triggering limited proliferation of T cells compared to responses observed during prolonged in vitro culture. (Stoklasek et al., J Immunol 177(9): 6072, 2006.) This result may reflect the protein's short half-life and/or limiting availability of free IL-15R$\alpha$ chains for binding and trans-presentation of the cytokine.

As a strategy to overcome this limitation, several independent studies recently demonstrated that pre-complexation of IL-15 with soluble recombinant IL-15R$\alpha$ enhances the systemic potency of IL-15 by ~50-fold, and also raises the half life of the cytokine in serum following systemic injection to ~20 hrs. (Stoklasek et al., J Immunol 177(9): 6072, 2006; Dubois et al., J Immunol 180(4): 2099, 2008; Rubinstein et. al. Proc Natl Acad Sci USA 103(24): 9166, 2006.) Following on these findings, long-term daily injections of IL-15/IL-15R$\alpha$ complexes have been shown to prolong the survival of mice in a spontaneous mouse model of pancreatic cancer, by reactivating the cytolytic activity of tumor-resident T cells. (Epardaud et al., Cancer Res 68(8): 2972, 2008.) Notably, in these in vivo studies of IL-15/IL-15R$\alpha$ superagonist (IL-15 SA) complex treatment, not only memory CD8$^+$ T cells but also naïve CD8$^+$ T cells were shown to proliferate, upregulate activation markers, and gain effector functions in response to IL-15/IL-15R$\alpha$ complex, leading to gross splenomegaly in mice receiving prolonged IL-15 SA treatment. (Stoklasek et al., J Immunol 177(9): 6072, 2006; Dubois et al., J Immunol 180(4): 2099, 2008; Rubinstein et. al. Proc Natl Acad Sci USA 103(24): 9166, 2006.) This non-specific polyclonal T cell activation elicited by systemic IL-15 SA may raise the risk of autoimmunity if treatment is prolonged.

Cytokines such as IL-2 and IL-15 act primarily by acting on T cells, NK cells, and NK T cells to promote immune responses. Complementary to these signals, Toll-like receptor (TLR) ligands have been used in cancer immunotherapy by driving activation of dendritic cells (DCs) and other APCs both in tumor-draining lymph nodes and directly in the tumor microenvironment. TLRs are pattern recognition receptors that have evolved to detect a variety of molecules associated with pathogens ranging from bacteria to fungi to viruses. TLR ligands trigger DCs to upregulate costimulatory receptors and secrete pro-immunity cytokines such as IL-12. (Beutler, Nature 430(6996): 257, 2004; Iwasaki et al., Nat Immunol 5(10): 987, 2004; Pulendran, Immunol Rev 199: 227, 2004; Reis e Sousa, Semin Immunol 16(1): 27, 2004.) Thus, these factors are under study as potential adjuvants for vaccines. TLR signaling is implicated in breaking regulatory T cell-mediated tolerance (Pasare et al., Science 299(5609): 1033, 2003), and sustained delivery of TLR ligands to lymph nodes has been shown to break tolerance of tumor self-antigen specific T cells in an adoptive therapy model. (Yang et al., Nat Immunol 5(5): 508, 2004.) Regression of large established melanoma tumors achieved by adoptive therapy augmented with a viral vector vaccination boost may function in part through the sustained TLR engagement provided by viral vector immunization. (Yang et al., Nat Immunol 5(5): 508, 2004; Overwijk et al., J Exp Med 198(4): 569, 2003.) In other studies, repeated injections of TLR ligands directly into tumors has been used to promote the activation of tumor-resident APCs and drive effective local immune responses. (Heckelsmiller et al., Eur J Immunol 32(11): 3235, 2002; Furumoto et al., J Clin Invest 113(5): 774, 2004; Currie et al., J Immunol 180(3): 1535, 2008.) TLR ligands in combination with IL-10 blockade have also been shown to convert dysfunctional DCs in the tumor microenvironment into a pro-immunity functional state. (Vicari et al., J Exp Med 196(4): 541, 2002.)

Drug-loaded synthetic biodegradable polymer nanoparticles are becoming of more interest for treating a variety of diseases, as they may offer a low-cost, readily manufacturable means to achieve sustained drug delivery at selected target tissue sites and concentrate drugs where they are needed in the body. (Davis et al., Nat Rev Drug Discov 7(9): 771, 2008.) In the delivery of protein therapeutics, synthetic drug delivery particles (particles with sizes in the 50-500 nm range, typically) may be able to achieve results comparable to other means of delivery such as viral vectors (Green et al., Advanced Materials 19(19): 2836, 2007) without the associated side effects of such biological vectors, such as anti-vector immune responses or dangers of viral integration. (Donsante et al., Science 317(5837): 477, 2007; Kresge, IAVI Rep 9(4): 18, 2005; Mingozzi et al., Nat Med 13(4): 419, 2007; Watkins et al., Nat Med 14(6): 617, 2008.) In cancer therapy, passive accumulation of nanoparticles at tumor sites via the enhanced permeation and retention effect (Maeda et al., J Control Release 65(1-2): 271, 2000; Matsumura et al., Cancer Res 46(12 Pt 1): 6387, 1986) (referring to the combined effects of leaky tumor vasculature and poor lymphatic drainage often observed at solid tumor sites) has been exploited for therapeutic and imaging agent delivery to solid tumors. (Davis et al., Nat Rev Drug Discov 7(9): 771, 2008; Shi et al., Advanced Materials 20(9): 1671, 2008; von Maltzahn et al., Bioconjugate Chemistry 19(8): 1570, 2008; Drummond et al., Pharmacol Rev 51(4): 691, 1999; Kirpotin et al., Cancer Res 66(13): 6732, 2006; Park et al., Clin Cancer Res 8(4): 1172, 2002.)

However, treatment of metastatic disease via systemic injection of nanoparticle drug carriers is limited by the rapid clearance of typical nanoparticles. Thus, the half-life of systemically injected nanoparticles or liposomes is typically a few hours or less and accumulation of particles at tumor sites is often only a very small fraction (~1%) of the total injected dose. (Owens, Int J Pharm 307(1): 93, 2006; Vonarbourg et al., Biomaterials 27(24): 4356, 2006; Moghimi et al., Pharmacol Rev 53(2): 283, 2001.) Attachment of poly(ethylene glycol) (PEG) to the surface of liposomes or nanoparticles to create so-called 'stealth' carriers can increase the circulation time of particles up to ~24-48 hrs (Owens, Int J Pharm 307(1): 93, 2006; Vonarbourg et al., Biomaterials 27(24): 4356, 2006; Moghimi et al., Pharmacol Rev 53(2): 283, 2001), but by far the greatest majority of injected dose (often >80%) is still scavenged by the spleen and liver, even when targeting antibodies are employed. (Kirpotin et al., Cancer Res 66(13): 6732, 2006.) Thus, a substantial quantity of drug cargo is degraded without effect or worse, may elicit liver toxicity.

SUMMARY OF THE INVENTION

The invention relates to the use of nanoparticles conjugated to cell carriers to deliver agents in a controlled and localized manner. The invention is based in part on the unexpected finding that certain reactive groups exist at sufficient levels on the surface of certain unmodified cell types that facilitate conjugation to nanoparticles having complementary reactive groups. The invention is further based in part on the unexpected finding that nanoparticles can be maintained on the surface of certain cells without internalization of the nanoparticles, which would interfere with the controlled release of the agents comprised within the nanoparticles. T cells are an example of cells that fail to endocytose nanoparticles in the ~150 nm size range covalently conjugated to its surface even after many days or through several rounds of cell division. The result is that T cells could maintain nanoparticles and release agents in their local environment for prolonged periods. Other cells which have been found to be particularly suited to conjugation to nanoparticles via their cell surface chemistry are B cells and hematopoietic progenitor cells. The cell carriers may be eukaryotic (e.g., mammalian cells) or prokaryotic (e.g., bacterial cells), and they may be naturally occurring or engineered (or modified). If the carrier cells are bacterial or other prokaryotic cells, they may be attenuated in order to reduce or eliminate the risk of infection to the recipient.

Thus, in one aspect the invention provides a method for delivering an agent comprising administering to a subject a nucleated cell bound to a nanoparticle that comprises an agent, wherein the cell does not internalize the nanoparticle, and wherein the agent is released from the nanoparticle in vivo.

Various embodiments apply equally to the preceding aspect of the invention as well as other aspects recited below, and for the sake of brevity these will be recited only once. However it is to be understood that combinations of these aspects and embodiments are contemplated by the invention.

Thus, in some embodiments, the cell is a T cell. In some embodiments, the cell is a B cell, an NK cell, or an NKT cell. In other embodiments, the cell is a hematopoietic progenitor including without limitation a pluripotent stem cell (i.e., a long-term reconstituting cell), a multipotent progenitor cell (e.g., a CFU-S or a CFC-GEMM), a unipotential progenitor cell (e.g., a BFU-E). An example of a murine hematopoietic progenitor is a cell lacking lineage marker cell surface expression, and having Sca-1 and/or c-kit cell surface expression, as described herein.

In some embodiments, the subject has a tumor. In related embodiments, the cell is a tumor-reactive T cell. In other related embodiments, the cell homes to the tumor or to the tissue in which the tumor exists (e.g., lymphoid tissue).

In some embodiments, the subject has an autoimmune disease. In some embodiments, the subject has an infection.

In some embodiments, the subject is in need of hematopoietic reconstitution as a result of, for example, myeloablative chemotherapy and/or radiation.

In some embodiments, the cell is a gut-specific T cell. In some embodiments, the cell is a skin-specific T cell.

In some embodiments, the cell is autologous to the subject. In some embodiments, the cell is activated prior to administration to the subject. In some embodiments, the cell is genetically engineered. In other embodiments, the cell is naturally occurring.

In some embodiments, the cell is a eukaryotic cell such as a mammalian cell. In important embodiments, the mammalian cell is a human cell. In other embodiments, the cell is a prokaryotic cell such as a bacterial cell. The bacterial cell may be a *Salmonella* bacterial cell. In related embodiments, the prokaryotic cell, such as a bacterial cell, may be attenuated so as to prevent an infection in the subject.

In some embodiments, the nanoparticle is 20-500 nm in diameter, or 100-300 nm in diameter. In some embodiments, the nanoparticle is about 150 nm in diameter, or about 200 nm in diameter, or 250 nm in diameter.

In some embodiments, the nanoparticle comprises maleimide reactive groups on its surface. In some embodiments, the nanoparticle comprises a lipid coating.

In some embodiments, the nanoparticle is a DNA nanoparticle (also referred to herein as a DNA-gel nanoparticle) comprising a crosslinked DNA core and optionally a lipid coating.

In some embodiments, the agent is an imaging agent. In some embodiments, the agent is an immunostimulatory agent. In some embodiments, the agent is a cytokine. In some embodiments, the cytokine is IL-15/IL-15Rα. In some embodiments, the agent is an antigen. In some embodiments, the agent is an adjuvant. In some embodiments, the adjuvant is a TLR ligand. The TLR ligand may function to stimulate antigen-specific immune responses (typically in the presence of exogenous or endogenous antigens) and/or antigen-non-specific immune responses. Thus, the TLR ligand may be used in the presence or absence of an antigen. In some embodiments, the agent is an antibody or an antibody fragment. In some embodiments, the agent is a drug. In some embodiments, the agent is a chemical compound. In some embodiments, the agent is a nucleic acid. In some embodiments, the nucleic acid is an siRNA.

In some important embodiments, the agents are anti-cancer agents including anti-cancer antibodies, cancer antigens, anti-cancer chemotherapeutic agents, and the like.

In various embodiments, the agents may be used at doses that are below doses required to achieve the same effects in vivo following systemic administration. In some instances, the doses are at least 2 times less, at least 5 times less, at least 10 times less, at least 20 times less, at least 50 times less, or at least 100 times less than the required systemic dose.

In some embodiments, the cell is covalently bound to a plurality of nanoparticles. In some embodiments, the plurality of nanoparticles comprise an identical agent. In some embodiments, the plurality of nanoparticles comprise different agents. In some embodiments, the plurality of nanoparticles is 50-10,000, or 100-10,000. In some embodiments, the plurality of nanoparticles is about 50, or about 100, or about 150, or about 200, or about 250, or about 500.

In some embodiments, the method further comprises binding the nanoparticle to the cell. In some embodiments, the method further comprises providing the cell bound to the nanoparticle.

In some embodiments, the cell is covalently bound to the nanoparticle.

In some embodiments, the agent acts in an autocrine manner (i.e., it acts upon the cell carrier itself). In some embodiments, the agent acts in a paracrine manner (i.e., it acts upon cells other than the cell carrier). In still other embodiments, the agent acts in both an autocrine and a paracrine manner.

In another aspect, the invention provides a method for delivering an agent comprising administering to a subject a liposome covalently bound to a nanoparticle that comprises an agent, wherein the agent is released from the nanoparticle in vivo.

In another aspect, the invention provides a method for delivering an agent to a tumor comprising administering to a subject having a tumor a tumor-reactive T cell covalently bound to a nanoparticle that comprises an agent, wherein the agent is released from the nanoparticle in vivo. The tumor may be a lymphoma, and the agent may be an anti-lymphoma agent (i.e., an agent having therapeutic effect on lymphoma). An example of such an agent is an antibody such as rituximab.

In another aspect, the invention provides a method for delivering an agent to a tumor comprising administering to a subject having a tumor a tumor-reactive T cell covalently bound to a maleimide-coated nanoparticle that comprises an agent, wherein the agent is released from the nanoparticle in vivo. In some embodiments, the agent is an anti-cancer agent. In some embodiments, the agent is an adjuvant. In some embodiments, the agent is an antigen. In some embodiments, the antigen is a tumor antigen.

In another aspect, the invention provides a method for delivering an agent comprising administering to a subject a cell covalently bound to a nanoparticle that comprises an agent, wherein the cell does not internalize the nanoparticle, and wherein the agent is released from the nanoparticle in vivo.

In another aspect, the invention provides a method for locally delivering an agent within a subject comprising administering to a subject having a tissue homing cell bound to a biodegradable nanoparticle that comprises an agent, wherein the agent is released from the biodegradable nanoparticle in vivo. In some embodiments, the tissue homing cell is a T cell. In some embodiments, the T cell is a gut-homing T cell. In some embodiments, the T cell is a skin-homing T cell. In some embodiments, the biodegradable nanoparticle is covalently bound to the tissue homing cell.

In another aspect, the invention provides a method for delivering an agent to a lymphoma within a subject comprising administering to a subject having a lymphoma a B or T cell (e.g., a central memory T cell) bound to a nanoparticle or a liposome that comprises an agent, wherein the agent is released from the nanoparticle in vivo and the nanoparticle is not internalized into the cell. The agent may be an antibody, such as an anti-CD20 antibody, or it may be a chemotherapy, such as fludaribine. Other agents having therapeutic effect on lymphoma may be used in place of or in addition to anti-CD20 antibody or fludaribine.

In another aspect, the invention provides a biodegradable nanoparticle comprising maleimide groups on its exterior surface.

In some embodiments, the nanoparticle further comprises a lipid bilayer surface. In some embodiments, the nanoparticle comprises a poly(lactide-co-glycolide) (PLGA) core. In some embodiments, the nanoparticle further comprises an agent. In some embodiments, the agent is an immunostimulatory agent. In some embodiments, the agent is an antigen. In some embodiments, the agent is an antibody. In some embodiments, the agent is an adjuvant. In some embodiments, the adjuvant is a TLR ligand. In some embodiments, the TLR ligand is an immunostimulatory agent in the presence or absence of antigen. In some embodiments, the agent is a nucleic acid. In some embodiments, the nucleic acid is an siRNA. In some embodiments, the agent is an anti-cancer agent. In some embodiments, the agent is a cytokine. In some embodiments, the agent is an interleukin.

In some embodiments, the nanoparticle further comprises a plurality of agents. In some embodiments, the plurality of agents comprises an antigen and an adjuvant. In some embodiments, the plurality of agents comprises an adjuvant and an anti-cancer agent. In still other embodiments, the plurality of agents comprises an immunostimulatory agent and an anti-cancer agent.

In some embodiments, the nanoparticle is 50-500 nanometers in diameter, or 100-300 nanometers in diameter. In some embodiments, the nanoparticle is about 50 nanometers in diameter, or about 100 nanometers in diameter, or about 150 nanometers in diameter, or about 200 nanometers in diameter, or about 250 nanometers in diameter. In some embodiments, the nanoparticle is in a lyophilized form.

In another aspect, the invention provides a composition comprising an isolated T cell comprising a biodegradable nanoparticle at its cell surface, wherein the nanoparticle comprises an agent. In some embodiments, the biodegradable nanoparticle is covalently conjugated to the surface of the T cell.

In another aspect, the invention provides a composition comprising an isolated hematopoietic progenitor cell comprising a biodegradable nanoparticle at its cell surface, wherein the nanoparticle comprises an agent. In some embodiments, the biodegradable nanoparticle is covalently conjugated to the surface of the hematopoietic progenitor cell. The agent may be an agent that stimulates the proliferation of hematopoietic progenitor cells, and optionally their self-renewal or their differentiation towards one or more hematopoietic lineages. A non-limiting example of such an agent is a GSK3beta inhibitor.

These and other aspects and embodiments will be described in greater detail herein.

Each of the limitations of the invention can encompass various embodiments of the invention. It is therefore anticipated that each of the limitations of the invention involving any one element or combinations of elements can be included in each aspect of the invention. This invention is not limited in its application to the details of construction and/or the arrangement of components set forth in the following description or illustrated in the drawings. The invention is capable of other embodiments and of being practiced or of being carried out in various ways.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIGS. 13A-D. Pmel-1 T cells conjugated with IL-15Sa/IL-21-releasing nanoparticles robustly proliferate in vivo and eradicate established B16 melanomas. (A) Dual in vivo bioluminescence imaging of Gaussia luciferase-expressing B16F10 lung melanomas and CBR-luciferase-expressing Pmel-1 T cells in sublethally irradiated C57Bl/6 mice. Lung tumors established by tail vein injection of B16F10 cells were treated after 6 days by i.v. infusion of $10 \times 10^6$ $V\beta13^+$ $CD8^+$ Pmel-1 T cells. One group of mice received Pmel-1 T cells conjugated with 100 DNA-gel nanoparticles/cell carrying a total dose of 5 µg IL-15Sa/IL-21 (4.03 µg IL-15Sa+0.93 µg IL-21), control groups received unmodified Pmel-1 cells and a single systemic injection of the same doses of IL-15Sa/IL-21 or Pmel-1 cells alone. (B) Frequencies of $V\beta13^+$ $CD8^+$ Pmel-1 T cells recovered from pooled lymph nodes of representative animals 16 days after T cell transfer. (C) CBR-luc signal intensities from sequential bioluminescence imaging every 2 days after T cell transfer. Every line represents one animal with each dot showing the whole animal photon count. (D) Survival of animals following T cell therapy illustrated by Kaplan-Meier curves. Shown are 6 mice/treatment group pooled from 3 independent experiments.

DETAILED DESCRIPTION OF THE INVENTION

The invention contemplates combined cell- and nanoparticle-mediated delivery of agents including drugs. This delivery strategy involves the conjugation of nanoparticles that comprise one or more agents to a cell that can home to a region, tissue or organ in vivo, thereby resulting in localized and controlled delivery of agents in vivo. This approach offers significant advantages over the prior art approaches of administering agents alone or in non-cell bound delivery vehicles such as nanoparticles. The former approaches suffer from systemic toxicity problems. The latter approaches suffer from rapid clearance of nanoparticles via the reticuloendothelial system including macrophages and Kupffer cells of the spleen and liver (as shown in the Examples), and limitations in biodistribution based on size-mediated exclusion/inclusion from tissues. The clearance mechanisms prevent prolonged release and thus sustained presence of the agent of interest in vivo. Moreover clearance is potentially associated with toxicity in the liver due to the accumulation of nanoparticles at that site, also as shown in the Examples.

The invention therefore exploits the use of nanoparticles and cells in the localized delivery of agents. The cells may function simply as carriers that home to localized regions, tissues or organs within the body and thereby deliver the agent more specifically within the body (i.e., in a paracrine manner), although in more preferred embodiments they also contribute functionally at the ultimate target site and may be acted upon by the agent they are carrying (i.e., in an autocrine manner). In either event, the cells are referred to herein as carrier cells to be distinguished from cells at target sites in vivo.

Figure 1A:
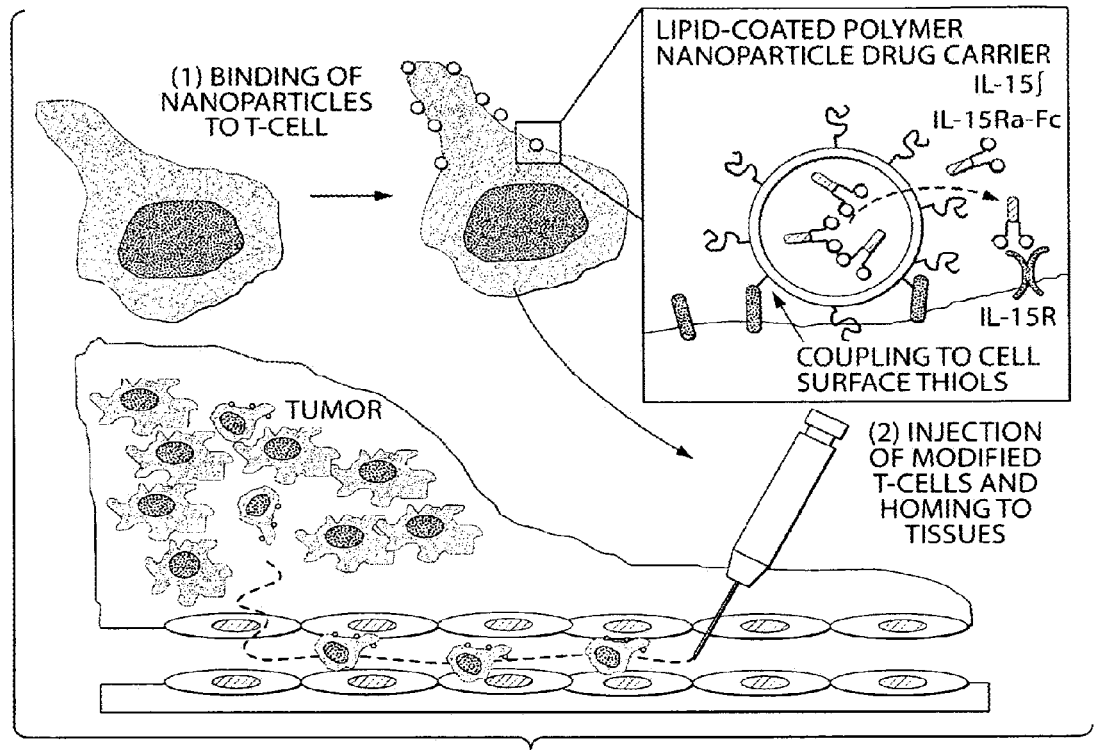
FIG. 1A. Nanoparticle-functionalized T cells for ACT.

In one exemplary embodiment, the invention provides a delivery method based on conjugation of nanoparticles to tumor-reactive T cells, such as those used in adoptive cell therapy (ACT). A functionalized biodegradable polymer nanoparticle, liposome, or polymer vesicle may be loaded with one or more agents which are released in vivo as the nanoparticle degrades in response to its environment (typically an aqueous environment). This is shown schematically in FIG. 1A. This approach offers several potential advantages over systemic drug therapy including the uniform exposure of ACT T cells to the released drugs, focused drug action on the ACT T cells and other T cells at the target site, reduced amounts of drugs administered to a subject as a result of a biodistribution that follows the homing pattern of the T cells, reduced exposure of non-target sites to the drug and thus reduced probability of non-target toxicity, and extended and sustained release of drug over the span of several days.

In a further exemplary embodiment, T cells are conjugated to biodegradable nanoparticles that comprise immune stimulating agents such as cytokines, antigens, antibodies, adjuvants or other activation agents that function to stimulate or enhance immune responses at the target site, maintain activation of the carrier ACT T cells, and/or cause cell death directly or indirectly at the target site. Exemplary agents are provided herein and include but are not limited to IL-15/IL-15Rα complexes (referred to herein as an IL-15 superagonist, described by Rubenstein et al., PNAS 103(24):9166-9171, 2006, the teachings of which relating to IL-15 SA are incorporated herein by reference) and TLR ligand adjuvants such as MPLA and imiquimod. Such nanoparticles may contain other agents such as anti-cancer agents, or they may be used with other nanoparticles that contain such agents. TLR ligands may act as immunostimulating agents independent of an antigen effect, in some instances. In still other instances, the agents may be immunomodulatory or even immunoinhibitory, if it is desired to control or reduce an immune reaction in vivo, such as occurs in autoimmune disorders as an example.

In some instances, the invention contemplates but is not limited to enhancement (whether additive or super-additive) of the therapeutic benefit that is provided by standard adoptive cell therapy which involves transfer of cells that are not conjugated to nanoparticles. This enhancement may be measured by reduction in tumor load (or volume) in the case of a subject having a tumor, or reduction in infectious agent load (for example in a bodily fluid) or reduction in size, depth or volume of an infectious lesion in the case of a subject having an infection.

Figure 1B:
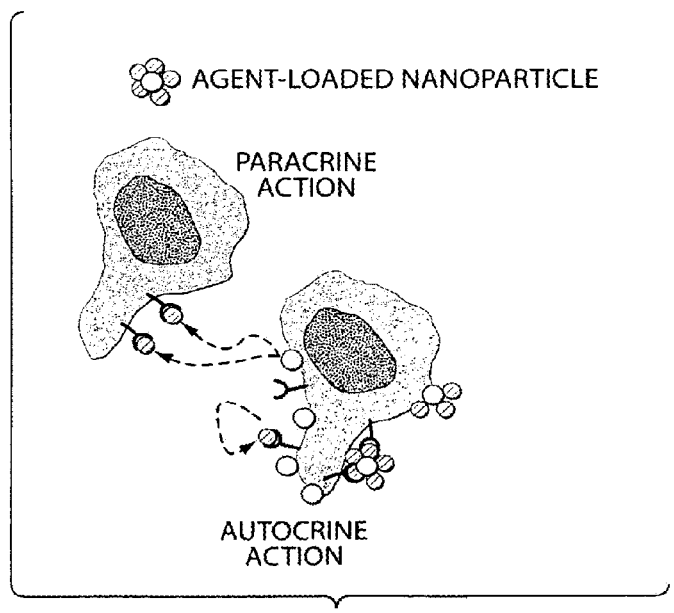
FIG. 1B. Examples of modes of action for nanoparticles bound to cells, including an autocrine mode of action in which the nanoparticles (and their agent payload) act on the carrier cell and a paracrine mode of action in which the nanoparticles (and their agent payloads) act on cells in the environment.

It is to be understood that the agents carried by the nanoparticles may function on cells or tissue at the target site (i.e., a paracrine manner) and/or on the carrier cells themselves (i.e., an autocrine manner), as depicted in FIG. 1B. Thus for example where the cell is a T cell (or other cell with homing capability), the agent may be one that stimulates the carrier cell and optionally cells of the same type at the target site (e.g., other tumor-reactive T cells). In other embodiments, the agents comprised within the nanoparticles are intended to act on cells other than the carrier cell. Examples include anti-cancer agents which act upon tumor cells and generally will have no effect on T cells or other carrier cell types.

Targeting primarily the carrier cells, particularly carrier T cells, serves to maintain their proliferation and effector functions while limiting nonspecific activation of bystander T cells. It has been reported that cytokines released in an autocrine manner may be nearly quantitatively recaptured by the secreting cell, due to the local high concentration of cytokine and its corresponding upon release from the cell. (Monine et al., Biophys J 88(4): 2384, 2005; Lauffenburger et al., Proc Natl Acad Sci USA 95(26): 15368, 1998; Joslin et al., J Cell Sci 120(Pt 20): 3688, 2007.) Cytokines such as IL-15 superagonist are therefore expected to be more potent when released from nanoparticles conjugated to carrier cells than when administered systemically in an unconjugated form.

An example of a paracrine method involves the delivery of adjuvant(s) to a target site alone or together with antigen(s). Exemplary adjuvants are provided herein, and these include TLR ligands such as MPLA and imiquimod. These agents can act on dendritic cells and other antigen presenting cells present at a target site (e.g., a tumor site or a site of infection or at a secondary lymphoid organ or tissue including but not limited to spleen and lymph nodes). The cell-mediated delivery methods of the invention will both increase the local concentration of agents at the relevant target sites and limit the overall systemic exposure that occurs when the same agents are injected in an unconjugated form.

Thus, as another example of paracrine-acting agent(s), in instances where the target site is a tumor, the nanoparticles may comprise an anti-cancer agent and/or an adjuvant. Once delivered to the target tumor site, via tumor-reactive T cells, the anti-cancer agent is gradually released resulting in the death of tumor cells whether by necrosis or apoptosis. Such cell death is usually accompanied by fragmentation and release of cellular components including antigens specific to the tumor cells. The gradual release of adjuvant from nanoparticles delivered to the target site will enhance the body's antigen-specific immune response to the released cancer antigens. The presence of activated tumor-reactive T cells will serve to localize and enhance the immune response as well. Tumor-reactive T cells have been described previously and include without limitation melanoma reactive T cells (e.g., Melan A specific T cells described by Li et al., J Immunother. 31(1):81-8, 2008, the teachings of which relating to melanoma-specific T cells are incorporated herein by reference).

Other tumor targets include without limitation lymphomas. In these instances, B cells and/or T cells such as central memory T cells may be conjugated to nanoparticles comprising anti-lymphoma agents. Such agents are known in the art and include without limitation anti-CD20 antibodies, such as rituximab. As shown in the Examples, B cells and central memory T cells are able to home nanoparticles into lymphoid organs, in particular the spleen and lymph nodes, and reduce the amount of nanoparticles that would otherwise home and/or deposit in liver and bone. The use of lymphocytes as carrier cells is advantageous because the cells are easily obtained from peripheral blood of a subject and they can naturally home (or be manipulated ex vivo to home) to certain tissues (e.g., lymphoid tissues) or tumors. The invention contemplates that other blood diseases including without limitation leukemia may also be treated in a like manner.

The foregoing embodiments are intended for illustration and are not to be construed to limit the invention simply to tumor-specific ACT. Instead, the invention contemplates various other applications where localized delivery of one or more agents and optionally particular cells would be beneficial. As an example, the invention contemplates delivery of imaging agents to various distinct regions, tissues and/or organs. As another example, T cells may be conjugated to nanoparticles carrying any variety and/or combination of agents and can be targeted to any number of sites in vivo. In this embodiment, T cells can be exploited for their demonstrated tropism to different tissues. Examples include naïve T cells that can carry agent-loaded nanoparticles to lymphoid organs and spleen (e.g., for vaccination), gut-homing T cells that can carry agent-loaded nanoparticles to the gut (e.g., for treatment of cancer or autoimmune disorders), skin-homing T cells that can deliver agent-loaded nanoparticles to the skin layers (e.g., for treatment of cutaneous lesions or autoimmune disease), etc. These tissue sites can be targeted simply by isolating T cells with the appropriate homing receptors from blood. It is to be understood that the methods provided herein may be used to stimulate (or enhance) immune responses (e.g., against tumors or infections) or suppress immune responses (e.g., by promoting tolerance to allergens or transplanted tissues).

As a further exemplary embodiment of the invention, hematopoietic progenitor cells may be loaded with nanoparticles that stimulate proliferation and, in some instances, self-renewal. The Examples demonstrate the ability to conjugate nanoparticles comprising the glycogen synthase kinase 3 beta (GSK3-beta) inhibitor TWS119 to lineage-negative, Sca-1-positive, c-kit-positive, and the delivery of such cells to a subject. Biodistribution of the administered cells to the femur, humerus, sternum and spleen of recipients was observed, as was a normal differentiative potential of such cells several months post-transplant.

The methods described herein may be combined with other therapeutic or diagnostic strategies or methods including without limitation surgery, radiation and/or chemotherapy including immunotherapy.

It has been found, surprisingly, that the method is straightforward to implement and thus could be easily incorporated into any clinical process. The method requires simple mixing of the functionalized and agent-loaded nanoparticles with the cells of interest, as detailed in the Examples. Nanoparticles can be prepared and stored in a convenient format prior to use (e.g., lyophilized powder). Nanoparticles are then reconstituted in a suitable carrier and incubated with the cell population for a brief period of time. Incubation times may range from 1-5 minutes, 1-10 minutes, 5-10 minutes, 5-15 minutes, 5-20 minutes, 5-30 minutes, or 5-60 minutes. The mixture is then washed, in some instances incubated with a blocking agent to quench the reactive groups on the nanoparticle and optionally on the cell, washed again, and then formulated for administration. Administration typically will occur via through parental routes, most preferably intravenous injection.

Carrier Cells

The carrier cells are the cells to which the nanoparticles are conjugated and which when administered in vivo preferably home to target site(s). Suitable target cells are chosen based on their homing potential, their cell surface phenotype (for conjugation to the nanoparticles), and their ability to carry but not significantly endocytose the nanoparticles. In some embodiments described herein, T cells are suitable carrier cells. The T cells may be CD4+ or CD8+ T cells. Other suitable cells include B cells, NK cells, NK T cells, and hematopoietic progenitor cells including without limitation murine lineage-negative, Sca-1-positive and c-kit-positive cells and their human counterparts. B cells for example can be used to carry antigen-loaded nanoparticles into lymphoid organs to promote antibody responses or to regulate allergic reactions. Macrophages and dendritic cells typically are not suitable carriers for nanoparticles because of their internalizing/phagocytosing capabilities. Substantial levels of free thiol (—SH) groups exist on the surfaces of T cells, B cells and hematopoietic progenitor cells (data not shown), thereby facilitating conjugation of nanoparticles to such cells.

Carrier cells preferably also are able to extravasate from the blood vessels (particularly when administered by intravenous injection) and thereby enter target tissues or organs. Red blood cells typically are not able to exit the blood stream. Accordingly, one important class of carrier cells is nucleated cells. This class by definition excludes red blood cells.

Some embodiments of the invention refer to isolated carrier cells. Isolated carrier cells are cells that have been separated from the environment in which they naturally occur (i.e., they are not present in vivo). T cells in vitro are an example of an isolated cell.

The carrier cells preferably are autologous to the subject being treated, however some embodiments of the invention contemplate non-autologous (yet preferably MHC matched cells).

The carrier cells preferably have half-lifes in vivo, following administration (or re-infusion, in some instances) of at least 48 hours, more preferably at least, at least 3 days, at least 4 days, at least 5 days, at least 6 days, at least 7 days, or more.

The cells may be genetically engineered to express one or more factors including without limitation costimulatory molecules or receptors including chimeric receptors. In other embodiments, the cells are not genetically engineered. In some such embodiments, the carrier cells are isolated and naturally occurring (i.e., they have not been genetically or otherwise engineered).

Depending on their nature and function, the cells may be manipulated prior to conjugation with the nanoparticles. The cells however need not be surface-modified in order to facilitate conjugation of the nanoparticles. The invention in some of its embodiments instead takes advantage of reactive groups that normally exist on the cell surface without having to incorporate reactive groups or other entities onto the cell surface. As a result, such cells do not require the presence of exogenous entities such as antibodies or antibody fragments, among others, on their surface in order to conjugate to nanoparticles.

Such manipulation may also involve activation of the cells, as is routinely performed for T cells. The cells may be expanded and/or activated (or stimulated, as the terms are used interchangeably herein) in vitro prior to mixing with the nanoparticles (or liposomes). Expansion and activation protocols will vary depending on the cell type but can include incubation with one or more cytokines, incubation with one or more cell types, incubation with one or more antigens, etc. If the carrier cell is a T cell, then activation may be performed by incubating the cells with IL-2, IL-15, IL-15 superagonist, costimulatory molecules such as B7, B7.2, CD40, antibodies to various T cell surface molecules including antibodies to cell surface receptors, anti-CD3 antibodies, anti-CD28 antibodies, anti-CTLA-4 antibodies, anti-CD40L antibodies, and the like. In some embodiments, the cells and more particularly the T cells are not coated with exogenous antibodies on their cell surface (i.e., the cells have not been contacted with antibodies or antibody fragments in vitro prior to administration).

Expansion may be measured by proliferation assays involving incorporation of radiolabeled nucleotides such as tritiated thymidine. Activation may be measured by production of cytokines such as IL-2, gamma-IFN, IL-1, IL-4, IL-6, and TNF, among others. Other ways of measuring expansion and activation are known in the art.

Carrier cells may be selected prior to administration to a subject in order to enrich and thus administer higher numbers of such cells in smaller volumes and/or to remove other, potentially unwanted, cells from the administered composition. Selection may involve positive or negative selection, including for example column or plate based enrichment protocols that are known in the art.

T and B cells may be harvested from the peripheral blood of a subject.

Hematopoietic progenitor cells may be obtained from a number of sources including but not limited to cord blood, bone marrow, mobilized peripheral blood, and in some instances differentiated embryonic stem cells.

Hematopoietic progenitor cells have been characterized in the art. Such cells in the human generally have minimally a CD34+ phenotype, although they may also be CD59+, Thy1/CD90+, CD38$^{lo/neg}$, CD33−, and/or c-kit/CD117+. They also are characterized as not expressing lineage specific markers. They can be harvested from bone marrow, cord blood or peripheral blood using affinity columns, magnetic beads, fluorescence activated cell sorting (FACS), some combination thereof, and the like. These cells have the ability to repopulate one or more hematopoietic lineages upon transplantation. Preferably, these cells repopulate more than one lineage, and even more preferably, all lineages. Repopulation or population of lineages as used herein refers to the differentiation of the stem cell into one or more lineages such that progeny of the stem cell contribute to the make up of that lineage in the subject. It does not however require that the entire lineage compartment derive from the transplanted cells, however in some instances this may occur.

Isolated stem cells may be obtained by fractionating a heterogenous cell population according to one or more markers, including by not limited to cell surface markers.

The carrier cells may be eukaryotic cells, such as mammalian cells (e.g., human cells). Alternatively, they may be non-mammalian cells. In still other embodiments, the carrier cells may be prokaryotic cells (e.g., bacterial cells). Several bacterial cell types are of particular interest. For example, attenuated *salmonella typhimurium* is under study as a candidate vector for oral vaccine delivery (Xiang et al., *Immunol Rev* 222:117, 2008; and Iweala et al., *J Immunol* 183(4):2252, 2009) and engineered *E. coli* bacteria have been shown to be capable of specific homing to poorly oxygenated tumors (Cheong et al., *Science* 314(5803):1308, 2006). Bacteria offer new modes of administration and tissue site targeting possibilities, such as oral administration and the ability to target therapeutics to the gut and gut-associated lymphoid tissues. Such microbial vectors may offer advantages relative to autologous host cells in terms of creating off-the-shelf ready-to-use cell-nanoparticles systems. Particles conjugation to microbes can be achieved using the same suite of chemical strategies described for mammalian cells. In some instances, temporary removal of flagellar coats of microbes (e.g., via simple mechanical shearing as described by Rosu et al., *J Bacteriol* 188(14):5196, 2006) can be used to achieve optimal conjugation of particles to microbe cell bodies. The ability to enhance the activity of these cells by conjugating drug-loaded nanoparticles or microparticles to them for co-transport to their target tissue sites can be used to alter their therapeutic efficacy or alter the biodistribution of the synthetic particles as described herein with other cell carriers. The ability of synthetic drug particles to be loaded with small-molecule therapeutics makes this approach complementary to genetic engineering of the microbe.

Nanoparticles

As used herein, nanoparticles are solid colloidal particles used to deliver agent. Nanoparticles are not liposomes, as used herein. The nanoparticles are not viruses or particles thereof. The nanoparticles are also to be distinguished from films or other structurally layered polymers matrices, since the nanoparticles are comprised of one or more solidified polymer(s) that is arranged in a random manner. The nanoparticles are preferably biodegradable and thus typically are not magnetic. Biodegradable nanoparticles may be synthesized using methods known in the art including without limitation solvent evaporation, hot melt microencapsulation, solvent removal, and spray drying. Exemplary methods for synthesizing nanoparticles are described herein in the Examples as well as by Bershteyn et al., Soft Matter 4:1787-1787, 2008 and in US 2008/0014144 A1, the specific teachings of which relating to nanoparticle synthesis are incorporated herein by reference.

In some embodiments, the nanoparticles are comprised of a nucleic acid internal core. Such "DNA nanoparticles" (or DNA-gel nanoparticles) are described in greater detail in published U.S. application no. US 20070148246. It is to be understood that the nucleic acid core of such particles may act as a scaffold for the agents being delivered in vivo and/or it may act as the agent itself. An exemplary protocol for synthesizing DNA nanoparticles is provided in the Examples.

The nanoparticles release their agent "payload" over a number of days as a function of their degradation profile in vivo. As discussed herein, the nanoparticles are biodegradable in nature and thus they gradually degrade in an aqueous environment such as occurs in vivo. If the agents are dispersed throughout the nanoparticles then their release will occur as the outermost layers of the nanoparticle degrade or as the pores within the nanoparticle enlarge. Release kinetic studies have been performed and they demonstrate that protein and small-molecule drugs can be released from such nanoparticles over time-courses ranging from 1 day to at least 2 weeks. The nanoparticles are preferably not engulfed by either their carrier cells or other cells at the target site. They function rather by gradually releasing their payload into the environment of the target site(s).

The nanoparticles' diameter ranges from 1-1000 nanometers (nm). In some embodiments, their diameter ranges in size from 20-750 nm, or from 20-500 nm, or from 20-250 nm. In some embodiments, their diameter ranges in size from 50-750 nm, or from 50-500 nm, or from 50-250 nm, or from about 100-300 nm. In some embodiments, their diameter is about 100, about 150, about 200 nm, about 250 nm, or about 300 nm. As used in the context of nanoparticle diameters, the term "about" means +/−5% of the absolute value stated. Thus, it is to be understood that although these particles are referred to herein as nanoparticles, the invention intends to embrace microparticles as well.

As discussed herein, the nanoparticles may be synthesized to comprise one or more reactive groups on their exterior surface for reaction with reactive groups on cell carriers (e.g., leukocytes). These nanoparticle reactive groups include without limitation thiol-reactive maleimide head groups, haloacetyl (e.g., iodoacetyl) groups, imidoester groups, N-hydroxysuccinimide esters, pyridyl disulfide groups, and the like. These reactive groups react with groups on the carrier cell surface and thus the nanoparticles are bound to the cell surface. It will be understood that when surface modified in this manner, the nanoparticles are intended for use with specific carrier cells having "complementary" reactive groups (i.e., reactive groups that react with those of the nanoparticles). In some embodiments, the nanoparticles will not integrate into the lipid bilayer that comprises the cell surface. Typically, the nanoparticles will not be phagocytosed (or internalized) by the carrier cells.

In some embodiments the nanoparticles do not comprise antibodies or antibody fragments on their surface, while in other embodiments they do. In some embodiments the nanoparticles do not comprise antibodies or antibody fragments that are specific to T cell surface moieties (or exogenous moieties coated onto a T cell surface such other antibodies or antibody fragments), while in other embodiments they do. Thus, in some embodiments the nanoparticles themselves do not stimulate carrier cell activation simply by binding to the carrier cell. In other embodiments however the nanoparticles do stimulate carrier cell activation by binding to the carrier cell (e.g., binding of the nanoparticle results in crosslinking of cell surface moieties and this activates the carrier cell).

The nanoparticles may be covalently conjugated (or attached or bound, as the terms are used interchangeably herein), or they may be non-covalently conjugated to the carrier cells. Covalent conjugation typically provides a more stable (and thus longer) association between the nanoparticles and the carrier cells. Covalent conjugation in some embodiments also can provide stability and thus more sustained localized delivery of agents in vivo. Non-covalent conjugation includes without limitation absorption onto the cell surface and/or lipid bilayer of the cell membrane.

In some instances, covalent attachment can be achieved in a two-step process in which carrier cells are first incubated with maleimide-bearing nanoparticles to allow conjugation to the cell surface, followed by in situ PEGylation with thiol-terminated poly(ethylene glycol) (PEG) to cap remaining maleimide groups of the particles and avoid particle-mediated crosslinking of cells. With this approach, substantial numbers of nanoparticles with diameters in the 100-300 nm range have been conjugated to cell types used commonly in cell therapy, including CD8$^+$ T lymphocytes and lineage$^-$Sca-1$^+$c-kit$^+$ murine progenitor cells (data not shown). This strategy allows particles ranging from simple liposomes (e.g., with an aqueous drug-loaded core) to more complex lipid-coated polymer or DNA-based nanoparticles to be stably attached to live cells. Importantly, the linkage chemistry is benign and non-toxic as evidenced in part by the conjugation of up to 139 (±29) ~200 nm-diameter lipid-coated nanoparticles to the surface of cells without any deleterious effect (data not shown).

Although liposomes and lipid-coated polymer particles are able to spontaneously adsorb to cell surfaces, in some instances covalent conjugation is preferred due to the increased stability it achieves.

Nanoparticles bound to carrier cells, such as lymphocytes or hematopoietic progenitor cells, remain localized at the cell surface as revealed by optical sectioning with confocal microscopy, scanning electron microscopy and by flow cytometry internalization assays, even following extended in vitro stimulation (data not shown). Phagocytic cells, such as immature dendritic cells, are able to efficiently internalize maleimide-functionalized nanoparticles after a short incubation data not shown), and thus they are not suitable as carrier cells.

Exemplary synthetic polymers which can be used to form the biodegradable nanoparticles include without limitation aliphatic polyesters, poly(lactic acid) (PLA), poly(glycolic acid) (PGA), co-polymers of lactic acid and glycolic acid (PLGA), polycarprolactone (PCL), polyanhydrides, poly(ortho)esters, polyurethanes, poly(butyric acid), poly(valeric acid), and poly(lactide-co-caprolactone), and natural polymers such as alginate and other polysaccharides including dextran and cellulose, collagen, chemical derivatives thereof, including substitutions, additions of chemical groups such as for example alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

The nanoparticles also preferably comprise a lipid bilayer on their outermost surface. This bilayer may be comprised of one or more lipids of the same or different type. Examples include without limitation phospholipids such as phosphocholines and phosphoinositols. Specific examples include without limitation DMPC, DOPC, DSPC, and various other lipids such as those recited below for liposomes.

Liposomes

The invention also contemplates the use of liposomes in place of nanoparticles in the various embodiments described herein. Liposomes are small closed vesicles comprising at least one lipid bilayer and an internal aqueous compartment. As used herein, liposomes are not nanoparticles. Liposomes may be anionic, neutral or cationic. They may be unilamellar or multilamellar. Liposome may comprise without limitation unilamellar vesicle lipids, multilamellar vesicle lipids and extruded lipids including DOTMA, DOTAP, DOTIM, DDAB, alone or together with cholesterol to yield DOTMA and cholesterol, DOTAP and cholesterol, DOTIM and cholesterol, and DDAB and cholesterol. Methods for preparation of multilamellar vesicle lipids are known in the art (see for example U.S. Pat. No. 6,693,086, the teachings of which relating to multilamellar vesicle lipid preparation are incorporated herein by reference). Extruded lipids are prepared in a similar manner but are then extruded through filters of decreasing size, as described in Templeton et al., Nature Biotech, 15:647-652, 1997, the teachings of which relating to extruded lipid preparation are incorporated herein by reference.

Liposomes may be surface modified during or after synthesis to include reactive groups complementary to the reactive groups on the carrier cells. Such reactive groups include without limitation maleimide groups. As an example, liposomes may be synthesized to include maleimide conjugated phospholipids such as without limitation DSPE-MaL-PEG2000.

An exemplary synthesis protocol for liposomes is provided in the Examples.

Agents

The invention contemplates the delivery of agents to localized regions, tissues or cells in vivo. As used herein, an agent is any atom or molecule or compound that can be used to provide benefit to a subject (including without limitation prophylactic or therapeutic benefit) or that can be used for diagnosis and/or detection (for example, imaging) in vivo.

Any agent may be delivered using the methods of the invention provided that it can be loaded into the nanoparticles provided herein. For example, the agent must be able to withstand the nanoparticle synthesis and optionally storage process. The nanoparticles may be synthesized and stored in, for example, a lyophilized form. The agents, if incorporated into the nanoparticles during synthesis, should be stable during such storage procedures and times.

The agent may be without limitation a protein, a polypeptide, a peptide, a nucleic acid, a virus-like particle, a steroid, a proteoglycan, a lipid, a carbohydrate, and analogs, derivatives, mixtures, fusions, combinations or conjugates thereof. The agent may be a prodrug that is metabolized and thus converted in vivo to its active (and/or stable) form.

The agents may be naturally occurring or non-naturally occurring. Naturally occurring agents include those capable of being synthesized by the subjects to whom the nanoparticles are administered. Non-naturally occurring are those that do not exist in nature normally, whether produced by plant, animal, microbe or other living organism.

One class of agents is peptide-based agents such as (single or multi-chain) proteins and peptides. Examples include antibodies, single chain antibodies, antibody fragments, enzymes, co-factors, receptors, ligands, transcription factors and other regulatory factors, some antigens (as discussed below), cytokines, chemokines, and the like. These peptide-based agents may or may not be naturally occurring but they are capable of being synthesized within the subject, for example, through the use of genetically engineered cells.

Another class of agents that can be delivered in a localized manner using the nanoparticles of the invention includes those agents that are not peptide-based and which could not be synthesized by the transferred cells. Examples include chemical compounds that are non-naturally occurring, or chemical compounds that are not naturally synthesized by mammalian (and in particular human) cells.

A variety of agents that are currently used for therapeutic or diagnostic purposes can be delivered according to the invention and these include without limitation imaging agents, immunomodulatory agents such as immunostimulatory agents and immunoinhibitory agents, antigens, adjuvants, cytokines, chemokines, anti-cancer agents, anti-infective agents, nucleic acids, antibodies or fragments thereof, fusion proteins such as cytokine-antibody fusion proteins, Fc-fusion proteins, and the like.

Imaging Agents. As used herein, an imaging agent is an agent that emits signal directly or indirectly thereby allowing its detection in vivo. Imaging agents such as contrast agents and radioactive agents that can be detected using medical imaging techniques such as nuclear medicine scans and magnetic resonance imaging (MRI). Imaging agents for magnetic resonance imaging (MRI) include Gd(DOTA), iron oxide or gold nanoparticles; imaging agents for nuclear medicine include $^{201}$Tl, gamma-emitting radionuclide 99 mTc; imaging agents for positron-emission tomography (PET) include positron-emitting isotopes, (18)F-fluorodeoxyglucose ((18)FDG), (18)F-fluoride, copper-64, gadoamide, and radioisotopes of Pb(II) such as 203 Pb, and 11In; imaging agents for in vivo fluorescence imaging such as fluorescent dyes or dye-conjugated nanoparticles. In other embodiments, the agent to be delivered is conjugated, or fused to, or mixed or combined with an imaging agent.

Immunostimulatory Agents. As used herein, an immunostimulatory agent is an agent that stimulates an immune response (including enhancing a pre-existing immune response) in a subject to whom it is administered, whether alone or in combination with another agent. Examples include antigens, adjuvants (e.g., TLR ligands such as imiquimod, imidazoquinoline, nucleic acids comprising an unmethylated CpG dinucleotide, monophosphoryl lipid A or other lipopolysaccharide derivatives, single-stranded or double-stranded RNA, flagellin, muramyl dipeptide), cytokines including interleukins (e.g., IL-2, IL-7, IL-15 (or superagonist/mutant forms of these cytokines), IL-12, IFN-gamma, IFN-alpha, GM-CSF, FLT3-ligand, etc.), immunostimulatory antibodies (e.g., anti-CTLA-4, anti-CD28, anti-CD3, or single chain/antibody fragments of these molecules), and the like.

Antigens. The antigen may be without limitation a cancer antigen, a self antigen, a microbial antigen, an allergen, or an environmental antigen. The antigen may be peptide, lipid, or carbohydrate in nature, but it is not so limited.

Cancer Antigens. A cancer antigen is an antigen that is expressed preferentially by cancer cells (i.e., it is expressed at higher levels in cancer cells than on non-cancer cells) and in some instances it is expressed solely by cancer cells. The cancer antigen may be expressed within a cancer cell or on the surface of the cancer cell. The cancer antigen may be MART-1/Melan-A, gp100, adenosine deaminase-binding protein (ADAbp), FAP, cyclophilin b, colorectal associated antigen (CRC)—C017-IA/GA733, carcinoembryonic antigen (CEA), CAP-1, CAP-2, etv6, AML1, prostate specific antigen (PSA), PSA-1, PSA-2, PSA-3, prostate-specific membrane antigen (PSMA), T cell receptor/CD3-zeta chain, and CD20. The cancer antigen may be selected from the group consisting of MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5). The cancer antigen may be selected from the group consisting of GAGE-1, GAGE-2, GAGE-3, GAGE-4, GAGE-5, GAGE-6, GAGE-7, GAGE-8, GAGE-9. The cancer antigen may be selected from the group consisting of BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin, γ-catenin, p120ctn, gp100$^{Pmel117}$, PRAME, NY-ESO-1, cdc27, adenomatous polyposis coli protein (APC), fodrin, Connexin 37, Ig-idiotype, p15, gp75, GM2 ganglioside, GD2 ganglioside, human papilloma virus proteins, Smad family of tumor antigens, Imp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, CD20, and c-erbB-2.

Microbial Antigens. Microbial antigens are antigens derived from microbial species such as without limitation bacterial, viral, fungal, parasitic and mycobacterial species. As such, microbial antigens include bacterial antigens, viral antigens, fungal antigens, parasitic antigens, and mycobacterial antigens. Examples of bacterial, viral, fungal, parasitic and mycobacterial species are provided herein. The microbial antigen may be part of a microbial species or it may be the entire microbe.

Allergens. An allergen is an agent that can induce an allergic or asthmatic response in a subject. Allergens include without limitation pollens, insect venoms, animal dander dust, fungal spores and drugs (e.g. penicillin). Examples of natural, animal and plant allergens include but are not limited to proteins specific to the following genera: Canine (*Canis familiaris*); *Dermatophagoides* (e.g. *Dermatophagoides farinae*); *Felis* (*Felis domesticus*); *Ambrosia* (*Ambrosia artemisifolia*; *Lolium* (e.g. *Lolium perenne* or *Lolium multiflorum*); *Cryptomeria* (*Cryptomeria japonica*); *Alternaria* (*Alternaria alternata*); *Alder*; *Alnus* (*Alnus gultinoasa*); *Betula* (*Betula verrucosa*); *Quercus* (*Quercus alba*); *Olea* (*Olea europa*); *Artemisia* (*Artemisia vulgaris*); *Plantago* (e.g. *Plantago lanceolata*); *Parietaria* (e.g. *Parietaria officinalis* or *Parietaria judaica*); *Blattella* (e.g. *Blattella germanica*); *Apis* (e.g. *Apis multiflorum*); *Cupressus* (e.g. *Cupressus sempervirens*, *Cupressus arizonica* and *Cupressus macrocarpa*); *Juniperus* (e.g. *Juniperus sabinoides, Juniperus virginiana, Juniperus communis* and *Juniperus ashei*); *Thuya* (e.g. *Thuya orientalis*); *Chamaecyparis* (e.g. *Chamaecyparis obtusa*); *Periplaneta* (e.g. *Periplaneta americana*); *Agropyron* (e.g. *Agropyron repens*); *Secale* (e.g. *Secale cereale*); *Triticum* (e.g. *Triticum aestivum*); *Dactylis* (e.g. *Dactylis glomerata*); *Festuca* (e.g. *Festuca elatior*); *Poa* (e.g. *Poa pratensis* or *Poa compressa*); *Avena* (e.g. *Avena sativa*); *Holcus* (e.g. *Holcus lanatus*); *Anthoxanthum* (e.g. *Anthoxanthum odoratum*); *Arrhenatherum* (e.g. *Arrhenatherum elatius*); *Agrostis* (e.g. *Agrostis alba*); *Phleum* (e.g. *Phleum pratense*); *Phalaris* (e.g. *Phalaris arundinacea*); *Paspalum* (e.g. *Paspalum notatum*); *Sorghum* (e.g. *Sorghum halepensis*); and *Bromus* (e.g. *Bromus inermis*).

Adjuvants. The adjuvant may be without limitation alum (e.g., aluminum hydroxide, aluminum phosphate); saponins purified from the bark of the *Q. saponaria* tree such as QS21 (a glycolipid that elutes in the 21st peak with HPLC fractionation; Antigenics, Inc., Worcester, Mass.); poly[di(carboxylatophenoxy)phosphazene (PCPP polymer; Virus Research Institute, USA), Flt3 ligand, *Leishmania* elongation factor (a purified *Leishmania* protein; Corixa Corporation, Seattle, Wash.), ISCOMS (immunostimulating complexes which contain mixed saponins, lipids and form virus-sized particles with pores that can hold antigen; CSL, Melbourne, Australia), Pam3Cys, SB-AS4 (SmithKline Beecham adjuvant system #4 which contains alum and MPL; SBB, Belgium), non-ionic block copolymers that form micelles such as CRL 1005 (these contain a linear chain of hydrophobic polyoxypropylene flanked by chains of polyoxyethylene, Vaxcel, Inc., Norcross, Ga.), and Montanide IMS (e.g., IMS 1312, water-based nanoparticles combined with a soluble immunostimulant, Seppic)

Adjuvants may be TLR ligands. Adjuvants that act through TLR3 include without limitation double-stranded RNA. Adjuvants that act through TLR4 include without limitation derivatives of lipopolysaccharides such as monophosphoryl lipid A (MPLA; Ribi ImmunoChem Research, Inc., Hamilton, Mont.) and muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland). Adjuvants that act through TLR5 include without limitation flagellin. Adjuvants that act through TLR7 and/or TLR8 include single-stranded RNA, oligoribonucleotides (ORN), synthetic low molecular weight compounds such as imidazoquinolinamines (e.g., imiquimod, resiquimod). Adjuvants acting through TLR9 include DNA of viral or bacterial origin, or synthetic oligodeoxynucleotides (ODN), such as CpG ODN. Another adjuvant class is phosphorothioate containing molecules such as phosphorothioate nucleotide analogs and nucleic acids containing phosphorothioate backbone linkages.

Immunoinhibitory Agents. As used herein, an immunoinhibitory agent is an agent that inhibits an immune response in a subject to whom it is administered, whether alone or in combination with another agent. Examples include steroids, retinoic acid, dexamethasone, cyclophosphamide, anti-CD3 antibody or antibody fragment, and other immunosuppressants.

Anti-Cancer Agents. As used herein, an anti-cancer agent is an agent that at least partially inhibits the development or progression of a cancer, including inhibiting in whole or in part symptoms associated with the cancer even if only for the short term. Several anti-cancer agents can be categorized as DNA damaging agents and these include topoisomerase inhibitors (e.g., etoposide, ramptothecin, topotecan, teniposide, mitoxantrone), DNA alkylating agents (e.g., cisplatin, mechlorethamine, cyclophosphamide, ifosfamide, melphalan, chorambucil, busulfan, thiotepa, carmustine, lomustine, carboplatin, dacarbazine, procarbazine), DNA strand break inducing agents (e.g., bleomycin, doxorubicin, daunorubicin, idarubicin, mitomycin C), anti-microtubule agents (e.g., vincristine, vinblastine), anti-metabolic agents (e.g., cytarabine, methotrexate, hydroxyurea, 5-fluorouracil, floxuridine, 6-thioguanine, 6-mercaptopurine, fludarabine, pentostatin, chlorodeoxyadenosine), anthracyclines, vinca alkaloids. or epipodophyllotoxins.

Examples of anti-cancer agents include without limitation Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Bortezomib (VELCADE); Brequinar Sodium; Bropirimine; Busulfan; Cactinomycin; Calusterone; Caracemide; Carbetimer; Carboplatin (a platinum-containing regimen); Carmustine; Carubicin Hydrochloride; Carzelesin; Cedefingol; Chlorambucil; Cirolemycin; Cisplatin (a platinum-containing regimen); Cladribine; Crisnatol Mesylate; Cyclophosphamide; Cytarabine; Dacarbazine; Dactinomycin; Daunorubicin; Decitabine; Dexormaplatin; Dezaguanine; Diaziquone; Docetaxel (TAXOTERE); Doxorubicin; Droloxifene; Dromostanolone; Duazomycin; Edatrexate; Eflornithine; Elsamitrucin; Enloplatin; Enpromate; Epipropidine; Epirubicin; Erbulozole; Erlotinib (TARCEVA), Esorubicin; Estramustine; Etanidazole; Etoposide; Etoprine; Fadrozole; Fazarabine; Fenretinide; Floxuridine; Fludarabine; 5-Fluorouracil; Flurocitabine; Fosquidone; Fostriecin; Gefitinib (IRESSA), Gemcitabine; Hydroxyurea; Idarubicin; Ifosfamide; Ilmofosine; Imatinib mesylate (GLEEVAC); Interferon alpha-2a; Interferon alpha-2b; Interferon alpha-n1; Interferon alpha-n3; Interferon beta-I a; Interferon gamma-I b; Iproplatin; Irinotecan; Lanreotide; Lenalidomide (REVLIMID, REVIMID); Letrozole; Leuprolide; Liarozole; Lometrexol; Lomustine; Losoxantrone; Masoprocol; Maytansine; Mechlorethamine; Megestrol; Melengestrol; Melphalan; Menogaril; Mercaptopurine;

Methotrexate; Metoprine; Meturedepa; Mitindomide; Mitocarcin; Mitocromin; Mitogillin; Mitomalcin; Mitomycin; Mitosper; Mitotane; Mitoxantrone; Mycophenolic Acid; Nocodazole; Nogalamycin; Ormaplatin; Oxisuran; Paclitaxel; Pemetrexed (ALIMTA), Pegaspargase; Peliomycin; Pentamustine; Pentomone; Peplomycin; Perfosfamide; Pipobroman; Piposulfan; Piritrexim Isethionate; Piroxantrone; Plicamycin; Plomestane; Porfimer; Porfiromycin; Prednimustine; Procarbazine; Puromycin; Pyrazofurin; Riboprine; Rogletimide; Safingol; Semustine; Simtrazene; Sitogluside; Sparfosate; Sparsomycin; Spirogermanium; Spiromustine; Spiroplatin; Streptonigrin; Streptozocin; Sulofenur; Talisomycin; Tamsulosin; Taxol; Taxotere; Tecogalan; Tegafur; Teloxantrone; Temoporfin; Temozolomide (TEMODAR); Teniposide; Teroxirone; Testolactone; Thalidomide (THALOMID) and derivatives thereof; Thiamiprine; Thioguanine; Thiotepa; Tiazofurin; Tirapazamine; Topotecan; Toremifene; Trestolone; Triciribine; Trimetrexate; Triptorelin; Tubulozole; Uracil Mustard; Uredepa; Vapreotide; Verteporfin; Vinblastine; Vincristine; Vindesine; Vinepidine; Vinglycinate; Vinleurosine; Vinorelbine; Vinrosidine; Vinzolidine; Vorozole; Zeniplatin; Zinostatin; Zorubicin.

The anti-cancer agent may be an enzyme inhibitor including without limitation tyrosine kinase inhibitor, a CDK inhibitor, a MAP kinase inhibitor, or an EGFR inhibitor. The tyrosine kinase inhibitor may be without limitation Genistein (4',5,7-trihydroxyisoflavone), Tyrphostin 25 (3,4,5-trihydroxyphenyl), methylene]-propanedinitrile, Herbimycin A, Daidzein (4',7-dihydroxyisoflavone), AG-126, trans-1-(3'-carboxy-4'-hydroxyphenyl)-2-(2",5"-dihydroxy-phenyl) ethane, or HDBA (2-Hydroxy5-(2,5-Dihydroxybenzylamino)-2-hydroxybenzoic acid. The CDK inhibitor may be without limitation p21, p27, p57, p15, p16, p18, or p19. The MAP kinase inhibitor may be without limitation KY12420 ($C_{23}H_{24}O_8$), CNI-1493, PD98059, or 4-(4-Fluorophenyl)-2-(4-methylsulfinyl phenyl)-5-(4-pyridyl) 1H-imidazole. The EGFR inhibitor may be without limitation erlotinib (TARCEVA), gefitinib (IRESSA), WHI-P97 (quinazoline derivative), LFM-A12 (leflunomide metabolite analog), ABX-EGF, lapatinib, canertinib, ZD-6474 (ZACTIMA), AEE788, and AG1458.

The anti-cancer agent may be a VEGF inhibitor including without limitation bevacizumab (AVASTIN), ranibizumab (LUCENTIS), pegaptanib (MACUGEN), sorafenib, sunitinib (SUTENT), vatalanib, ZD-6474 (ZACTIMA), anecortave (RETAANE), squalamine lactate, and semaphorin.

The anti-cancer agent may be an antibody or an antibody fragment including without limitation an antibody or an antibody fragment including but not limited to bevacizumab (AVASTIN), trastuzumab (HERCEPTIN), alemtuzumab (CAMPATH, indicated for B cell chronic lymphocytic leukemia,), gemtuzumab (MYLOTARG, hP67.6, anti-CD33, indicated for leukemia such as acute myeloid leukemia), rituximab (RITUXAN), tositumomab (BEXXAR, anti-CD20, indicated for B cell malignancy), MDX-210 (bispecific antibody that binds simultaneously to HER-2/neu oncogene protein product and type I Fc receptors for immunoglobulin G (IgG) (Fc gamma RI)), oregovomab (OVAREX, indicated for ovarian cancer), edrecolomab (PANOREX), daclizumab (ZENAPAX), palivizumab (SYNAGIS, indicated for respiratory conditions such as RSV infection), ibritumomab tiuxetan (ZEVALIN, indicated for Non-Hodgkin's lymphoma), cetuximab (ERBITUX), MDX-447, MDX-22, MDX-220 (anti-TAG-72), IOR-C5, IOR-T6 (anti-CD1), IOR EGF/R3, celogovab (ONCOSCINT OV103), epratuzumab (LYMPHOCIDE), pemtumomab (THERAGYN), and Gliomab-H (indicated for brain cancer, melanoma).

Hematopoietic Differentiating Agents. The agent may be one that stimulates the differentiation of hematopoietic progenitor cells towards one or more lineages. Examples include without limitation IL-3, G-CSF, GM-CSF, M-CSF, thrombopoeitin, erythropoietin, Wnt5A, Wnt11A, and the like.

Hematopoietic Self-Renewing Agents. The agent may be one that stimulates the self-renewal of hematopoietic progenitor cells. Examples include without limitation kit ligand, GSK3-beta inhibitors, Wnt5A together with SLF, Notch1 activators, Lnk inhibitors, prostaglandin E2 (PGE2) and agents that stimulate the PGE2 pathway including PGE2, PGI2, Linoleic Acid, 13(s)-HODE, LY171883, Mead Acid, Eicosatrienoic Acid, Epoxyeicosatrienoic Acid, ONO-259, Cay1039, a PGE2 receptor agonist, of 16,16-dimethyl PGE2, 19(R)-hydroxy PGE2, 16,16-dimethyl PGE2 p-(p-acetamidobenzamido)phenyl ester, 11-deoxy-16,16-dimethyl PGE2, 9-deoxy-9-methylene-16,16-dimethyl PGE2, 9-deoxy-9-methylene PGE2, Butaprost, Sulprostone, PGE2 serinol amide, PGE2 methyl ester, 16-phenyl tetranor PGE2,15(S)-15-methyl PGE2,15(R)-15-methyl PGE2, BIO, 8-bromo-cAMP, Forskolin, Banta-AM, Fendiline, Nicardipine, Nifedipine, Pimozide, Strophanthidin, Lanatoside, L-Arg, Sodium Nitroprusside, Sodium Vanadate, Bradykinin, Mebeverine, Flurandrenolide, Atenolol, Pindolol, Gaboxadol, Kynurenic Acid, Hydralazine, Thiabendazole, Bicuclline, Vesamicol, Peruvoside, Imipramine, Chlorpropamide, 1,5-Pentamethylenetetrazole, 4-Aminopyridine, Diazoxide, Benfotiamine, 12-Methoxydodecenoic acid, N-Formyl-Met-Leu-Phe, Gallamine, IAA 94, Chlorotrianisene, and derivatives thereof, and the like.

Anti-Infective Agents. The agent may be an anti-infective agent including without limitation an anti-bacterial agent, an anti-viral agent, an anti-parasitic agent, an anti-fungal agent, and an anti-mycobacterial agent.

Anti-bacterial agents may be without limitation β-lactam antibiotics, penicillins (such as natural penicillins, aminopenicillins, penicillinase-resistant penicillins, carboxy penicillins, ureido penicillins), cephalosporins (first generation, second generation, and third generation cephalosporins), other β-lactams (such as imipenem, monobactams), β-lactamase inhibitors, vancomycin, aminoglycosides and spectinomycin, tetracyclines, chloramphenicol, erythromycin, lincomycin, clindamycin, rifampin, metronidazole, polymyxins, sulfonamides and trimethoprim, or quinolines.

Other anti-bacterials may be without limitation Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefmenoxime Hydrochloride; Cefmetazole; Cefinetazole Sodium; Cefonicid Monosodium; Cefonicid Sodium; Cefoperazone Sodium; Ceforanide; Cefotaxime Sodium;

Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpirinol; Nifurquinazol; Nifurthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; or Zorbamycin.

Anti-mycobacterial agents may be without limitation Myambutol (Ethambutol Hydrochloride), Dapsone (4,4'-diaminodiphenylsulfone), Paser Granules (aminosalicylic acid granules), Priftin (rifapentine), Pyrazinamide, Isoniazid, Rifadin (Rifampin), Rifadin IV, Rifamate (Rifampin and Isoniazid), Rifater (Rifampin, Isoniazid, and Pyrazinamide), Streptomycin Sulfate or Trecator-SC (Ethionamide).

Anti-viral agents may be without limitation amantidine and rimantadine, ribivarin, acyclovir, vidarabine, trifluorothymidine, ganciclovir, zidovudine, retinovir, and interferons.

Anti-viral agents may be without limitation further include Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; Zinviroxime or integrase inhibitors.

Anti-fungal agents may be without limitation imidazoles and triazoles, polyene macrolide antibiotics, griseofulvin, amphotericin B, and flucytosine. Antiparasites include heavy metals, antimalarial quinolines, folate antagonists, nitroimidazoles, benzimidazoles, avermectins, praxiquantel, ornithine decarboxylase inhibitors, phenols (e.g., bithionol, niclosamide); synthetic alkaloid (e.g., dehydroemetine); piperazines (e.g., diethylcarbamazine); acetanilide (e.g., diloxanide furonate); halogenated quinolines (e.g., iodoquinol (diiodohydroxyquin)); nitrofurans (e.g., nifurtimox); diamidines (e.g., pentamidine); tetrahydropyrimidine (e.g., pyrantel pamoate); or sulfated naphthylamine (e.g., suramin).

Other anti-infective agents may be without limitation Difloxacin Hydrochloride; Lauryl Isoquinolinium. Bromide; Moxalactam Disodium; Ornidazole; Pentisomicin; Sarafloxacin Hydrochloride; Protease inhibitors of HIV and other retroviruses; Integrase Inhibitors of HIV and other retroviruses; Cefaclor (Ceclor); Acyclovir (Zovirax); Norfloxacin (Noroxin); Cefoxitin (Mefoxin); Cefuroxime axetil (Ceftin); Ciprofloxacin (Cipro); Aminacrine Hydrochloride; Benzethonium Chloride : Bithionolate Sodium; Bromchlorenone; Carbamide Peroxide; Cetalkonium Chloride; Cetylpyridinium Chloride:Chlorhexidine Hydrochloride; Clioquinol; Domiphen Bromide; Fenticlor; Fludazonium Chloride; Fuchsin, Basic; Furazolidone; Gentian Violet; Halquinols; Hexachlorophene:Hydrogen Peroxide; Ichthammol; Imidecyl Iodine; Iodine; Isopropyl Alcohol; Mafenide Acetate; Meralein Sodium; Mercufenol Chloride; Mercury, Ammoniated; Methylbenzethonium Chloride; Nitrofurazone; Nitromersol; Octenidine Hydrochloride; Oxychlorosene; Oxychlorosene Sodium; Parachlorophenol, Camphorated; Potassium Permanganate; Povidone-Iodine; Sepazonium Chloride; Silver Nitrate; Sulfadiazine, Silver; Symclosene; Thimerfonate Sodium; Thimerosal; or Troclosene Potassium.

Nucleic Acid Agents. Nucleic acids that can be delivered to a subject according to the invention include naturally or non-naturally occurring DNA (including cDNA, genomic DNA, nuclear DNA, mitochondrial DNA), RNA (including mRNA, rRNA, tRNA), oligonucleotides, a triple-helix forming molecule, immunostimulatory nucleic acids such as those described in U.S. Pat. No. 6,194,388 (the teachings of which relating to immunostimulatory CpG nucleic acids are incorporated herein by reference), small interfering RNA (siRNA) used to modulate gene expression, antisense oligonucleotides used to modulate gene expression, aptamers, ribozymes, a gene or gene fragment, a regulatory sequence, including analogs, derivatives, and combinations thereof. These nucleic acids may be administered neat or complexed to another entity, for example in order to facilitate their binding to and/or uptake by target tissues and/or cells.

Other Agents. The agent may be without limitation adrenergic agent; adrenocortical steroid; adrenocortical suppressant; alcohol deterrent; aldosterone antagonist; ammonia detoxicant; amino acid; amylotropic lateral sclerosis agent; anabolic; analeptic; analgesic; androgen; anesthetic; anorectic; anorexic; anterior pituitary activator; anterior pituitary suppressant; anthelmintic; anti-acne agent; anti-adrenergic; anti-allergic; anti-amebic; anti-androgen; anti-anemic; anti-anginal; anti-anxiety; anti-arthritic; anti-asthmatic including β-adrenergic agonists, methylxanthines, mast cell stabilizing agents, anticholinergics, adrenocortical steroids such as glucocorticoids; anti-atherosclerotic; anticholelithic; anticholelithogenic; anticholinergic; anticoagulant; anticoccidal; anticonvulsant; antidepressant; antidiabetic; antidiarrheal; antidiuretic; antidote; antidyskinetic; anti-emetic; anti-epileptic; anti-estrogen; antifibrinolytic; antiglaucoma; antihemorrhagic; antihemorrheologic; antihistamine; antihyperlipidemic; antihyperlipoproteinemic; antihypertensive; antihypotensive; anti-infective; anti-inflammatory; antikeratinizing agent; antimigraine; antimitotic; antimycotic; antinauseant; antineutropenic; antiobsessional agent; antioxidant; antiparkinsonian; antiperistaltic; antipneumocystic; antiprostatic hypertrophy agent; antiprotozoal; antipruritic; antipsoriatic; antipsychotic; antirheumatic; antischistosomal; antiseborrheic; antisecretory; antispasmodic; antithrombotic; antitussive; anti-ulcerative; anti-urolithic; appetite suppressant; blood glucose regulator; bone resorption inhibitor; bronchodilator; carbonic anhydrase inhibitor; cardiac depressant; cardioprotectant; cardiotonic; cardiovascular agent; cerebral ischemia agent; choleretic; cholinergic; cholinergic agonist; cholinesterase deactivator; coccidiostat; cognition adjuvant; cognition enhancer; conjunctivitis agent; contrast agent; depressant; diagnostic aid; diuretic; dopaminergic agent; ectoparasiticide; emetic; enzyme inhibitor; estrogen; estrogen receptor agonist; fibrinolytic; fluorescent agent; free oxygen radical scavenger; gastric acid suppressant; gastrointestinal motility effector; geriatric agent; glucocorticoid; gonad-stimulating principle; hair growth stimulant; hemostatic; herbal active agent; histamine H2 receptor antagonists; hormone; hypocholesterolemic; hypoglycemic; hypolipidemic; hypotensive; HMGCoA reductase inhibitor; impotence therapy adjunct; inflammatory bowel disease agent; keratolytic; LHRH agonist; liver disorder agent; luteolysin; memory adjuvant; mental performance enhancer; mineral; mood regulator; mucolytic; mucosal protective agent; multiple sclerosis agent; mydriatic; nasal decongestant; neuroleptic; neuromuscular blocking agent; neuroprotective; NMDA antagonist; non-hormonal sterol derivative; nutrient; oxytocic; Paget's disease agent; plasminogen activator; platelet activating factor antagonist; platelet aggregation inhibitor; post-stroke and post-head trauma agents; progestin; prostaglandin; prostate growth inhibitor; prothyrotropin; psychotropic; radioactive agent; relaxant; rhinitis agent; scabicide; sclerosing agent; sedative; sedative-hypnotic; selective adenosine A1 antagonist; sequestering agents; serotonin antagonist; serotonin inhibitor; serotonin receptor antagonist; steroid; stimulant; suppressant; thyroid hormone; thyroid inhibitor; thyromimetic; tranquilizer; unstable angina agent; uricosuric; vasoconstrictor; vasodilator; vulnerary; wound healing agent; or xanthine oxidase inhibitor.

Subjects

The invention can be practiced in virtually any subject type that is likely to benefit from localized delivery of agents as contemplated herein. Human subjects are preferred subjects in some embodiments of the invention. Subjects also include animals such as household pets (e.g., dogs, cats, rabbits, ferrets, etc.), livestock or farm animals (e.g., cows, pigs, sheep, chickens and other poultry), horses such as thoroughbred horses, laboratory animals (e.g., mice, rats, rabbits, etc.), and the like. Subjects also include fish and other aquatic species.

The subjects to whom the agents are delivered may be normal subjects. Alternatively they may have or may be at risk of developing a condition that can be diagnosed or that can benefit from localized delivery of one or more particular agents.

Such conditions include cancer (e.g., solid tumor cancers), infections (particularly infections localized to particular regions or tissues in the body), autoimmune disorders, allergies or allergic conditions, asthma, transplant rejection, and the like.

Tests for diagnosing various of the conditions embraced by the invention are known in the art and will be familiar to the ordinary medical practitioner. These laboratory tests include without limitation microscopic analyses, cultivation dependent tests (such as cultures), and nucleic acid detection tests. These include wet mounts, stain-enhanced microscopy, immune microscopy (e.g., FISH), hybridization microscopy, particle agglutination, enzyme-linked immunosorbent assays, urine screening tests, DNA probe hybridization, serologic tests, etc. The medical practitioner will generally also take a full history and conduct a complete physical examination in addition to running the laboratory tests listed above.

A subject having a cancer is a subject that has detectable cancer cells. A subject at risk of developing a cancer is a subject that has a higher than normal probability of developing cancer. These subjects include, for instance, subjects having a genetic abnormality that has been demonstrated to be associated with a higher likelihood of developing a cancer, subjects having a familial disposition to cancer, subjects exposed to cancer causing agents (i.e., carcinogens) such as tobacco, asbestos, or other chemical toxins, and subjects previously treated for cancer and in apparent remission.

Subjects having an infection are those that exhibit symptoms thereof including without limitation fever, chills, myalgia, photophobia, pharyngitis, acute lymphadenopathy, splenomegaly, gastrointestinal upset, leukocytosis or leukopenia, and/or those in whom infectious pathogens or byproducts thereof can be detected.

A subject at risk of developing an infection is one that is at risk of exposure to an infectious pathogen. Such subjects include those that live in an area where such pathogens are known to exist and where such infections are common. These subjects also include those that engage in high risk activities such as sharing of needles, engaging in unprotected sexual activity, routine contact with infected samples of subjects (e.g., medical practitioners), people who have undergone surgery, including but not limited to abdominal surgery, etc.

The subject may have or may be at risk of developing an infection such as a bacterial infection, a viral infection, a fungal infection, a parasitic infection or a mycobacterial infection. In these embodiments, the nanoparticles may comprise an anti-microbial agent such as an anti-bacterial agent, an anti-viral agent, an anti-fungal agent, an anti-parasitic agent, or an anti-mycobacterial agent and the cell carriers (e.g., the T cells) may be genetically engineered to produce another agent useful in stimulating an immune response against the infection, or potentially treating the infection.

In some instances, the subjects to whom the carrier cell-nanoparticle conjugates are administered are in need of hematopoietic reconstitution. Such subjects may have been exposed to a deliberate or accidental myeloablative event, including without limitation myeloablative chemotherapy and/or whole body radiation, as may be given as part of a therapeutic regimen for non-solid cancers or metastatic cancers. The invention contemplates administering to such subjects hematopoietic progenitor cells conjugated to nanoparticles that comprise agents capable of stimulating the proliferation of the progenitor cells. In some instances, the agents may also be differentiating agents (i.e., agents that drive the progenitor cells and their progeny to differentiate, optionally towards all lineages or a subset of lineages. In other instances, the agents may be self-renewal agents (i.e., agents that drive the progenitor cells to self-renew). In yet other instances, the carrier cells may be conjugated to nanoparticles that comprise both types of agents, whether such agents be in the same nanoparticle or in different nanoparticles. Moreover, the invention further contemplates that exposure of the subject to these different agents may be staggered (e.g., exposure to the self-renewing agents may occur before exposure to the differentiating agents).

Cancer

The invention contemplates administration of the nanoparticle-cell conjugates to subjects having or at risk of developing a cancer including for example a solid tumor cancer. The cancer may be carcinoma, sarcoma or melanoma. Carcinomas include without limitation to basal cell carcinoma, biliary tract cancer, bladder cancer, breast cancer, cervical cancer, choriocarcinoma, CNS cancer, colon and rectum cancer, kidney or renal cell cancer, larynx cancer, liver cancer, small cell lung cancer, non-small cell lung cancer (NSCLC, including adenocarcinoma, giant (or oat) cell carcinoma, and squamous cell carcinoma), oral cavity cancer, ovarian cancer, pancreatic cancer, prostate cancer, skin cancer (including basal cell cancer and squamous cell cancer), stomach cancer, testicular cancer, thyroid cancer, uterine cancer, rectal cancer, cancer of the respiratory system, and cancer of the urinary system.

Sarcomas are rare mesenchymal neoplasms that arise in bone (osteosarcomas) and soft tissues (fibrosarcomas). Sarcomas include without limitation liposarcomas (including myxoid liposarcomas and pleiomorphic liposarcomas), leiomyosarcomas, rhabdomyosarcomas, malignant peripheral nerve sheath tumors (also called malignant schwannomas, neurofibrosarcomas, or neurogenic sarcomas), Ewing's tumors (including Ewing's sarcoma of bone, extraskeletal (i.e., not bone) Ewing's sarcoma, and primitive neuroectodermal tumor), synovial sarcoma, angiosarcomas, hemangiosarcomas, lymphangiosarcomas, Kaposi's sarcoma, hemangioendothelioma, desmoid tumor (also called aggressive fibromatosis), dermatofibrosarcoma protuberans (DFSP), malignant fibrous histiocytoma (MFH), hemangiopericytoma, malignant mesenchymoma, alveolar soft-part sarcoma, epithelioid sarcoma, clear cell sarcoma, desmoplastic small cell tumor, gastrointestinal stromal tumor (GIST) (also known as GI stromal sarcoma), and chondrosarcoma.

Melanomas are tumors arising from the melanocytic system of the skin and other organs. Examples of melanoma include without limitation lentigo maligna melanoma, superficial spreading melanoma, nodular melanoma, and acral lentiginous melanoma.

The cancer may be a solid tumor lymphoma. Examples include Hodgkin's lymphoma, Non-Hodgkin's lymphoma, and B cell lymphoma.

The cancer may be without limitation bone cancer, brain cancer, breast cancer, colorectal cancer, connective tissue cancer, cancer of the digestive system, endometrial cancer, esophageal cancer, eye cancer, cancer of the head and neck, gastric cancer, intra-epithelial neoplasm, melanoma neuroblastoma, Non-Hodgkin's lymphoma, non-small cell lung cancer, prostate cancer, retinoblastoma, or rhabdomyosarcoma.

Infection

The invention contemplates administration of the nanoparticle-cell conjugates to subjects having or at risk of developing an infection such as a bacterial infection, a viral infection, a fungal infection, a parasitic infection or a mycobacterial infection.

The bacterial infection may be without limitation an *E. coli* infection, a Staphylococcal infection, a Streptococcal infection, a *Pseudomonas* infection, *Clostridium difficile* infection, *Legionella* infection, *Pneumococcus* infection, *Haemophilus* infection, *Klebsiella* infection, *Enterobacter* infection, *Citrobacter* infection, *Neisseria* infection, *Shigella* infection, *Salmonella* infection, *Listeria* infection, *Pasteurella* infection, *Streptobacillus* infection, *Spirillum* infection, *Treponema* infection, *Actinomyces* infection, *Borrelia* infection, *Corynebacterium* infection, *Nocardia* infection, *Gardnerella* infection, *Campylobacter* infection, *Spirochaeta* infection, *Proteus* infection, *Bacteriodes* infection, *H. pylori* infection, or anthrax infection.

The mycobacterial infection may be without limitation tuberculosis or leprosy respectively caused by the *M. tuberculosis* and *M. leprae* species.

The viral infection may be without limitation a Herpes simplex virus 1 infection, a Herpes simplex virus 2 infection, cytomegalovirus infection, hepatitis A virus infection, hepatitis B virus infection, hepatitis C virus infection, human papilloma virus infection, Epstein Barr virus infection, rotavirus infection, adenovirus infection, influenza A virus infection, H1N1 (swine flu) infection, respiratory syncytial virus infection, varicella-zoster virus infections, small pox infection, monkey pox infection, SARS infection or avian flu infection.

The fungal infection may be without limitation candidiasis, ringworm, histoplasmosis, blastomycosis, paracoccidioidomycosis, crytococcosis, aspergillosis, chromomycosis, mycetoma infections, pseudallescheriasis, or tinea versicolor infection.

The parasite infection may be without limitation amebiasis, *Trypanosoma cruzi* infection, Fascioliasis, Leishmaniasis, *Plasmodium* infections, Onchocerciasis, Paragonimiasis, *Trypanosoma brucei* infection, *Pneumocystis* infection, *Trichomonas vaginalis* infection, *Taenia* infection, Hymenolepsis infection, Echinococcus infections, Schistosomiasis, neurocysticercosis, *Necator americanus* infection, or *Trichuris trichuria* infection.

Allergy and Asthma

The invention contemplates administration of the nanoparticle-cell conjugates to subjects having or at risk of developing an allergy or asthma. An allergy is an acquired hypersensitivity to an allergen. Allergic conditions include but are not limited to eczema, allergic rhinitis or coryza, hay fever, bronchial asthma, urticaria (hives) and food allergies, and other atopic conditions. Allergies are generally caused by IgE antibody generation against harmless allergens. Asthma is a disorder of the respiratory system characterized by inflammation, narrowing of the airways and increased reactivity of the airways to inhaled agents. Asthma is frequently, although not exclusively, associated with atopic or allergic symptoms. Administration of Th1 cytokines, such as IL-12 and IFN-gamma, according to the invention can be used to treat allergy or asthma.

Autoimmune Disease

The invention contemplates administration of the nanoparticle-cell conjugates to subjects having or at risk of developing an autoimmune disease. Autoimmune disease is a class of diseases in which a subject's own antibodies react with host tissue or in which immune effector T cells are autoreactive to endogenous self peptides and cause destruction of tissue. Thus an immune response is mounted against a subject's own antigens, referred to as self antigens. Autoimmune diseases are generally considered to be Th1 biased. As a result, induction of a Th2 immune response or Th2 like cytokines can be beneficial. Such cytokines include IL-4, IL-5 and IL-10.

Autoimmune diseases include but are not limited to rheumatoid arthritis, Crohn's disease, multiple sclerosis, systemic lupus erythematosus (SLE), autoimmune encephalomyelitis, myasthenia gravis (MG), Hashimoto's thyroiditis, Goodpasture's syndrome, pemphigus (e.g., pemphigus vulgaris), Grave's disease, autoimmune hemolytic anemia, autoimmune thrombocytopenic purpura, scleroderma with anti-collagen antibodies, mixed connective tissue disease, polymyositis, pernicious anemia, idiopathic Addison's disease, autoimmune-associated infertility, glomerulonephritis (e.g., crescentic glomerulonephritis, proliferative glomerulonephritis), bullous pemphigoid, Sjögren's syndrome, insulin resistance, and autoimmune diabetes mellitus.

Transplant Therapy

The methods provided herein may also be used to modulate immune responses following transplant therapy. Transplant success is often limited by rejection of the transplanted tissue by the body's immune system. As a result, transplant recipients are usually immunosuppressed for extended periods of time in order to allow the transplanted tissue to survive. The invention contemplates localized delivery of immunomodulators, and particularly immunoinhibitory agents, to transplant sites in order to minimize transplant rejection. Thus, the invention contemplates administration of the nanoparticle-cell conjugates to subjects that are going to undergo, are undergoing, or have undergone a transplant.

The foregoing lists are not intended to be exhaustive but rather exemplary. Those of ordinary skill in the art will identify other examples of each condition type that are amenable to prevention and treatment using the methods of the invention.

Effective Amounts, Regimens, Formulations

The agents are administered in effective amounts. An effective amount is a dosage of the agent sufficient to provide a medically desirable result. The effective amount will vary with the particular condition being treated, the age and physical condition of the subject being treated, the severity of the condition, the duration of the treatment, the nature of the concurrent or combination therapy (if any), the specific route of administration and like factors within the knowledge and expertise of the health practitioner. It is preferred generally that a maximum dose be used, that is, the highest safe dose according to sound medical judgment.

For example, if the subject has a tumor, an effective amount may be that amount that reduces the tumor volume or load (as for example determined by imaging the tumor). Effective amounts may also be assessed by the presence and/or frequency of cancer cells in the blood or other body fluid or tissue (e.g., a biopsy). If the tumor is impacting the normal functioning of a tissue or organ, then the effective amount may be assessed by measuring the normal functioning of the tissue or organ.

The invention provides pharmaceutical compositions. Pharmaceutical compositions are sterile compositions that comprise cells, nanoparticles and/or agent(s), preferably in a pharmaceutically-acceptable carrier. The term "pharmaceutically-acceptable carrier" means one or more compatible solid or liquid filler, diluents or encapsulating substances which are suitable for administration to a human or other subject contemplated by the invention. The term "carrier" denotes an organic or inorganic ingredient, natural or synthetic, with which the cells, nanoparticles and agent(s) are combined to facilitate administration. The components of the pharmaceutical compositions are commingled in a manner that precludes interaction that would substantially impair their desired pharmaceutical efficiency.

The nanoparticle-cell conjugates, when it is desirable to deliver them systemically, may be formulated for parenteral administration by injection, e.g., by bolus injection or continuous infusion. Formulations for injection may be presented in unit dosage form, e.g., in ampoules or in multi-dose containers. Pharmaceutical parenteral formulations include aqueous solutions of the ingredients. Aqueous injection suspensions may contain substances which increase the viscosity of the suspension, such as sodium carboxymethyl cellulose, sorbitol, or dextran. Alternatively, suspensions of ingredients may be prepared as oil-based suspensions. Suitable lipophilic solvents or vehicles include fatty oils such as sesame oil, or synthetic fatty acid esters, such as ethyl oleate or triglycerides, or liposomes.

EXAMPLES

Example 1

Figure 2A:
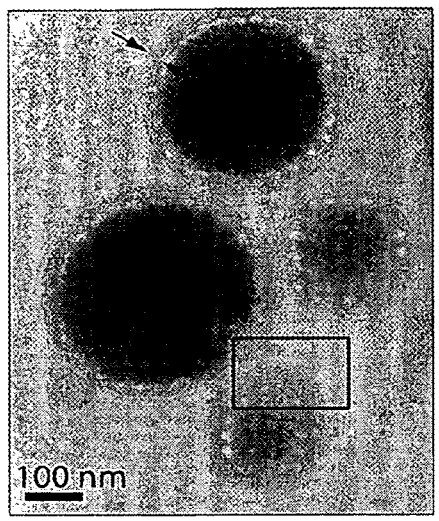
FIGS. 2A-D. Liposomes and lipid-coated PLGA nanoparticles for linkage to T cells. (A, B) Unstained cryo-electron microscopy images of lipid-enveloped nanoparticles, illustrating surface lipids. (B is magnified view of A inset.) Arrows highlight evidence for bilayer formation at the surface of the enveloped nanoparticles. (C) Size histograms of lipid-coated PLGA nanoparticles and liposomes from cryoEM. (D) Schematic of maleimide-based conjugation to T cell surface thiols.
Figure 2B:
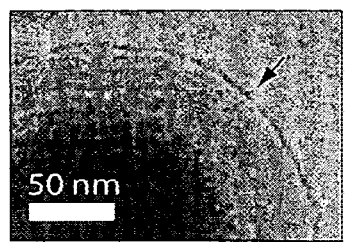

Nanoparticle Synthesis, Characterization and Conjugation to T Cells 1.1. Nanoparticle Synthesis. We recently developed a strategy to prepare 'lipid-enveloped' biodegradable polymer nanoparticles. (Bershteyn A et al., *Soft Matter* 4: 1787, 2008.) These particles have a biodegradable poly(lactide-co-glycolide) core and a surface coating of a phospholipid bilayer (FIGS. 2A and B, arrows). These nanoparticles can encapsulate drug molecules in their core and/or incorporate drugs in the surface lipid bilayer, enabling sustained release of proteins, peptides, or small-molecule compounds. Nanoparticles were synthesized by a double emulsion/solvent evaporation process: 200 µL water was emulsified in 1 mL chloroform containing 2 mg of a lipid mixture (4:1 mole:mole DOPC: DOPG with varying quantities of dioleoyl maleimidophenyl phosphoethanolamine (MPB PE), with or without 25 µg 1,1'-dioctadecyl-3,3,3',3'-tetramethylindodicarbocyanine (DiD) or DiR lipid-like fluorescent dye (Invitrogen)) and 30 mg poly(lactide-co-glycolide) (PLGA, 50:50 wt:wt lactide:glycolide, 13 KDa, Lakeshore biopolymers). Inclusion of the maleimide-headgroup MPB PE lipid in the lipid fraction enables cell conjugation, as described below. The resulting water-in-oil emulsion was sonicated on ice (1 min, 7 Watts with a Misonix Microson XL probe tip sonicator) then added to 6 mL deionized water on ice with sonication (5 min, 12 Watts), forming a water-in oil-in water double emulsion. Chloroform was evaporated from the double emulsion by stirring at 20° C. under atmospheric pressure for 6 hrs to form solid nanoparticles. During solvent evaporation, the lipids in the organic phase self-assemble at the oil-water interface and form a bilayer coating around the nascent PLGA-core particles (FIGS. 2A and B); excess lipid is also present in the particle bulk. The particles were purified from free lipid by centrifugation through a 60 wt % sucrose cushion, dialyzed to remove sucrose, and stored at 4° C. (short term storage) or lyophilized in the presence of trehalose and stored at 4° C. until used. Simple variations in the processing conditions (e.g., use of homogenization instead of sonication) allowed particles of different size to be prepared, as determined by dynamic light scattering (DLS, data not shown).

To synthesize DNA-gel nanoparticles, we first generated four-armed DNA junctions, X-DNA monomers, by annealing the following oligonucleotides (Integrated DNA Technology, IDT):

1)
                                               (SEQ ID NO: 2)
5'-p- ACGTCGACCGATGAATAGCGGTCAGATCCGTACCTACTCG-3'

2)
                                               (SEQ ID NO: 3)
5'-p- ACGTCGAGTAGGTACGGATCTGCGTATTGCGAACGACTCG-3'

3)
                                               (SEQ ID NO: 4)
5'-p- ACGTCGAGTCGTTCGCAATACGGCTGTACGTATGGTCTCG-3'

4)
                                               (SEQ ID NO: 5)
5'-p- ACGTCGAGACCATACGTACAGCACCGCTATTCATCGGTCG-3'

These oligos self-assemble into three-dimensional "X" nanostructures with complementary overhangs at the end or each arm. As recently described (Um et al., Nat Mater, 5:797, 2006), addition of ligase to a solution of these DNA macromers leads to covalent crosslinking and the formation of DNA-base hydrogels. To form nanoparticles, 1.667 mg X-DNA monomer was then admixed to 6.7 µl T4 DNA ligase (3 Weiss units/µl, Promega), 20 µl T4 ligase buffer (Promega) and nuclease-free water (IDT) to a total volume of 200 µl, which was subsequently vortexed with a dry lipid film containing 0.396 mg DOPC, 0.101 mg DOPG, 0.63 mg MPB and 0.04 mg DiD. The resulting DNA gel-lipid mixture was sonicated on ice (5 min total, alternating power cycles of 1 W and 5 Watts every 30 s with a Misonix Microson XL probe tip sonicator), and extruded 21 times through a polycarbonate filter (200 nm pore size, Whatman). Following a 3 hour incubation at 25° C. and overnight incubation at 4° C. to allow ligase-mediated X-DNA crosslinking, 4 µl Exonuclease III (New England Biolabs), 20 µl Buffer 1 (New England Biolabs) and nuclease-free water to a total volume of 200 µl was were added and incubated at 37° C. for 90 minutes. DNA-gel nanoparticles were purified from free lipids and DNA by centrifugation through a 10 wt % sucrose cushion, and washed three times with nuclease-free water. A typical yield of $10^{10}$ DNA gel nanoparticles in the 200-250 nm diameter range was measured using a 90Plus Particles Size Analyzer (Brookhaven Instruments).

For IL-15Sa/IL-21 encapsulation in DNA-gel nanoparticles, 30 µg recombinant mouse IL-15Rα/Fc chimera (R&D systems) was precomplexed with 10 µg mouse IL-15 (Peprotech) in nuclease-free water for 1 hour at room temperature to generate superagonist IL-15 (IL-15Sa), combined with 10 µg mouse IL-21 (Peprotech) and blended with the X-DNA/T4 ligase mixture for DNA-gel particle synthesis, following the procedure described above.

For DNA-gel nanoparticle loading with the GSK3-β inhibitor TWS119 (Cayman Chemical), 1 mg TWS was resuspended in 250 µl DMSO, before adding it to the X-DNA/T4 ligase mixture for DNA-gel particle synthesis.

Figure 2C:
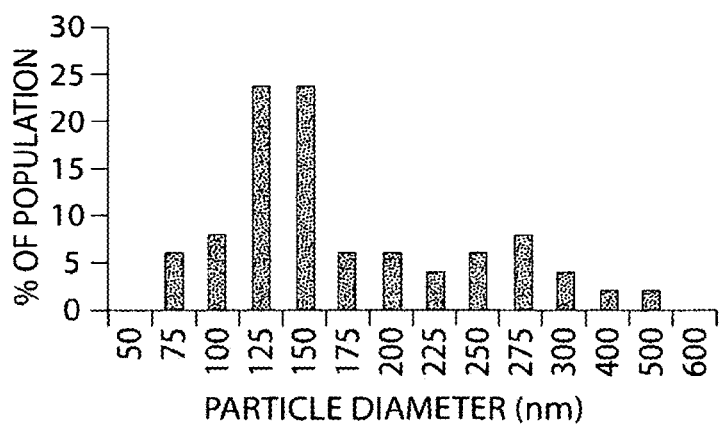

1.2. Nanoparticle Characterization. Characterization of the nanoparticles by DLS and cryoelectron microscopy showed that the mean particle diameter obtained from this process is 161±74 nm (FIG. 2C). Labeling of PLGA-core or liposome nanoparticles with lipid-like dyes such as carbocyanine dyes (DiD, Invitrogen) allowed the particles to be easily detected in confocal microscopy or flow cytometry analysis of particle-decorated cells (illustrated in the data discussed below).

1.3. TCR-Transgenic System for Modeling Adoptive Cell Therapy in Murine Melanoma. To develop and test the concepts proposed here, we used the pmel-1 TCR-transgenic mouse/B16F10 murine melanoma system developed at the NCI as a model of adoptive cell therapy for melanoma. Pmel-1 CD8+ T cells express a T cell receptor which recognizes a peptide from murine gp100, a melanoma self-antigen expressed by B16 melanoma tumor cells that is also used as a T cell target in human melanoma vaccines. (Overwijk et al., J Exp Med 198(4): 569, 2003; Klebanoff et al., Proc Natl Acad Sci USA 102(27): 9571, 2005; Overwijk et al., J Exp Med 188(2): 277, 1998.) Pmel-1 mice develop T cells tolerized to this antigen, mimicking what is thought to be a common situation in the immune response to human cancers, although these cells can be activated and expanded by priming them with an altered peptide ligand, a peptide from human gp100. (Overwijk et al., J Exp Med 198(4): 569, 2003.) This model serves as a mimic of human ACT where tolerance must be broken to fully prime the immune response following adoptive transfer of expanded T cells into recipient tumor-bearing mice.

1.4. Coupling of Nanoparticles to Live T Cells Through Free Surface Thiols.

Having developed a strategy for preparation of lipid-coated particles, we next performed a number of studies using 'blank' nanoparticles (no encapsulated cytokine/TLR ligand compounds) to evaluate the prospects of this approach. We first tested whether nanoparticles could be simply adsorbed to T cell surfaces stably, by incubating cells with nanoparticles at varying particle:cell ratios for different durations at 4° C. or 37° C. Though PLGA-core nanoparticles could be adsorbed to cells (in varying quantities, depending on the surface charge of the nanoparticles used), we found that in some instances physical adsorption did not provide very stable binding to the cells, and an increasing fraction of nanoparticles was removed from the cells during repeated washing as assessed by flow cytometry analysis of tagged cells (not shown). It is to be understood however that in some embodiments linkage of nanoparticles to carrier cells through non-covalent absorption may be sufficient for the particular application. This may be useful for example in the delivery of antigen-loaded nanoparticles that may be transferred to antigen presenting cells in lymphoid organs after administration and appropriate homing.

To obtain more stable binding of particles to T cells, we developed a non-toxic strategy to covalently link the lipid-coated nanoparticles to T cells. We exploited the substantial amounts of free thiols available on cell-surface proteins of leukocytes. (Sahaf et al., Proc Natl Acad Sci USA 100(7): 4001, 2003.) We conjugated maleimide-functionalized dyes (which react with thiols to form stable thioether linkages) to freshly-isolated T cells and analyzed the cells by flow cytometry. T cells, B cells and hematopoietic progenitor cells (e.g., murine $Lin^-$, $Sca-1^+$, $c-kit^+$ cells) were found to have high levels of free thiols at the cell surface, though red blood cells did not (not shown).

Figure 2D:
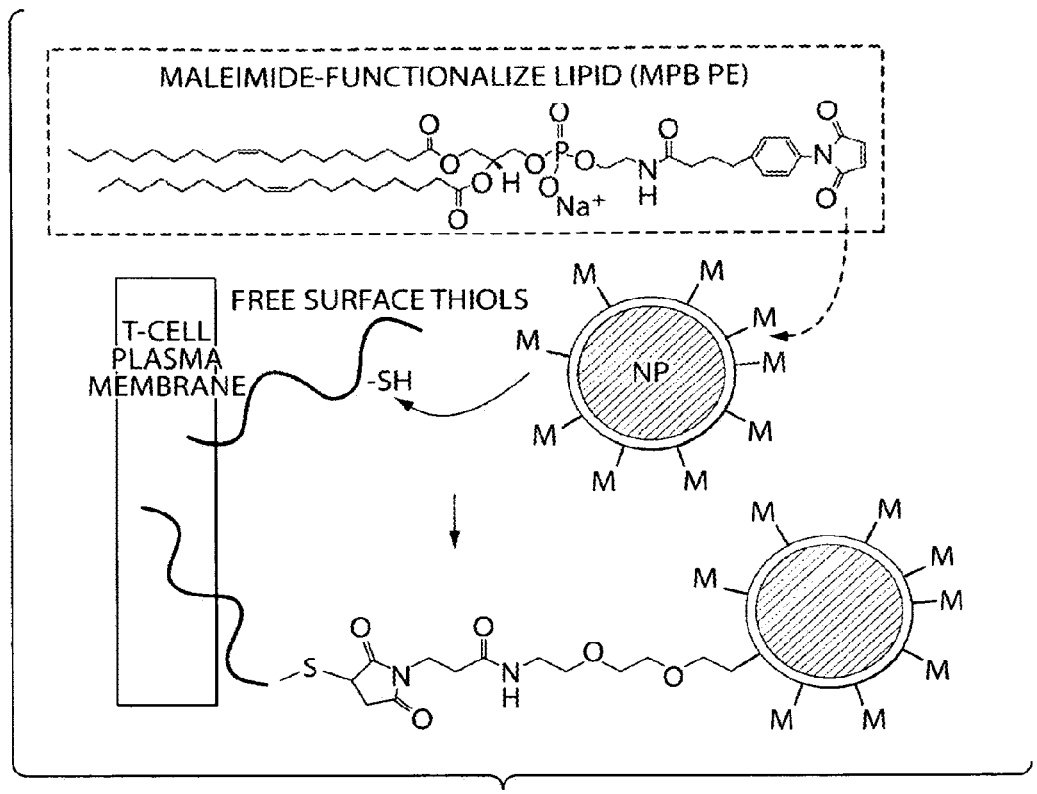

Based on these results, we developed the strategy outlined in FIG. 2D. Nanoparticle carriers were prepared which included lipids with maleimide-terminated headgroups. $CD8^+$ T cells were isolated from spleens of pmel-1 TCR-transgenic using magnetic bead negative selection (Miltenyi Biotec) and expanded for 4 days in vitro using anti-CD3/anti-CD28-coated beads in the presence of 200 IU/mL human IL-2, mimicking the preparation of tumor-specific T cells for adoptive cell therapy. T cells were washed and incubated ($60 \times 10^6$ cells/mL) with maleimide-functionalized-nanoparticles (at varying concentrations) at 37° C. for 45 min at varying particle:cell ratios. Cells were then separated from unbound particles by gentle centrifugation. Residual maleimide groups present on particles bound to the T cells were quenched by incubation of the cells ($3 \times 10^6$/mL) with 1 mg/mL thiol-terminated 2 KDa poly(ethylene glycol) (PEG, Laysan Bio) at 37° C. for 30 min in complete RPMI medium, followed by two washes to remove unbound PEG. By varying the amount of maleimide-lipid incorporated, we found that 50 mole % maleimide in the lipid fraction provided optimal binding to T cells and retention of particles through multiple washes (not shown).

Figure 3A:
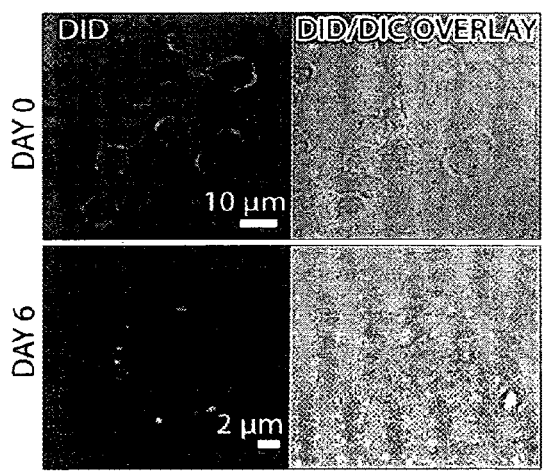
FIGS. 3A-B. Maleimide-functionalized nanoparticles stably link to the surface of T cells without toxicity. Pmel-1 CD8$^+$ T cells were incubated with 2500 fluorescent DiD-labeled nanoparticles per cell for conjugation, washed, and cultured for 6 days in the presence of IL-2. (A) Confocal microscopy of live cells on day 0 and day 6, showing nanoparticle fluorescence (purple). (B) Viability of particle-conjugated or control T cells assessed by annexin V and propidium iodide staining followed by flow cytometry analysis.
Figure 3B:
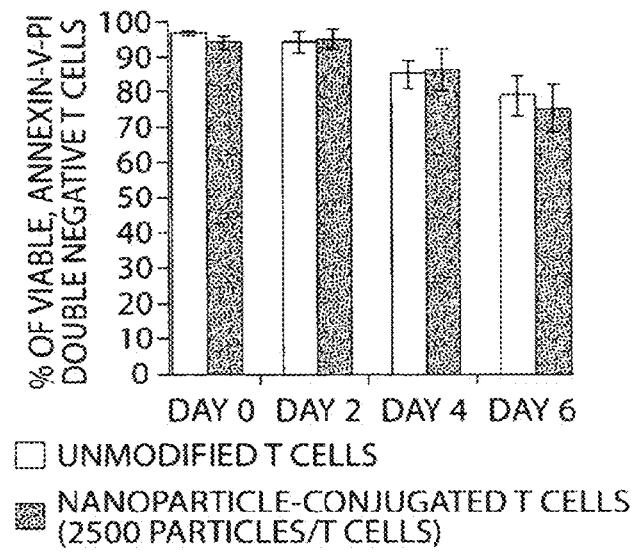

As shown in FIG. 3A, nanoparticles were readily attached to cells using this thiol-reaction strategy. 2500 nanoparticles per cell during conjugation as shown in FIG. 3 gave ~500 nanoparticles bound per cell as determined from particle counting at high magnification in confocal microscopy; this corresponds to a theoretical occlusion of ~3.2% of the average T cell surface area by 160 nm diameter particles. T cells cultured in IL-2 showed a dilution of the density of nanoparticles bound to the cells over the course of a week, due to proliferation of the cells (FIG. 3A, day 6). Conjugation of nanoparticles to cells at this density led to no loss of T cell viability over a week in culture (FIG. 3B), and also did not trigger spontaneous activation of these cells.

A key issue for these studies was the localization of the particles. If the cells internalize these particles then encapsulated drug cargos may not be released into the local microenvironment and/or drugs released from the nanoparticles may be unable to access their target receptors on the T cell itself. Importantly, we found that T cells do not internalize lipid-coated PLGA nanoparticles (illustrated by FIG. 3A), even during extended culture or following proliferation (discussed further below). This is in stark contrast to what we observed with dendritic cells, which phagocytosed the attached nanoparticles within minutes.

Example 2

Figure 4A:
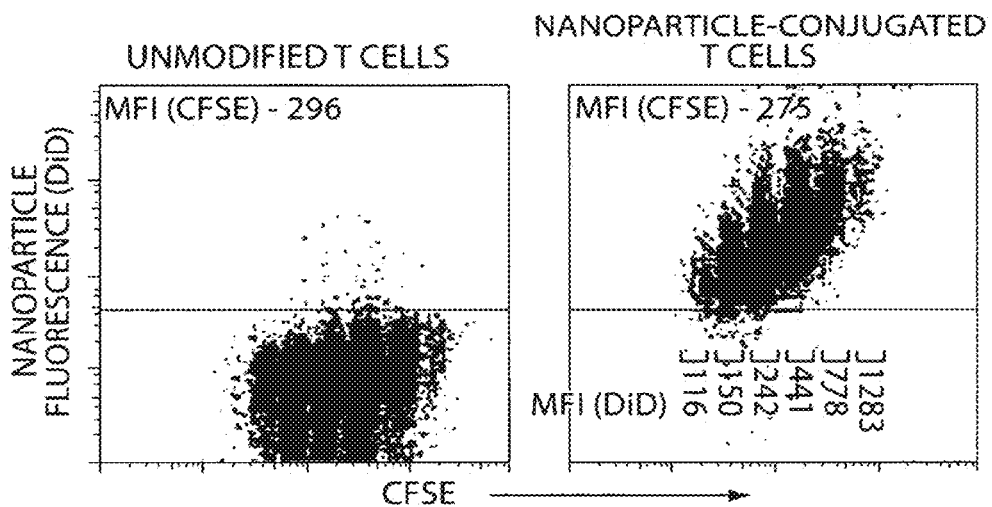
FIGS. 4A-C. Nanoparticles conjugated via thiols to T cell surfaces do not inhibit T cell proliferation, cytokine production, or target cell killing. (A, B) DiD-labeled PLGA-core nanoparticles were attached to CFSE-labeled pmel-1 CD8$^+$ T cells (2500 nanoparticles/cell), then particle-conjugated T cells (bottom panel) or control 'bare' T cells (top panel) were stimulated with mature hgp100 peptide-pulsed bone marrow-derived dendritic cells at a 2:1 T cell:DC ratio; cultures were supplemented with IL-2 every 2 days. (A) The cells were analyzed by flow cytometry on day 6: Scatter plots of DiD (nanoparticle label) vs. CFSE fluorescence gated on live CD8$^+$ cells are shown in the upper panel, and the corresponding mean nanoparticle fluorescence as a function of the number of cell divisions determined from CFSE are shown in the right panel. (B) Cytokines secreted by nanoparticle-conjugated T cells (●) or 'bare' T cells (○) were measured by ELISA on sups collected at 24 hrs (IL-2) or 48 hrs (IFN-γ and TNF-α). (C) Pmel-1 T cell blasts were conjugated with 2500 nanoparticles/cell or left unmodified, and co-cultured with hgp100 antigen-pulsed (Mingozzi F et al., Nat Med 13(4): 419, 2007) Cr-labeled EL4 target cells or unpulsed control EL4 cells, and the % of specific target cell killing was quantified by measuring (Mingozzi F et al., Nat Med 13(4): 419, 2007) Cr release after 4 hrs for varying pmel-1 effector cell:target cell ratios.

Assessment of Nanoparticle Binding on T Cell Functions 2.1. Nanoparticles Bound to Cells Do Not Block Antigen Recognition or T Cell Proliferation. Having found that thiol coupling allowed stable non-toxic linkage of nanoparticles to cells, we next sought to determine whether the coupling reaction interfered with T cell behavior, and to find what dose of nanoparticles could be attached to T cells without blocking key T cell functions. We first tested whether T cell proliferation was impacted by nanoparticle coupling. Pmel-1 T cells were primed/expanded in vitro with anti-CD3/anti-CD28 beads and IL-2 as described above. The expanded cells were labeled with carboxyfluorescein succinimidyl ester (CFSE), and incubated with 2500 DiD-labeled lipid-coated PLGA nanoparticles per cell for conjugation. In parallel, day 6 bone marrow-derived dendritic cells from C57Bl/6 mice prepared as described (Stachowiak et al., J Immunol 177(4): 2340, 2006) were activated by incubation with 1 µM CpG oligonucleotide (a ligand for TLR 9) and pulsed with 1 µM $hgp100_{25-33}$ peptide (a peptide recognized by pmel-1 T cells in the context of $H-2D^b$ MHC I molecules) overnight. Nanoparticle-conjugated or control 'bare' T cells were co-cultured with activated antigen-loaded DCs at a 2:1 T:DC ratio for 6 days, and then analyzed by flow cytometry. As shown in FIG. 4A, the degree of proliferation of control and nanoparticle-conjugated T cells as determined by CFSE dilution in the dividing cells was indistinguishable. In addition, analysis of the mean fluorescence from nanoparticles bound to cells showed a steady decline in nanoparticle fluorescence as the number of cell divisions increased, reflecting segregation of particles to separate daughter cells during division. Notably, when sorted CFSE-low divided cells were examined in confocal microscopy, nanoparticles were found to still be surface localized even on cells that had undergone 5 cell divisions.

Figure 4B:
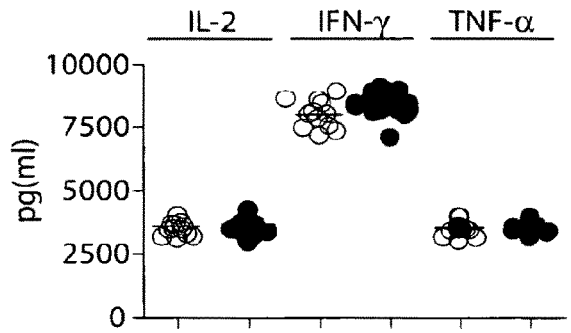

2.2. High Densities of Nanoparticles Can Be Bound to T Cells Without Inhibiting Cytokine Secretion or CTL Activity. Activated $CD8^+$ T cells secrete cytokines such as IFN-γ and TNF-α and directly kill antigen-bearing target cells as part of their anti-tumor activity. To determine whether conjugation of lipid-coated PLGA nanoparticles to T cells interferes with cytokine secretion, particle-conjugated or control T cells were co-cultured with antigen-pulsed DCs as described above, and the production of several key cytokines by the T cells was assessed by ELISA. As shown in FIG. 4B, pmel-1 T cells decorated with nanoparticles produced equivalent amounts of IL-2, IFN-γ and TNF-α in response to antigen stimulation as unmodified 'bare' T cells. Thus, substantial quantities of nanoparticles can be bound to cells without blocking effector cytokine secretion.

Figure 4C:
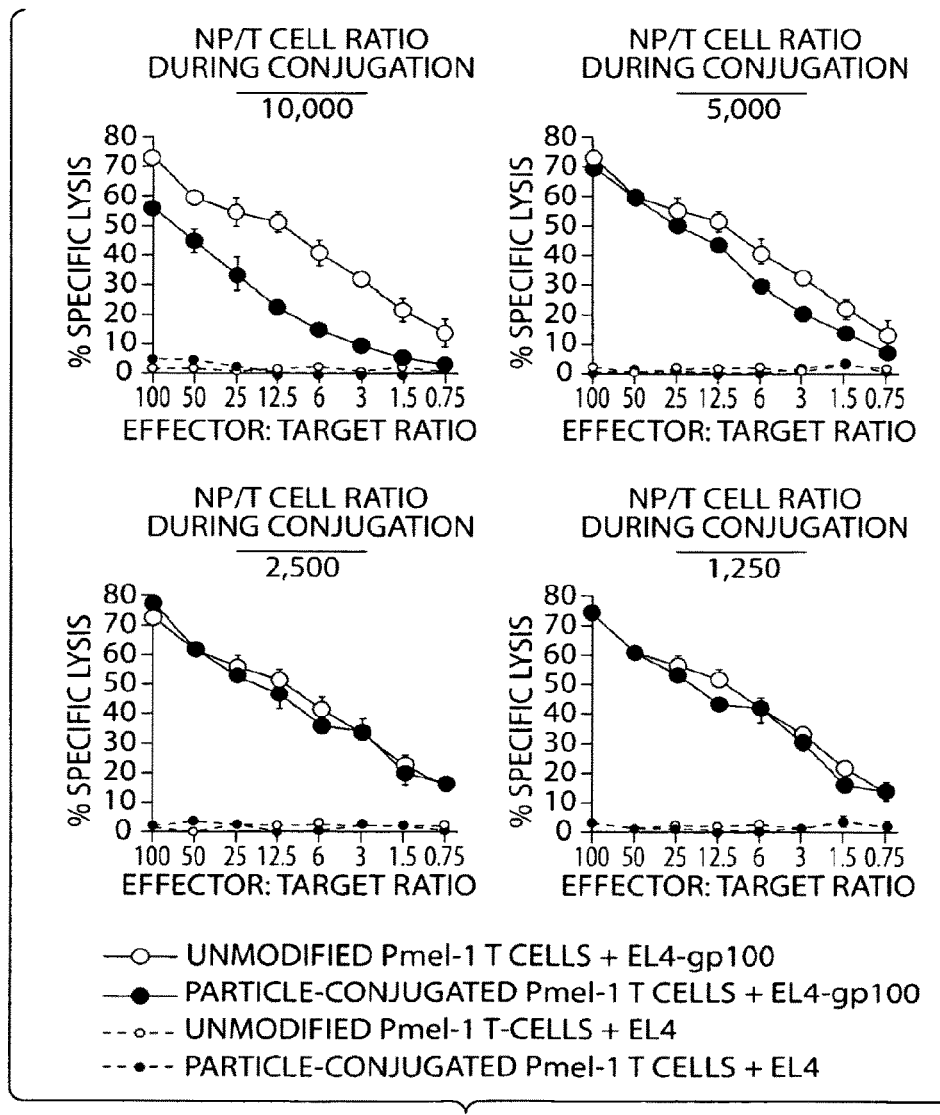

We next carried out a dose response analysis to determine the maximal dose of nanoparticles could be attached to T cells without inhibiting cytolytic activity of the lymphocytes. Pmel-1 T cells were expanded in vitro as before, and then incubated with varying doses of lipid-coated PLGA nanoparticles per cell ranging from 100 nanoparticles/cell up to 10,000 nanoparticles per cell for particle conjugation. Particle-tagged or control T cells were then co-cultured with $^{51}$Cr-labeled EL4 target cells pulsed with hgp100$_{25-33}$ peptide at varying effector:target ratios for 4 hrs at 37° C. in complete medium. Specific target cell lysis was determined by measurement of radioactive chromium released into the culture supernatant. As shown in FIG. 4C, target cell killing by nanoparticle-conjugated T cells was indistinguishable from control T cells except at the two highest coupling doses tested (10,000 or 5000 nanoparticles/cell).

2.3. TCR-Transgenic OT-1 CD8+ T Cell Analysis. Similar results were found with other T cells. TCR-transgenic OT-1 CD8$^{+}$ T cells, which are specific for a peptide derived from ovalbumin, and which were conjugated with up to 100 (±21) nanoparticles per cell, fully retained their physiological proliferative response after co-culture with ovalbumin-pulsed target dendritic cells. In some instances, higher surface densities of the same nanoparticles began to inhibit T cell proliferation (data not shown). During cell division, surface-attached nanoparticles segregated equally to daughter cells, which was reflected by a stepwise decrease in the mean fluorescent signal from cell-conjugated nanoparticles with increasing number of cell divisions (data not shown). Attachment of up to ~100 particles/cell also did not impact T cell recognition/killing of ovalbumin peptide-pulsed target cells or cytokine release profiles (data not shown).

In summary, for conditions of up to 2500 nanoparticles/cell during conjugation (nanoparticles with diameters ~160 nm), no inhibition of T cell antigen recognition, proliferation, cytokine secretion, or target cell killing is observed. These results together suggest that substantial quantities of submicron-sized nanoparticles can be attached to T cells without blocking key cell functions.

Example 3

Cytokine/Drug Loading in Lipid-Coated PLGA Nanoparticles

Nanoparticles are conjugated to ACT T cells in two different ways: (i) nanoparticles are loaded with cytokines designed to act on the carrier T cells themselves to support their proliferation, survival and effector function (e.g., IL-15 superagonist) or (ii) nanoparticles will be used to deliver compounds designed to act on other cells in the microenvironment, including Toll-like receptor (TLR) ligands and vaccine antigens (e.g., imiquimod or MPLA). In the previous studies, 'empty' nanoparticles were used to assess the impact of particle conjugation on T cell functions. Here we tested the encapsulation/incorporation of proteins (e.g., IL-15 superagonist) and TLR ligands into the nanoparticles, in order to deliver therapeutically relevant cargos.

Figure 5A:
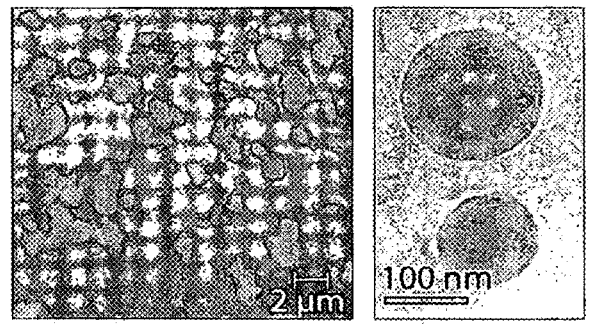
FIGS. 5A-C. Protein and TLR ligand incorporation in lipid-coated PLGA nanoparticles. (A) Confocal image (left) and cryoEM image (right) of lipid-coated nanoparticles loaded with fluorescent ova in the particle cores. Note that the particles in the confocal image are artificially aggregated here by drying on a coverslip for imaging. (B) Kinetics of IL-15 release from lipid-coated PLGA particles in vitro in complete medium at 37° C. (C) Bone marrow-derived DCs were incubated with 3 mg/mL lipid-nanoparticles containing 1 mole % or 10 mole % MPLA in the lipid coating, equivalent amounts of soluble MPLA (30 μg/mL or 3 μg/mL), or soluble LPS (1 μg/mL) as a positive control. At 24 hrs, the maturation status of the cells was assessed by flow cytometry analysis of cell surface MHC II, CD80, and CD40 (not shown). Particle-MPLA was equivalent to or more potent than soluble MPLA in triggering DC maturation.
Figure 5B:
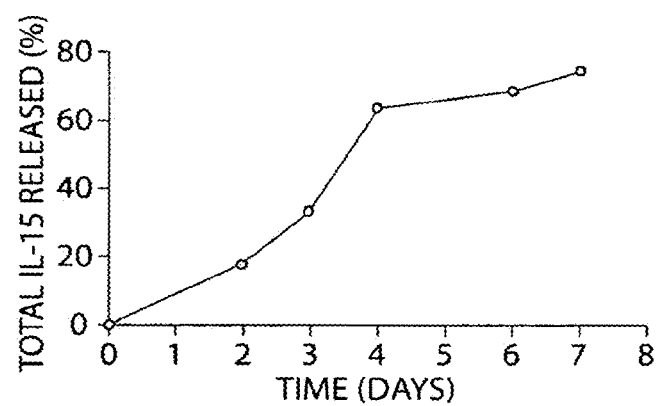

PLGA nanoparticles have been explored in numerous prior studies as vehicles for encapsulation and delivery of proteins, peptides, and small molecule drug compounds, and notably vaccine antigens/adjuvants. (Davis M E et al., Nat Rev Drug Discov 7(9): 771, 2008; Chacon M et al., International Journal of Pharmaceutics 141(1-2): 81, 1996; Diwan M et al., Curr Drug Deliv 1(4): 405, 2004; Elamanchili P et al., Vaccine 22(19): 2406, 2004; Li Y et al., J Control Release 71(2): 203, 2001; Zhang Z P et al., Biomaterials 28(10): 1889, 2007; Heit A et al., Eur J Immunol 37(8): 2063, 2007.) We first tested whether protein encapsulation was facile in our lipid-coated nanoparticles by adding protein to the inner aqueous phase of the double emulsion synthesis: 200 μL water in the synthesis protocol described in section 3.1 was replaced with 200 μL of a solution of the model protein Alexa488-labeled ovalbumin (100 μg in PBS), and particles were prepared and purified as before. As shown in FIG. 5A, ova fluorescence was clearly detected in nanoparticles by confocal microscopy, and cryoEM imaging of the nanoparticles showed that the particle morphology was not disrupted by protein encapsulation and the surface lipid layer was retained for protein-loaded particles (FIG. 5B). Measurement of the amount of protein encapsulated was performed by lysing the nanoparticles for 4 hrs in 0.02 M NaOH/2% SDS, neutralizing the solution with 0.2 M HCl, and measuring released ova fluorescence calibrated against ova solution standards exposed to the same base treatment conditions. By these measurements, we found that ~1 μg of ova per mg nanoparticles was encapsulated (~25% encapsulation efficiency).

Ova however is a model globular protein and as such it was chosen to illustrate the behavior of other proteins such as interleukin-15 (IL-15) superagonist molecules which can be used to support ACT T cells. We encapsulated IL-15 (cytokine alone) in lipid-coated PLGA to test the feasibility of cytokine loading in these particles. IL-15 (5 μg) in PBS was used in the inner aqueous phase of the particle synthesis, and the resulting cytokine-loaded particles were purified as described in section 3.1. The kinetics of IL-15 release from the particles was determined by incubating the particles in complete RPMI medium containing 10% FCS at 37° C. with gentle agitation and taking aliquots of the supernatant at staggered timepoints for ELISA analysis of cytokine content. As shown in FIG. 5B, ~80% of the encapsulated cytokine was released by the end of this incubation period. Other experiments with ova-loaded nanoparticles showed continuous release of protein over a similar 7-10-day period. Thus, the lipid-coated particles can be loaded with protein and release encapsulated material over a ~1 week period. The release kinetics can be modulated to faster or slower rates by altering the MW of the PLGA used in the particles.

Figure 6:
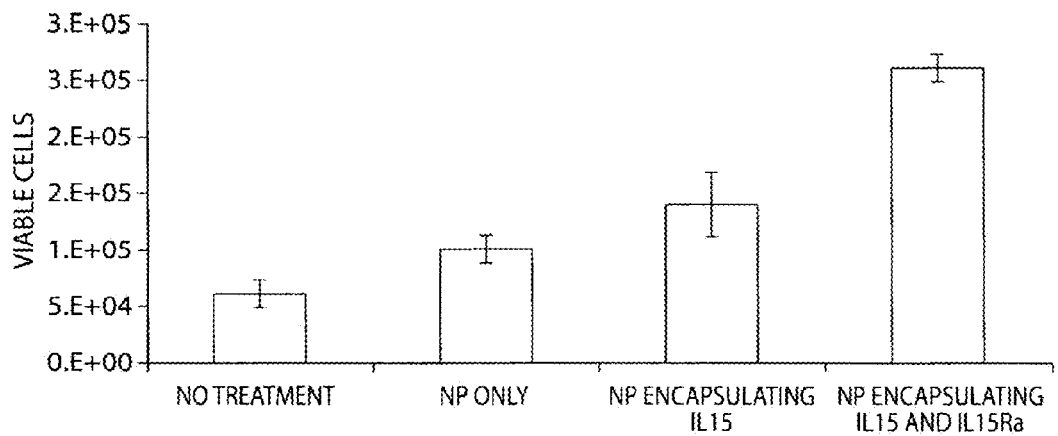
FIG. 6. Bioactivity of cytokine IL-15 released from cell-bound nanoparticles. T cells were conjugated with lipid-coated PLGA nanoparticles loaded with IL-15 or IL-15 complexed with soluble IL-15Ralpha-human Fc fusion protein (IL-15 superagonist). The number of viable T cells after 6 days in culture was assessed by cell counting after trypan blue staining. T cells carrying IL-15-loaded nanoparticles exhibited enhanced survival and/or proliferation.

Having found that cytokines can be successfully encapsulated and released from nanoparticles, we tested whether survival of T cells in vitro could be enhanced by cytokines released from nanoparticles. Pmel-1 T cells were primed/expanded in vitro with anti-CD3/anti-CD28 beads and IL-2 as described above. The expanded cells were incubated with 2500 lipid-coated PLGA nanoparticles per cells for conjugation. The nanoparticles were formulated with 10 mg of IL-15 or IL-15 and IL-15Rα. Particle-conjugated or control T cells were then co-cultured with EL4 target cells pulsed with hgp100$_{25-33}$ peptide at effector:target ratios of 20:1 at 37° C. in complete medium without exogenous IL-2 supplement. After 6 days of culture, the number of live T cells was counted after trypan blue staining to assess proliferation and survival of T cells. As shown in FIG. 6, nanoparticles encapsulating IL-15 and IL-15/IL-15Rα significantly enhanced survival and/or proliferation T cells compared to no treatment or empty nanoparticle groups. Proliferation observed in T cells tagged with cytokine-encapsulated nanoparticles was comparable to soluble IL15 and IL-15/IL-15Rα controls. Thus, IL-15 or its superagonist complexed with IL-15Rα continuously released from nanoparticles maintain its bioactivity and is able to support T cell survival and/or proliferation in vitro.

Nanoparticles were also loaded with the TLR4 ligand MPLA and/or the TLR7 ligand, imiquimod, as potent clinically-relevant ligands for driving DC activation during T cell adoptive therapy. MPLA is a synthetic lipopolysaccharide mimic that has shown promise as a nontoxic analog of the potent immunostimulant lipopolysaccharide (LPS). MPLA provides adjuvant activity in vaccines comparable to LPS but has orders of magnitude reduced systemic toxicity due to its selective engagement of downstream signals in the TLR4 signaling pathway. (Mata-Haro et al., Science 316(5831): 1628, 2007.) Notably, LPS and its derivatives have shown promise in breaking tolerance to tumors, and beneficial effects of whole-body irradiation observed during adoptive T cell therapy studies have been in part ascribed to LPS and other TLR signaling occurring when the integrity of the gut epithelium is compromised. (Yang et al., Nat Immunol 5(5): 508, 2004; Paulos et al., Clin Cancer Res 13(18 Pt 1): 5280, 2007; Paulos et al., J Clin Invest 117(8): 2197, 2007.)

Imiquimod, a small-molecule imidazoquinoline ligand for TLR7/8, is a promising pro-immunity factor for cancer therapy approved for clinical use as a topical cream in the treatment of certain skin cancers. In addition to its pro-immunity activation of macrophages and dendritic cells (Hemmi et al., Nat Immunol 3(2): 196, 2002), imiquimod has recently been reported to activate tumor-local dendritic cells to a direct tumor-killing phenotype in humans. (Stary et al., J Exp Med 204(6): 1441, 2007.)

Imiquimod and MPLA however share challenges in their application for cancer therapy. Systemic imiquimod delivered orally has shown dose-limiting toxicity in humans (Goldstein et al., J Infect Dis 178(3): 858, 1998) and has a short half-life following injection of only ~2 hrs (Soria et al., Int J Clin Pharmacol Ther 38(10): 476, 2000). Topical administration of imiquimod however has not been shown to be effective in systemic metastases or non-cutaneous cancers. Both TLR4 and TLR7 have broad expression patterns (expressed at low levels in endothelial cells and by epithelial cells (Fan et al., J Clin Invest 112(8): 1234, 2003; Gunzer et al., Blood 106(7): 2424, 2005)), raising concerns of systemic toxicity in prolonged treatment. TLR4 and TLR7 ligands however have been shown to induce expression of ICAM-1, ICAM-2, and selectins on endothelial cells (Gunzer et al., Blood 106(7): 2424, 2005), and such effects if locally stimulated at tumor sites could be used to enhance T cell trafficking into tumors. Thus, selective delivery of these ligands to tumor sites and secondary lymphoid organs might be used to enhance their anti-tumor activity while limiting systemic side effects.

Figure 5C:
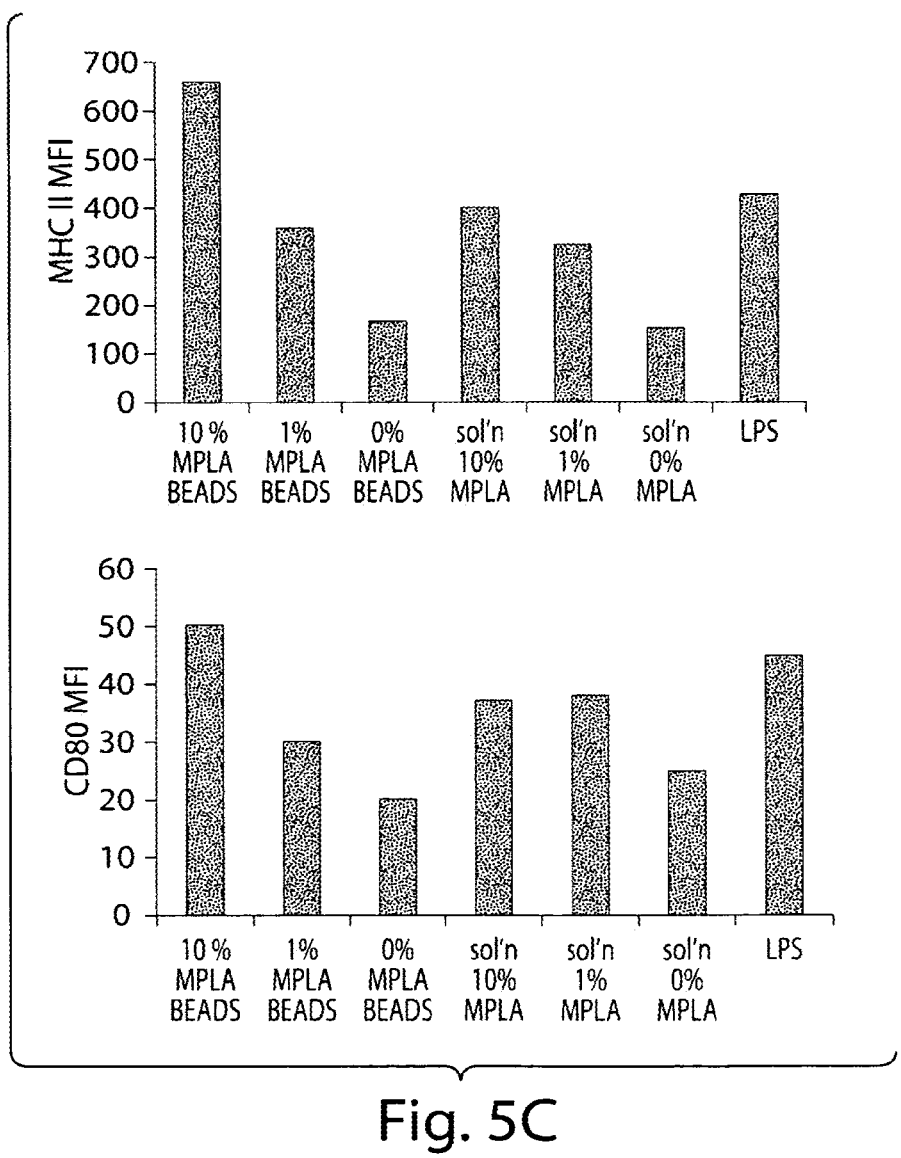

In parallel with protein encapsulation experiments, we thus also tested incorporation of the Toll-like receptor ligand monophosphoryl lipid A (MPLA) in lipid-coated PLGA. Due to its lipid-like structure, MPLA is quantitatively incorporated into the particles by simply co-dissolving this ligand with the other phospholipids in the chloroform phase of the particle synthesis. To test the ability of MPLA incorporated in lipid-coated PLGA nanoparticles to activate dendritic cells (which express the LPS receptor, TLR4), nanoparticles containing 1 mole % or 10 mole % MPLA as part of the lipid fraction of the synthesis were added to bone marrow-derived DCs for 24 hrs, and then the surface expression of class II MHC molecules and costimulatory receptors was analyzed by flow cytometry. DCs stained with antibodies against MHCII, CD80, and CD40 showed upregulation of these markers when treated with MPLA-containing nanoparticles comparable to DCs treated with 1 µg/mL LPS as a positive control; 'blank' nanoparticles however triggered no DC maturation (FIG. 5C). Thus, TLR ligands incorporated in the lipid-coated nanoparticles are capable of activating DCs.

Figure 7:
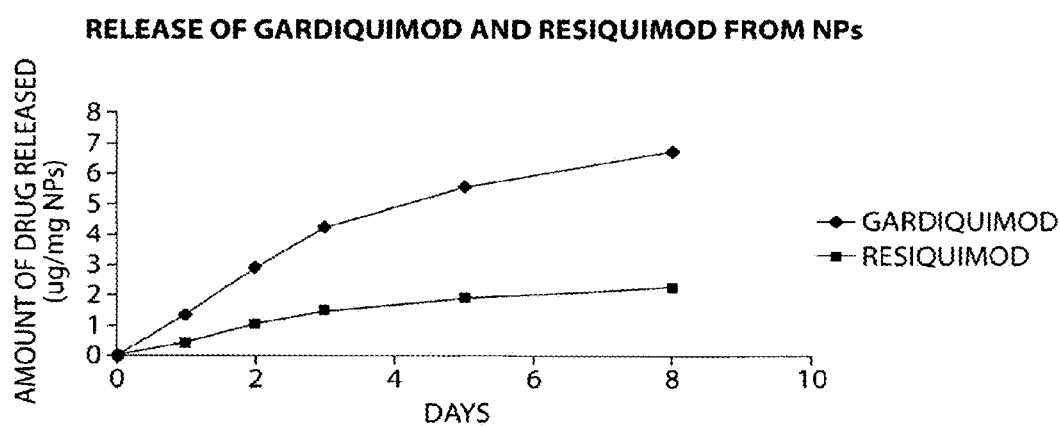
FIG. 7. Lipid-coated PLGA nanoparticles can encapsulate and then exhibit sustained release of TLR7/8 compounds. Toll-like receptor ligands gardiquimod or resiquimod were encapsulated in lipid-coated PLGA particles, and release into BSA-containing saline at 37° C. was assessed over 8 days, by measuring fluorescence of the released compounds.

Gardiquimod and resiquimod are imidazoquinoline derivatives that, similar to imiquimod, are selective ligands for TLR7/8. Gardiquimod and resiquimod have been suggested to have more potent effect than imiquimod, based on findings that they induce stronger cytokine production, macrophage activation, and enhanced cellular immunity (Wager et al., Cell Immunol 191(1):10, 1999; Burns et al., Clin Immunol 94(1):13, 2004; Schon et al., Oncogene 27(2): 109, 2008.) Encapsulation of gardiquimod and resiquimod and detection of their release from PLGA nanoparticles were carried out with minor modifications. For encapsulation of gardiquimod in nanoparticles, 200 µL water in the synthesis protocol described in section 3.1 was replaced with 1.8 mg of gardiquimod dissolved in 200 µL of water, and for encapsulation of resiquimod, 0.83 mg of resiquimod was dissolved along with 30 mg of PLGA in organic solvent; the rest of nanoparticle synthesis protocol outlined in section 3.1 was followed thereafter. The kinetics of drug release from the particles was determined by incubating the particles in water with gentle agitation at room temperature and taking aliquots of the supernatant at staggered timepoints for fluorescent detection of drug release at excitation/emission of 260/340 nm. As shown in FIG. 7, continuous release of gardiquimod and resiquimod from nanoparticles was observed over 8 days of incubation.

Example 4

Figure 8A:
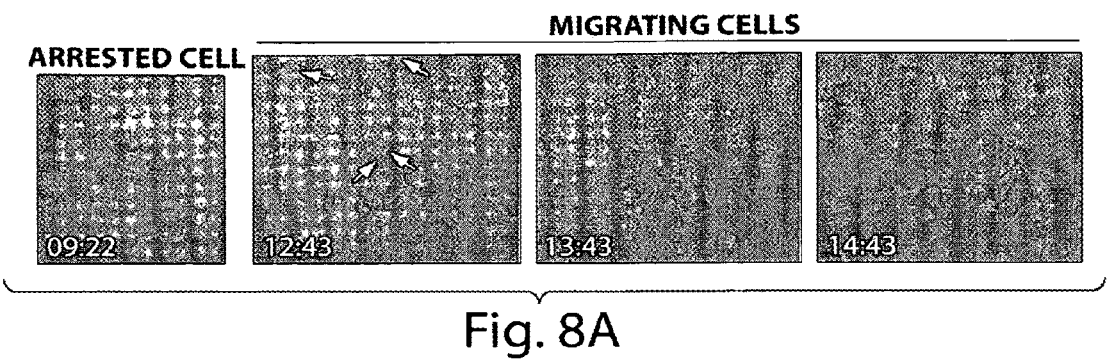
FIGS. 8A-D. Whole-animal bioluminescence/fluorescence imaging of nanoparticles, nanoparticle-conjugated T cells, and B16 melanoma tumor models. (A) T cells polarize surface-bound nanoparticles (red fluorescence) to the uropod during migration. Primed T cells were conjugated with nanoparticles and then observed migrating on glass coverslips by time-lapse fluorescence videomicroscopy. Migrating cells clustered the nanoparticles to the uropod (arrows in first frame denote direction of migrating cells). Cells that halted and de-polarized even momentarily redistributed the nanoparticles over the cell surface, indicating a lack of aggregation among nanoparticles. (B) DiR-labeled nanoparticles (1 mg) were injected s.c. in the flank of an anesthetized mouse and imaged by whole-animal fluorescence (shown in false color on the right flank). (C) Bioluminescence imaging of gaussialuciferase-tagged nanoparticles attached to $4 \times 10^6$ pmel-1 T cells, 4 hrs after tail vein injection of particle-conjugated T cells. Red arrows denote T cells accumulated in lungs, while white arrows highlight what may represent T cell homing to axillary lymph nodes. (D) Bioluminescence imaging of Gaussia-luciferase-expressing B16F10 melanoma cells, illustrating metastasis 14 days following kidney capsule injection.

Whole Animal Imaging Reagents for Independently Tracking Tumor Cells, Nanoparticles, and T Cells In Vivo The data described in the previous two sections demonstrate the protocol we have developed to attach nanoparticles to T cells in a nontoxic manner that does not interfere with key T cell functions. The particles can be loaded with protein or TLR ligands as therapeutic cargos that will be explored in the proposed research. A final key function that nanoparticle conjugation must not interrupt is migration/tissue homing of T cells. We first tested in vitro migration of particle-conjugated T cell blasts plated on glass coverslips. As shown in FIG. 8A, migrating T cells observed in time-lapse videomicroscopy polarized cell-surface-bound nanoparticles to the uropod during migration, but when cells halted migration, the particles re-dispersed over the cell surface ('arrested cell'). Thus, particle-conjugated cells are able to migrate and rearward polarization of the nanoparticles during motility may help reduce the likelihood that the particles will interfere with the patrolling function of these cells in vivo.

We next assessed the impact of cell surface-tethered nanoparticles on the ability of their cellular carrier to transmigrate across endothelial barriers, as a measure of the ability of the cell carrier to infiltrate its target tissue. We utilized an in vitro transwell co-culture system in which unmanipulated or nanoparticle-conjugated effector T lymphocytes migrate from the upper chamber across a membrane-supported confluent TNF-α activated endothelial monolayer towards in response to a T cell chemoattractant placed in the lower chamber. Unaltered T cells carrying 100 nanoparticles/cell exhibited unaltered transmigration efficiencies compared to unmodified cells (data not shown). After crossing the endothelial barrier, T lymphocytes still had retained 83% (±3%) of the original nanoparticle cargo physically attached. Confocal imaging revealed that T cells migrating on the endothelial layer polarized to a characteristic "hand-mirror" morphology, and localized their nanoparticle pool to the uropod (data not shown), likely reflecting the uropodal localization of many cell surface proteins on migrating T cells.

Further experiments were conducted to show that particle-conjugated T cells can home to their expected tissue sites, and for therapy that such cells can enter solid tumors as effectively as unmodified T cells. To aid in these studies, we use multi-color bioluminescence/fluorescence whole-animal imaging to simultaneously track the location of nanoparticles, adoptively-transferred T cells, and tumor cells. These experiments are performed using a Xenogen IVIS Spectrum bioluminescence/fluorescence imaging instrument located in the Koch Cancer Institute core facilities at MIT.

Figure 8B:
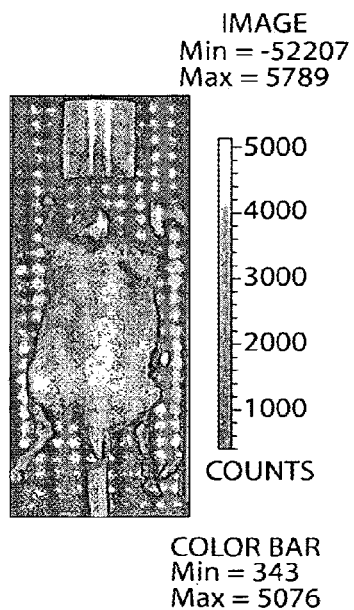
Figure 8C:
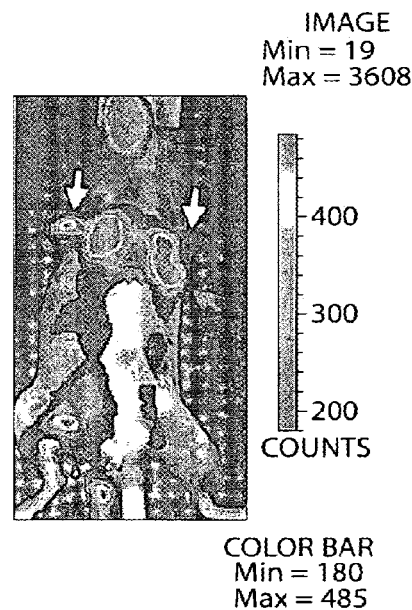

As shown in FIG. 8B, lipid-coated PLGA nanoparticles labeled with DiR dye are readily detected in whole-animal fluorescence following subcutaneous injection, due to the low absorption of near-IR excitation light used for this dye (exc 750 nm/em 790 nm). In an in vivo homing experiment, nanoparticles with surface-conjugated recombinant Gaussia luciferase were prepared. Pmel-1 T cells were then coupled with these luciferase-decorated nanoparticles and injected i.v. (via tail vein) into a recipient C57Bl/6 mouse. Whole-animal bioluminescence imaging following the injection of the Gaussia luciferase substrate coelentarizine 4 hrs after T cell transfer via tail vein injection is shown in FIG. 8C. At this timepoint, a majority of T cells are still localized in the lungs as previously reported for effector T cells (Hamann A et al., Eur J Immunol 30(11): 3207, 2000) but nanoparticle/T cell signatures were also detected at flank sites that may reflect homing to inguinal lymph nodes and small intense spots of bioluminescence were detected next to the lungs (white arrows) that may reflect initial homing to axillary/brachial lymph nodes.

Figure 8D:
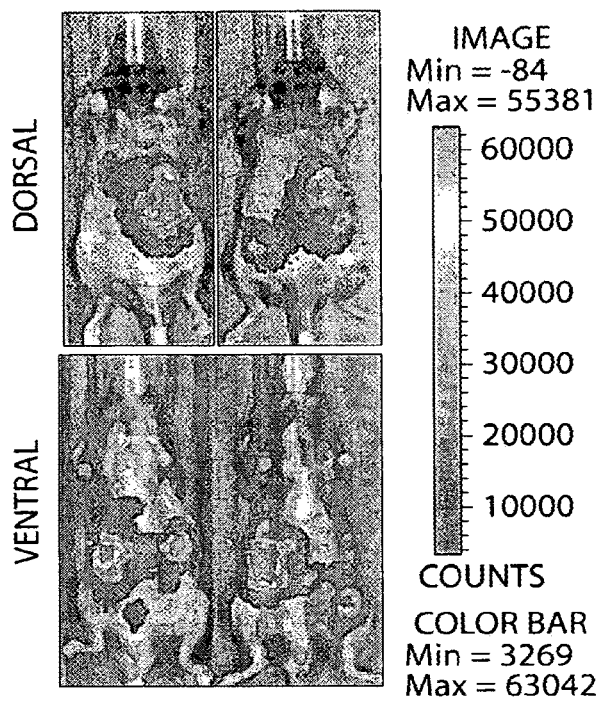

Because the nanoparticles can be tracked using near-IR dyes and fluorescence, we crossed pmel-1 TCR-transgenic mice with luciferase-transgenic mice, to obtain pmel-1-luc mice where the pmel-1 $CD8^+$ T cells express firefly luciferase (data not shown). In parallel, Gaussia-luciferase-expressing B16F10 melanoma cells were prepared by retroviral transfection of B16 cells with a luciferase construct. As illustrated in FIG. 8D, the B16-gaussia luc cells were readily detected via bioluminescence imaging.

Figure 9A:
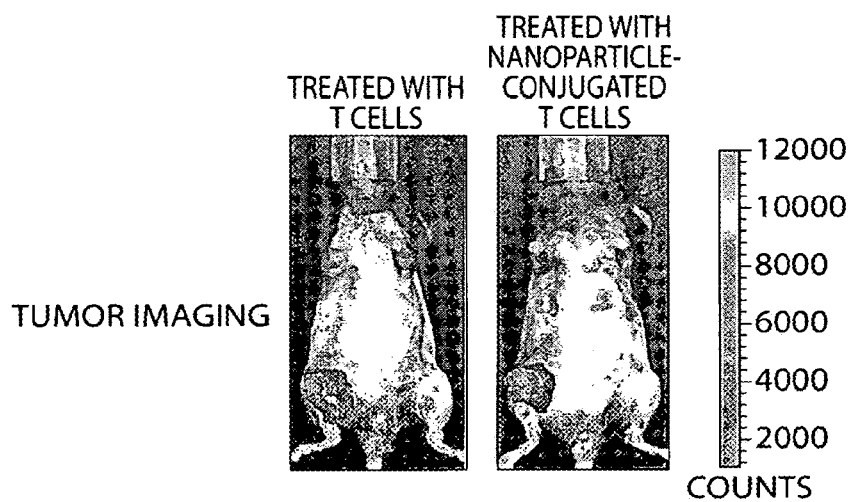
FIGS. 9A-D. Melanoma-targeting Pmel-1 T lymphocytes vehicle surface-conjugated nanoparticles into the tumor microenvironment. (A-D) 500,000 B16F10 tumor cells, transduced with Gaussia luciferase, were injected into the right femur of C57BL/6 mice. After three weeks, tumor burden was visualized by IVIS imaging (A). Animals were treated with $15 \times 10^6$ effector Pmel-1 T lymphocytes, transgenic for Firefly luciferase (A-D, left panel), or effector Pmel-1 T cells conjugated with nanoparticles containing the fluorescent tag DiD (A-D, right panel). Before adoptive transfer, T lymphocytes were incubated with 1 mg/ml Thiol-PEG for 30 min to avoid non-specific uptake of surface-bound nanoparticles by macrophages. Four days after T cell treatment, the biodistribution of adoptively transferred Pmel-1 T cells was imaged with bioluminescence (B), surface-bound nanoparticles were tracked by fluorescent IVIS imaging for DiD (C). The right femurs were flushed and analyzed by multicolor flow cytometry for T cell infiltrates (Thy1.1) and DiD nanoparticles (D).
Figure 9B:
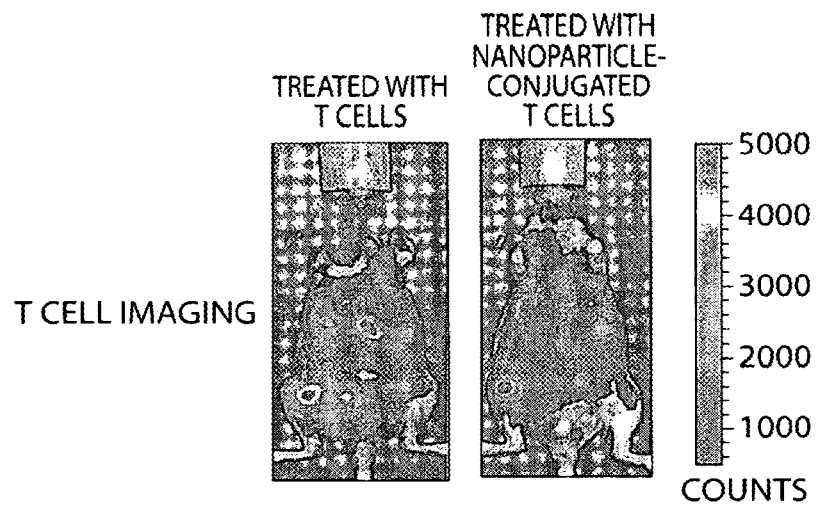
Figure 9C:
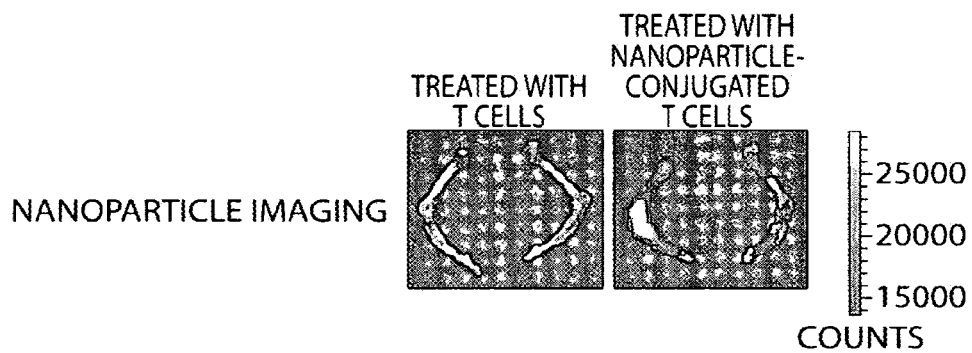
Figure 9D:
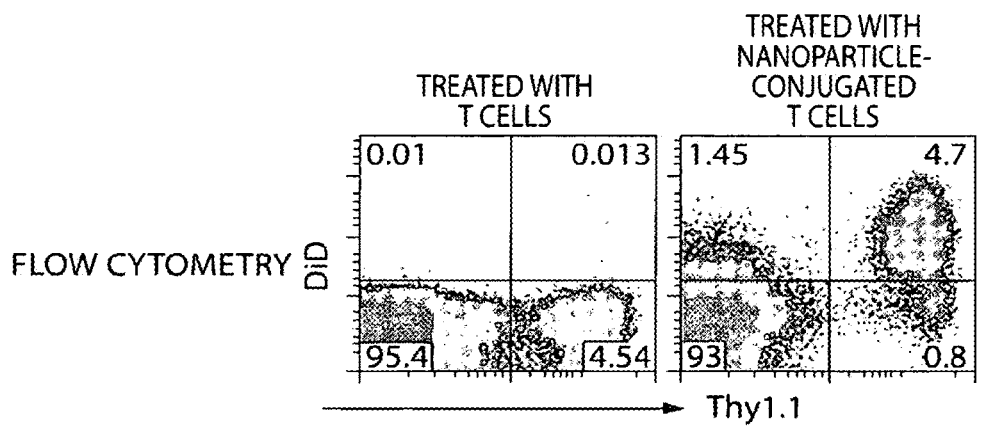

To assess the potential of tumor-reactive T lymphocytes to vehicle surface-conjugated nanoparticles into the microenvironment of established tumors, we adoptively transferred CD8 Pmel-1 effector T cells, T cell receptor-transgenic for the melanoma antigen gp-100, into hosts with established B16F10 tumors in their right femur (FIG. 9A). Animals were treated with $15 \times 10^6$ Pmel-1 T lymphocytes, transgenic for Firefly luciferase for in vivo bioluminescent T cell tracking. T cells were either conjugated to nanoparticles tagged with the fluorescent dye DiD (right panels) or left unmodified (left panels). In both treatment groups, we incubated infused T lymphocytes with Thiol-PEG to avoid nonspecific phagocytosis of nanoparticles by macrophages and dendritic cells. Infused T cells of both groups displayed rapid and effective homing to the tumor site, as monitored by bioluminescent T cells imaging on day 4 after T cell transfer (FIG. 9B). Notably, the ex vivo surface conjugation of nanoparticles to T cells, did neither alter their in vivo migration nor did it constrain their potential to recognize tumor antigen. Tumor-homing T cells, furthermore, efficiently aggregated surface-conjugated nanoparticles at the tumor site, as shown by the largely amplified fluorescent DiD signal of the isolated right tumor-infiltrated femur, compared to the left tumor-free femur (FIG. 9C, right panel). Importantly, nanoparticles at the tumor site were still physically linked to tumor-infiltrating T cells, as measured by multicolor flow cytometry of tumor single cell suspensions (FIG. 9D). In essence, we demonstrate that tumor-targeted T lymphocytes effectively shuttle therapeutic nanoparticles to the tumor site. The ex-vivo surface conjugation does not impair T cell viability, migration or tumor recognition and, therefore, offers novel prospect for the targeted biodistribution of nanoparticles and the functional enhancement of tumor-reactive T lymphocytes.

Figure 10A:
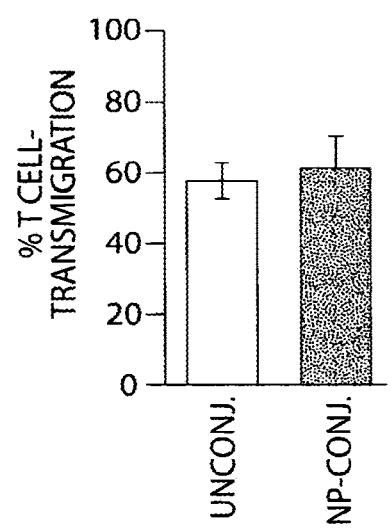
FIGS. 10A-B. Nanoparticle-decorated T cells function normally and efficiently carry surface-tethered nanoparticles into antigen-expressing tumors. OT-1 ova-specific $CD8^+$ effector T cells were conjugated with 100 DNA-gel nanoparticles per cell or left unmanipulated as controls. (A and B) Comparative in vivo bioluminescence (tumors, T cells) and fluorescence imaging (nanoparticles) of mice bearing subcutaneous Gaussia luc-expressing EG7-OVA and control EL4 tumors on opposite flanks, 2 days after i.v. infusion of firefly luc-transgenic $Thy1.1^+$ effector OT-1 T cells (with or without attached DiD-labeled nanoparticles), or an equivalent number of free nanoparticles. $Thy1.1^+$ OT-1 T cells recovered from the EG7-OVA tumors were analyzed for surface-bound DiD nanoparticles by flow cytometry (A), and the mean bioluminescent T cell and fluorescent nanoparticle signals from groups of 6 mice are graphed shown in (B). Shown is 1 of 2 independent experiments.
Figure 10B:
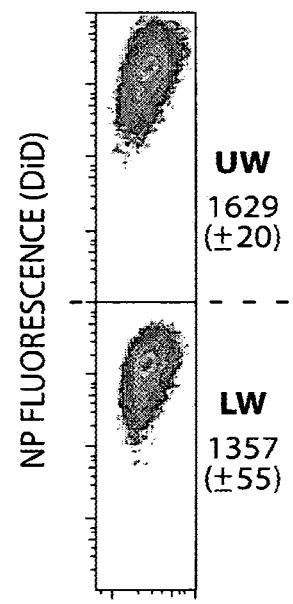

We next evaluated the migratory and tumor-homing properties of nanoparticle-conjugated lymphocytes in an another murine model system. C57Bl/6 mice were injected with EL4 tumor cells expressing membrane-bound Gaussia luciferase (extG-luc) and ovalbumin (EG7-OVA) s.c. on the right flank and control tumors EL4 cells expressing extG-luc alone on the left flank. Tumors were allowed to establish and then mice then received adoptive transfers of Firefly luciferase (F-luc)-transgenic OT-1 T cells with or without surface-conjugated red-fluorescent DNA-gel nanoparticles, or an i.v. injection of an equivalent dose of fluorescent particles alone. Particle-carrying OT-1 T cells specifically trafficked to pre-established EL4-OVA tumors (FIG. 10A). No difference in the tumor homing potential of particle-conjugated compared to plain unmodified OT-1 T cells was observed (FIG. 10B, left panel). Quantitative fluorescent particle imaging of EG7-OVA tumors demonstrated that nanoparticles accumulated a mean 176-fold more efficiently at the tumor site when surface-attached to OT-1 T cells compared to systemically infused free nanoparticles, which were rapidly scavenged by the liver and the spleen (FIG. 10B). Flow cytometry analysis verified that T cell infiltration of EG7-OVA tumors was quantitatively identical for particle-decorated and control OT-1 cells, and that the majority of particle-conjugated cells recovered from tumors still retained their nanoparticle cargo (FIG. 10A).

Figure 11A:
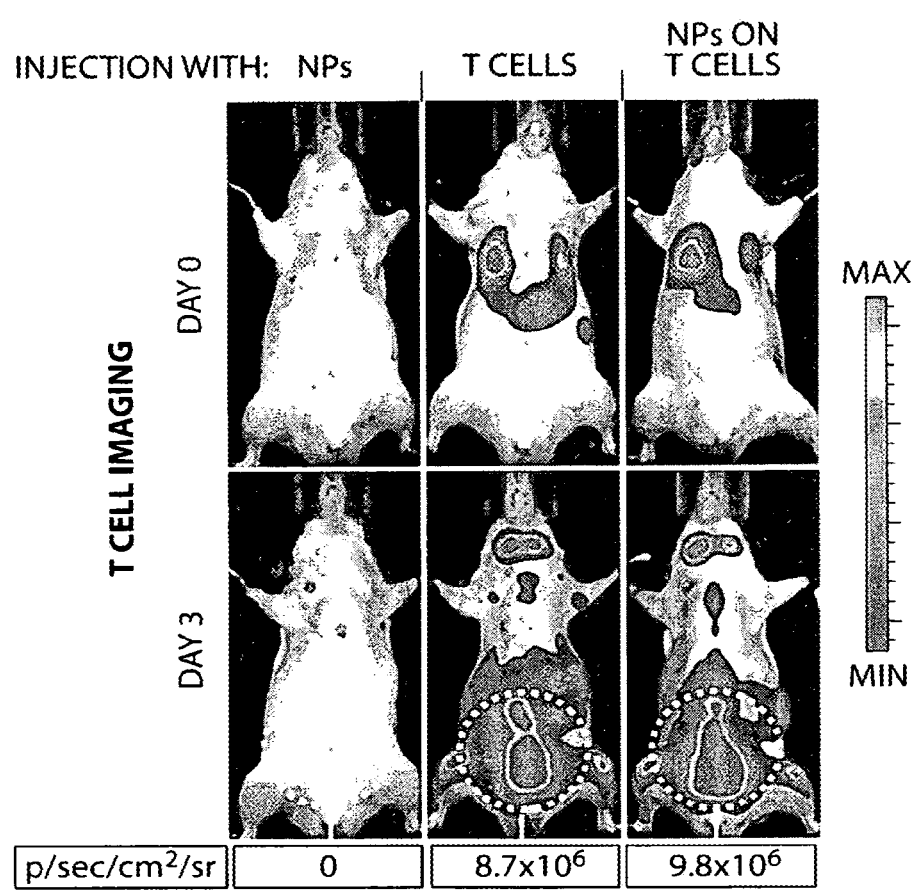
FIGS. 11A-C. Tumor antigen-specific T cells transport surface-bound nanoparticles into established TRAMP prostate adenocarcinomas. (A) Six month-old TRP-SIY mice (Bai et al., PNAS USA, 105:13003, 2008), with established spontaneous prostate adenocarcinomas expressing a short linear peptide SIY (SIYRYYGL; SEQ ID NO:1) were injected with $15 \times 10^6$ CBR-luciferase-expressing SIY-specific 2C transgenic $CD8^+$ T cells. T cells were left unmodified or were surface-conjugated with DiD-tagged DNA-gel nanoparticles. Alternatively, an equivalent number of free DiD-labeled particles was injected intravenously. Ventral whole body bioluminescent acquisitions are shown directly after T cell injection (upper panel), and 3 days later (lower panel). (B) On day 3, prostates were isolated from euthanized mice, and DiD tissue fluorescence was quantified using the IVIS Spectrum imaging system. (C) Flow cytometry analysis of a single cell suspension prepared from recovered prostates shows a substantial fraction of 2C transgenic T cells still physically attached to DiD-labeled DNA-gel nanoparticles.
Figure 11B:
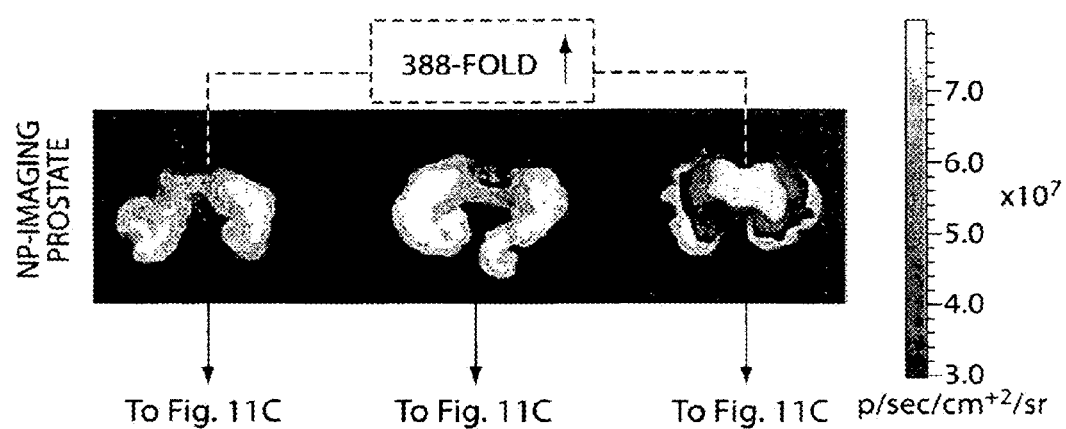
Figure 11C:
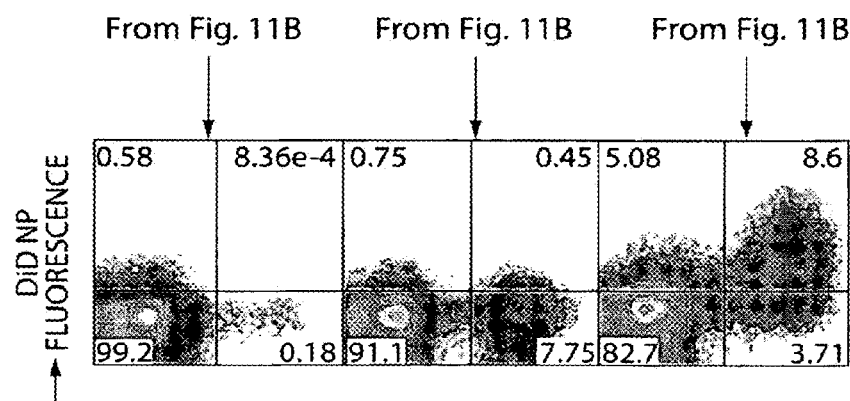

The benefit of tumor-antigen-specific T lymphocytes as cellular vectors for active nanoparticle delivery was also evidenced in a spontaneous prostate cancer model (i.e., the TRAMP prostate adenocarcinoma model). In this model system, prostate tumor-specific T cells loaded with DNA-gel nanoparticles efficiently homed to antigen-expressing hyperplastic TRAMP prostates and aggregated surface-linked fluorescent particles at the tumor site, whereas no fluorescent nanoparticle signal above background was detected in the prostate following systemic injection of an equivalent particle dose (FIG. 11A-C).

Figure 12A:
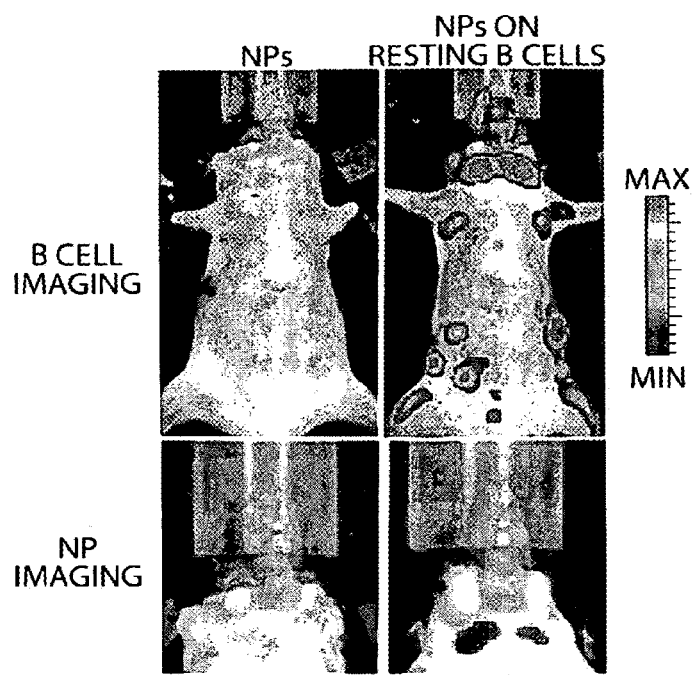
FIGS. 12A-F. Naïve B lymphocytes transport surface-conjugated nanoparticles into secondary lymphoid organs. (A) Comparative in vivo bioluminescence (upper panel) and fluorescence (lower panel) imaging of C57Bl/6 mice 2 days after infusion of $10 \times 10^6$ Firefly-luciferase-transgenic naïve B lymphocytes, labeled with CellTracker Green and decorated with DiD fluorescent DNA gel nanoparticles. Alternatively, mice were systemically injected with an equivalent number of free DiD nanoparticles only. One representative mouse out of 3 injected mice/group is shown. (B) Strong DiD tissue fluorescence was detected in isolated cervical lymph nodes by IVIS imaging. (C) Histology of the removed cervical lymph node. High-magnification confocal microscopy (left panel) shows lymph node homing B lymphocytes with surface-attached DiD-fluorescent nanoparticles. (D) Biodistribution analysis of B cells carrying Indium-loaded liposomes and empty liposomes. (E) Histology section showing B cells that have homed into lymph nodes still have nanoparticles (blue) attached to their surfaces. (F) Eµ-myc lymphoma cells were injected into mice and allowed to establish tumors in systemic lymphoid organs for 14 days prior to injection of particle-carrying normal B cells. Flow cytometry shows the liposome-carrying B cells have entered the lymph nodes.
Figure 12B:
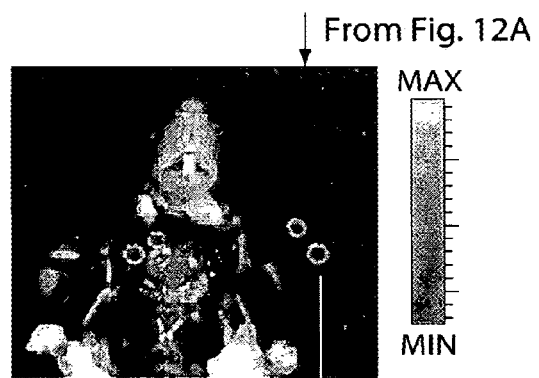
Figure 12C:
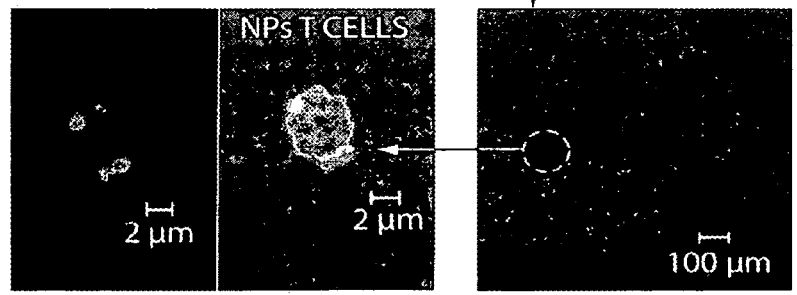
Figure 12D:
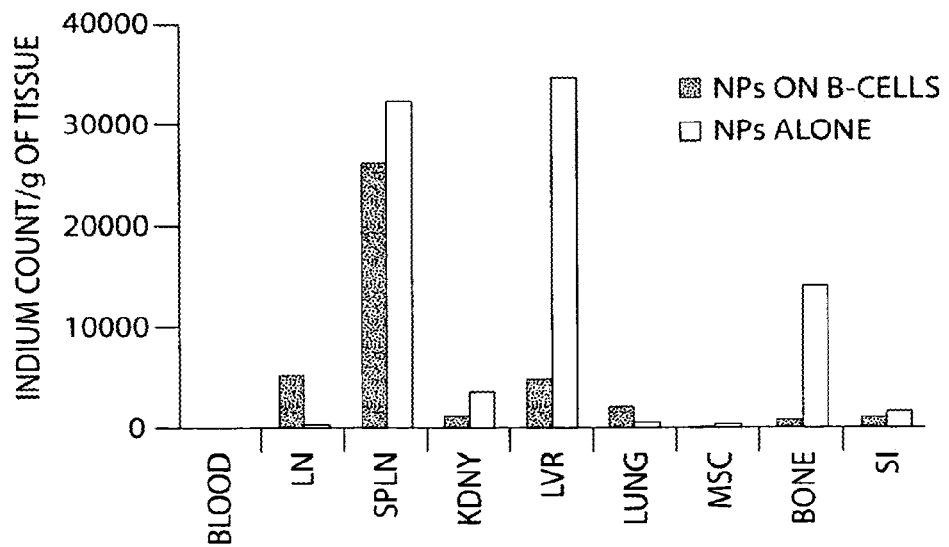
Figure 12E:
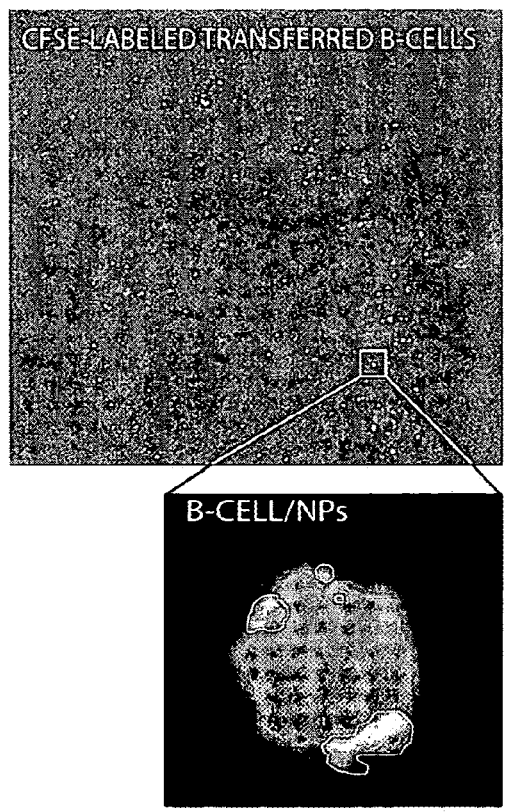
Figure 12F:
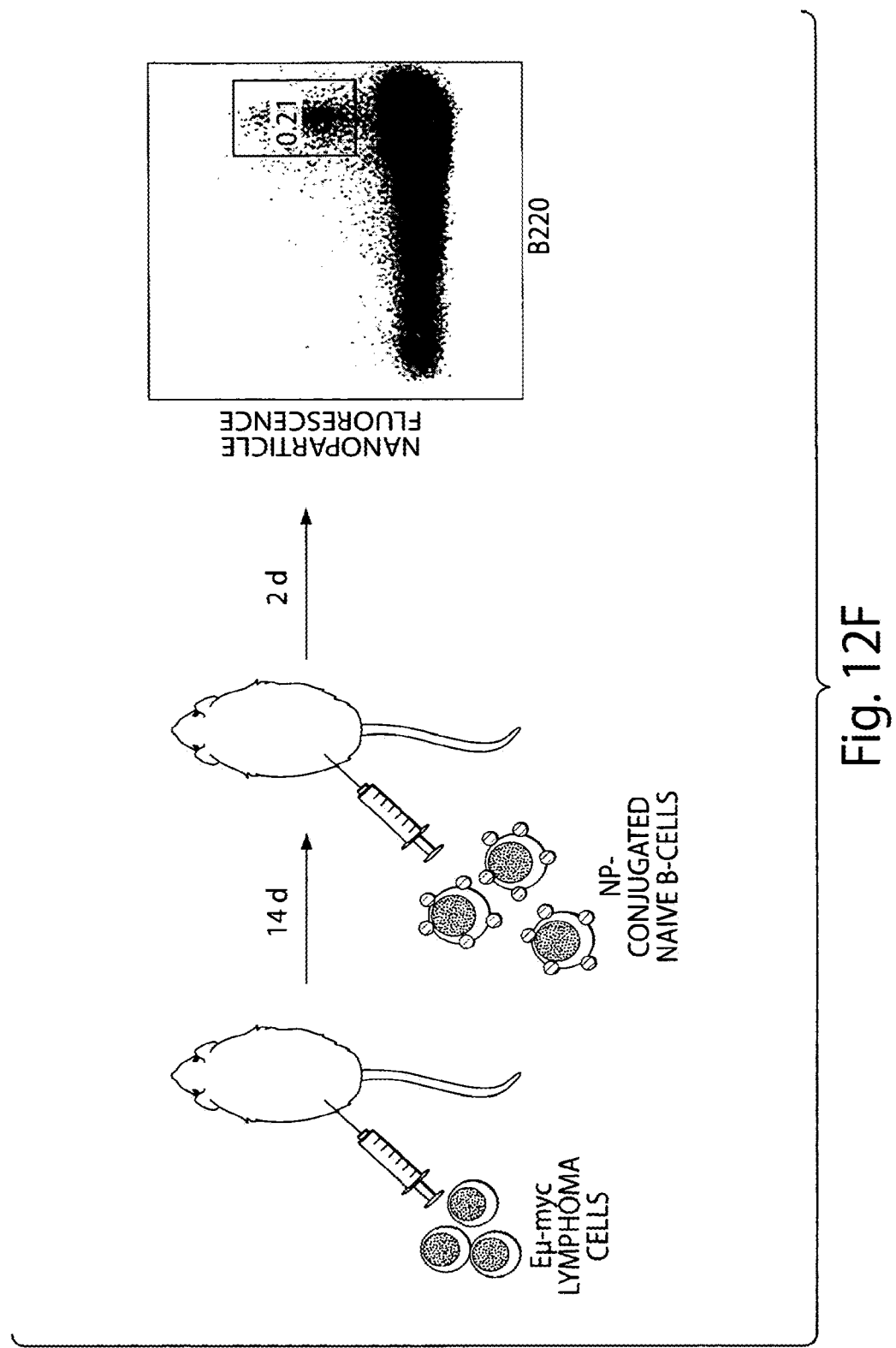

The ability of lymphocytes to efficiently transfer surface-tethered nanoparticles across endothelial barriers in vivo was not restricted to the abnormal, leaky and discontinuous endothelial lining found in tumor vasculature. When DNA-gel particles were linked to resting $CCR7^+CD62L^+$ B cells (FIGS. 12A-C) or central memory $CD8^+$ T cells (data not shown), particles were transported across the intercellular boundaries of high endothelial venules into lymph nodes, a poorly accessible compartment for systemically infused free nanoparticles. FIGS. 12D-F show the biodistribution profile of nanoparticles conjugated to B cells versus free nanoparticles, the presence of nanoparticles on B cells harvested from subjects, and the localization of administered B cells and conjugated nanoparticles to lymph nodes.

In the studies above, nanoparticles without therapeutic cargo were appended to cells possessing a defined tissue tropism to demonstrate the utility of therapeutic cells as highly efficient vectors for nanoparticle delivery to otherwise difficult-to-access anatomical compartments.

Figure 13C:
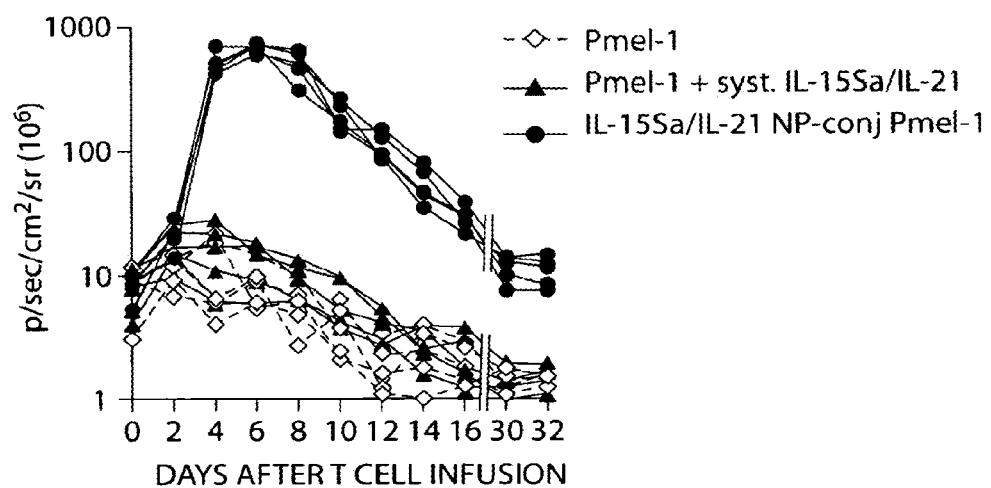
Figure 13D:
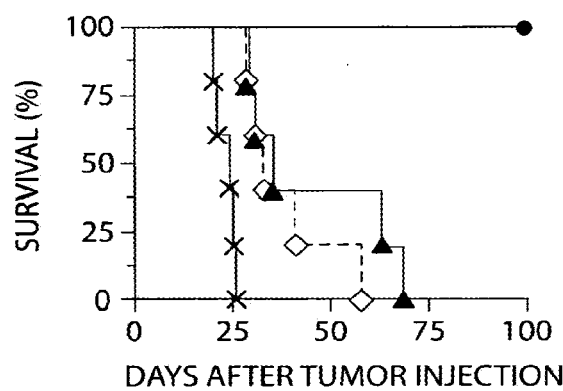

We next tested whether cell-bound drug-loaded nanoparticles could directly impart amplified therapeutic functions to their cellular carriers, using a murine model of adoptive T cell therapy for melanoma (Overwijk et al., J Exp Med, 188:277, 1998). We encapsulated a mixture of IL-15, (converted to a superagonist (IL-15Sa) by pre-complexing with soluble IL-15Rα (Rubinstein et al., PNAS USA, 103:9166, 2006)), in combination with IL-21 into lipid-coated DNA-gel particles. IL-15 and IL-21 are known to cooperatively promote in vivo T cell expansion and effector function when administered daily at high doses. DNA-gel particles ~200 nm in diameter efficiently entrapped the IL-15Sa/IL-21 cytokine mixture and displayed slow release kinetics over a 7-day period (data not shown). These cytokine-loaded particles were conjugated to Click bettle red (CBR)-luciferase expressing CD8$^+$ Pmel-1 effector T cells which recognize a peptide from the melanocyte differentiation antigen gp100. Particle-conjugated or control T cells were infused into lympho-depleted mice bearing established Gaussia luciferase-expressing B16F10 melanoma lung tumors (FIG. 13A). Serial imaging of non-conjugated Pmel-1 T cells showed a gradual CBR-luc signal decline following T cell injection, consistent with poor in vivo T cell expansion and persistence (FIGS. 13B and C). Whereas a single systemic infusion of 5 μg free IL-15Sa/IL-21 (4.03 μg IL-15Sa+0.93 μg IL-21) given on the day of adoptive transfer did not significantly boost Pmel-1 proliferation (1.4-fold-higher CBR-luc signal on day 6, P=0.32), the same cytokine dose loaded in surface-attached nanoparticles conferred markedly amplified proliferative capabilities on Pmel-1 T cells (81-fold higher peak photon count relative to unmodified Pmel-1 T cells on day 6, P<0.0001, FIGS. 13A and C). Subsequent to a contraction period, IL-15Sa/IL-21 nanoparticle-carrying T cells displayed enhanced long-term persistence (14.8-fold and 4.7-fold higher photon count than Pmel-1 T cells alone at 16 and 30 days after T cell infusion, respectively, P<0.0001) and homed as CD44$^+$CD62L$^+$ central memory T cells to lymph nodes and spleen (FIGS. 13A and B, and data not shown). There was no evidence of progressive T cell clonality or leukemia formation in any treated animal imaged at late time points (data not shown). Pmel-1 T cells conjugated with "empty" nanoparticles exhibited the same expansion/decline in vivo as unmodified Pmel-1 cells (data not shown). All mice receiving IL-15Sa/IL-21 nanoparticle-decorated Pmel-1 T cells achieved complete tumor clearance (FIGS. 13A and D), whereas treatment with Pmel-1 T cells with or without systemic IL-15Sa/IL-21 infusion at the same doses yielded only modest survival advantages (FIG. 13D).

Example 5

Conjugation of Nanoparticles to Hematopoietic Progenitor Cells

We further examined the utility of this delivery approach in the context of hematopoietic stem cell transplantations. We treated C57Bl/6 F-luc-transgenic mice or C57Bl/6 GFP-transgenic mice with 5-fluorouracil (5-FU, Sigma Aldrich) (150 mg/kg, i.p) and euthanized them 3 days later. Bone marrow cells were removed aseptically from femurs and tibias. Bone marrow was pre-enriched for progenitor cells using a lineage depletion kit (Miltenyi). A subsequent positive selection with anti-Sca-1 microbeads (Miltenyi) resulted in an average 92% purity of lin$^-$Sca-1$^+$c-kit$^+$ HSCs. Cells were kept in serum-free StemSpan (Stem Cell Technologies) for 3 hours before further modification.

1×10$^4$ unmodified or nanoparticle-decorated HSCs were transplanted by retroorbital injection into lethally irradiated (1300 cGy of total body irradiation from a $^{137}$Cs source as a split dose with 3-hr interval between) nontransgenic recipients.

For in vitro HSC expansion, HSCs, retrovirally transduced with NUP98-HOXA10hd, were cultured in DMEM supplemented with 15% FBS and cytokines (6 ng/mL of IL-3, 10 ng/mL of IL-6, 100 ng/mL of SCF, all Preprotech).

Figure 14A:
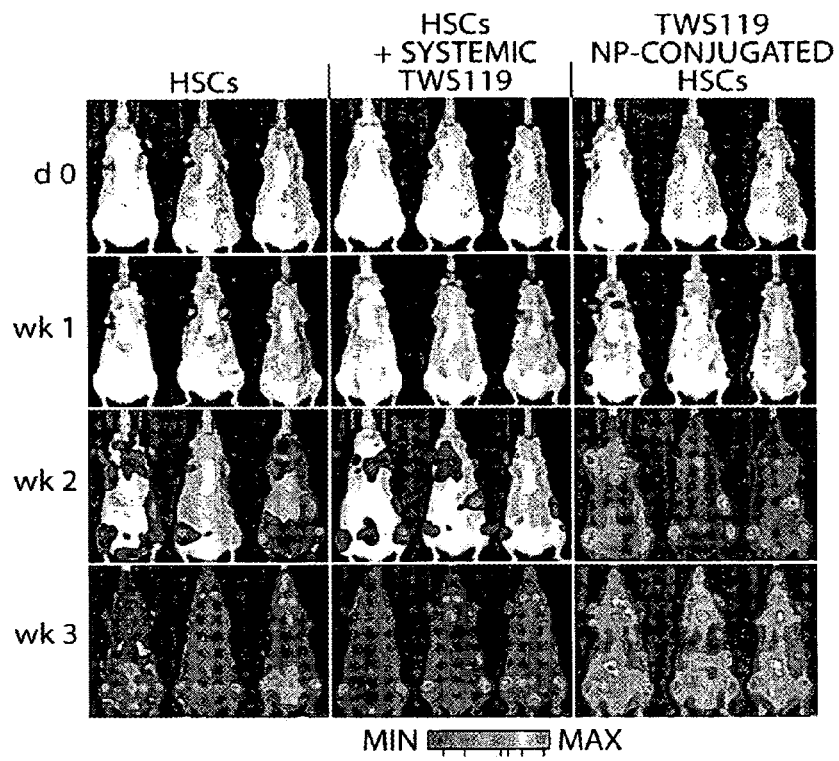
FIGS. 14A-D. Hematopoietic progenitor cells (referred to in the Figure as HSCs) carrying GSK-3β inhibitor-loaded nanoparticles reconstitute recipient animals with rapid kinetics following bone marrow transplants without affecting multilineage differentiation potential. (A, B) Engraftment kinetics of luciferase-transgenic HSC grafts in lethally-irradiated nontransgenic syngeneic recipients. Mice were treated with a single bolus injection of the GSK-3β inhibitor TWS119 (1.6 ng) on the day of transplantation, an equivalent TWS119 dose encapsulated in HSC-attached DNA-gel nanoparticles, or no exogenous agent. Transplanted mice were imaged for whole-body bioluminescence every 7 days for 3 weeks. Shown are representative IVIS images (A) and whole animal photon counts (B) for 9 mice total/treatment condition. (C) Percentage of donor-derived cells in recipient mice 2 weeks after transplantation of GFP+ HSCs with or without TWS119. *P<0.001. (D) Average frequency of donor-derived GFP+ B cells, T cells, and myeloid cells in recipient mice 3 months after transplantation. 5 mice/group were analyzed.
Figure 14B:
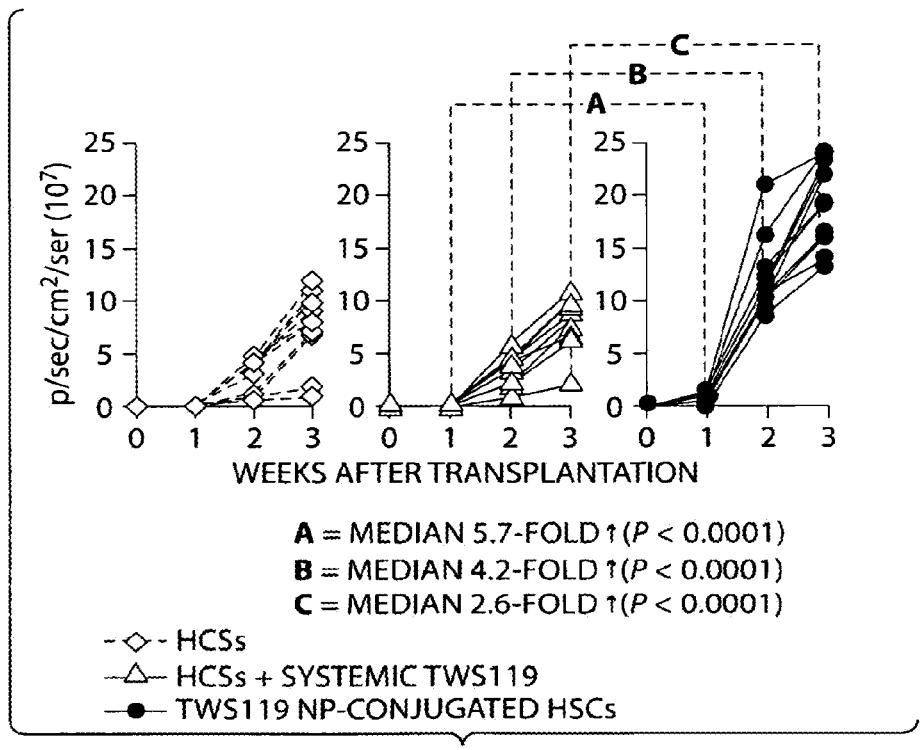
Figure 14C:
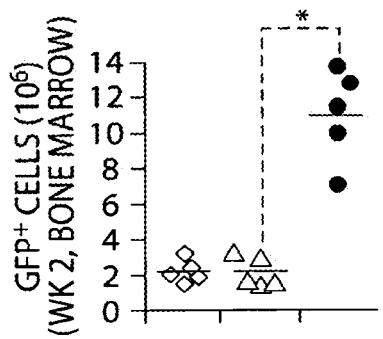
Figure 14D:
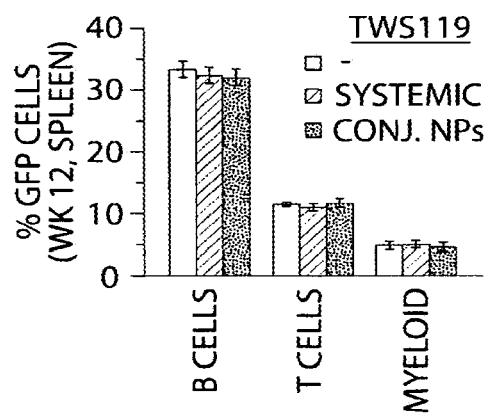

We chose the glycogen synthase kinase-3β (GSK-3β) inhibitor TWS119 (Gattinoni et al., Nat Med 15:808, 2009) as therapeutic cargo, based on reports that repeated high-dose bolus therapy of transplant recipients with glycogen synthase kinase-3 (GSK-3) inhibitors enhances the repopulation kinetics of donor HSCs (Trowbridge et al., Nat Med 12:89, 2006). DNA-gel nanoparticles efficiently encapsulated this small-molecule drug, and slowly released it over a 7-day time window (data not shown). We evaluated the in vivo repopulation capabilities of hematopoietic grafts supported by cell-bound TWS119-loaded nanoparticles based on the whole body photon emission from Firefly luciferase-transgenic donor progenitor cells, and in separate experiments, by tracing the frequencies of GFP$^+$ donor progenitor cells by flow cytometry. Following transplantation of murine lineage$^-$Sca-1$^+$c-kit$^+$ progenitor cells from luciferase-transgenic donors into syngeneic recipients, a steady increase in whole body bioluminescent emission was observed originating from discrete foci over anatomical sites corresponding to the femurs, humeri, sternum and the spleen (FIG. 14A). While a systemic TWS119 bolus injection (1.6 ng) at the time of transplantation did not significantly alter measured engraftment kinetics (FIGS. 14A and B), the same TWS119 dose encapsulated in nanoparticles surface-tethered to donor progenitor cells markedly enhanced the proliferative reconstitution of progenitor cell grafts (median 5.7-fold higher bioluminescence than systemic TWS119 after 1 week, P<0.0001, FIGS. 14A-C). Notably, animals in all treatment groups initially engrafted progenitor cells in both femurs and the sternum, indicating that nanoparticle conjugation did not compromise the intrinsic homing properties of donor progenitor cells. While increasing the rate of initial reconstitution, conjugating TWS119 nanoparticles onto progenitor cells did not affect their multilineage differentiation potential, reflected by a similar frequency of donor-derived GFP$^+$ reconstituted cell types compared to control progenitor cell grafts three months after transplantation (FIG. 14D). Thus, this simple approach for donor cell modification just prior to cell transfer can also augment hematopoietic progenitor cell, including hematopoietic stem cell, transplants, a procedure in routine clinical practice.

Example 6

Conjugation of Liposomes to Cells

One exemplary protocol for synthesizing unilamellar liposomes is as follows: A DOPC/DOPG/MPB PE/DiD lipid film (lipid ratios as in polymer nanoparticles) was hydrated with 185 μl PBS for a one-hour period with vigorous vortexing every 10 minutes. After six cycles of freezing (liquid N$_2$) and thawing, the liposomes were extruded 21 times through a polycarbonate filter (200 nm pore size, Whatman) and purified using a Zeba Spin Desalting Column (Thermo Scientific)

Figure 15:
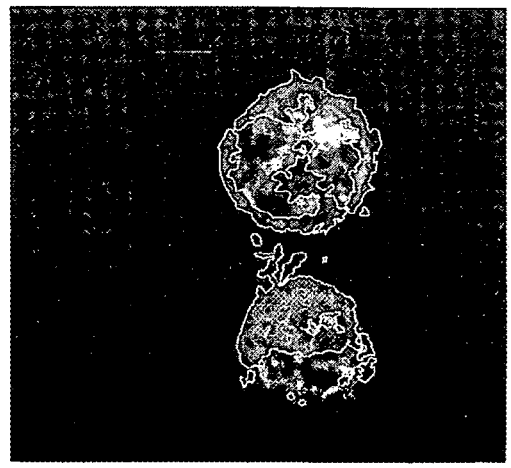
FIG. 15. Liposome conjugation to pmel-1 T cells. Confocal image of liposomes (blue) conjugated to the surfaces of pmel-1 T cells (CFSE-stained in green). Shown are 3D projections of optical sections taken by confocal microscopy.

FIG. 15 shows liposome conjugation to pmel-1 T cells. The confocal image shows liposomes (blue) conjugated to the surfaces of pmel-1 T cells (CFSE-stained in green). Shown are 3D projections of optical sections taken by confocal microscopy.

REFERENCES

1. Rosenberg S A et al., Nat Rev Cancer 8(4): 299, 2008.
2. Dudley M E et al., Science 298(5594): 850, 2002.

3. June C H et al., *J Clin Invest* 117(5): 1204, 2007.
4. Stephan M T et al., *Nat Med* 13(12): 1440, 2007.
5. Yee C et al., *Proc Natl Acad Sci USA* 99(25): 16168, 2002.
6. Morgan R A et al., *Science* 314(5796): 126, 2006.
7. Gade T P et al., *Cancer Res* 65(19): 9080, 2005.
8. Anderson M J et al., *J Immunol* 178(3): 1268, 2007.
9. Janicki C N et al., *Cancer Res* 68(8): 2993, 2008.
10. Antony P A et al., *J Immunol* 176(9): 5255, 2006.
11. Fontenot J D et al., *Nat Immunol* 6(11): 1142, 2005.
12. Oh S et al., *Proc Natl Acad Sci USA* 100(6): 3392, 2003.
13. Waldmann T A, *Nat Rev Immunol* 6(8): 595, 2006.
14. Waldmann T A et al., *Immunity* 14(2): 105, 2001.
15. Dubois S et al., *Immunity* 17(5): 537, 2002.
16. Stoklasek T A et al., *J Immunol* 177(9): 6072, 2006.
17. Klebanoff C A et al., *Proc Natl Acad Sci USA* 101(7): 1969, 2004.
18. Teague R M et al., *Nat Med* 12(3): 335, 2006.
19. Dubois S et al., *J Immunol* 180(4): 2099, 2008.
20. Rubinstein M P et. al. *Proc Nail Acad Sci USA* 103(24): 9166, 2006.
21. Epardaud M et al., *Cancer Res* 68(8): 2972, 2008.
22. Beutler B, *Nature* 430(6996): 257, 2004.
23. Iwasaki A et al., *Nat Immunol* 5(10): 987, 2004.
24. Pulendran B, *Immunol Rev* 199: 227, 2004.
25. Reis e Sousa C, *Semin Immunol* 16(1): 27, 2004.
26. Pasare C et al., *Science* 299(5609): 1033, 2003.
27. Yang Y et al., *Nat Immunol* 5(5): 508, 2004.
28. Overwijk W W et al., *J Exp Med* 198(4): 569, 2003.
29. Heckelsmiller K et al., *Eur J Immunol* 32(11): 3235, 2002.
30. Furumoto K et al., *J Clin Invest* 113(5): 774, 2004.
31. Currie A J et al., *J Immunol* 180(3): 1535, 2008.
32. Vicari A P et al., *J Exp Med* 196(4): 541, 2002.
33. Mata-Haro V et al., *Science* 316(5831): 1628, 2007.
34. Paulos C M et al., *Clin Cancer Res* 13(18 Pt 1): 5280, 2007.
35. Paulos C M et al., *J Clin Invest* 117(8): 2197, 2007.
36. Hemmi H et al., *Nat Immunol* 3(2): 196, 2002.
37. Stary G et al., *J Exp Med* 204(6): 1441, 2007.
38. Goldstein D et al., *J Infect Dis* 178(3): 858, 1998.
39. Soria I et al., *Int J Clin Pharmacol Ther* 38(10): 476, 2000.
40. Fan J et al., *J Clin Invest* 112(8): 1234, 2003.
41. Gunzer M et al., *Blood* 106(7): 2424, 2005.
42. Greenland J R et al., immunization. *Mol Ther* 12(1): 164, 2005.
43. Hu Y et al., *Nano Lett* 7(10): 3056, 2007.
44. Verma A et al., *Nat Mater* 7(7): 588, 2008.
45. Zhao X et al., *Biomaterials* 26(24): 5048, 2005.
46. Bershteyn A et al., *Soft Matter* 4: 1787, 2008.
47. Davis M E et al., *Nat Rev Drug Discov* 7(9): 771, 2008.
48. Green J J et al., *Advanced Materials* 19(19): 2836, 2007.
49. Donsante A et al., *Science* 317(5837): 477, 2007.
50. Kresge K J, *IAVI Rep* 9(4): 18, 2005.
51. Mingozzi F et al., *Nat Med* 13(4): 419, 2007.
52. Watkins D I et al., *Nat Med* 14(6): 617, 2008.
53. Maeda H et al., *J Control Release* 65(1-2): 271, 2000.
54. Matsumura Y et al., *Cancer Res* 46(12 Pt 1): 6387, 1986.
55. Shi X Y et al., *Advanced Materials* 20(9): 1671, 2008.
56. von Maltzahn G et al., *Bioconjugate Chemistry* 19(8): 1570, 2008.
57. Drummond D C et al., *Pharmacol Rev* 51(4): 691, 1999.
58. Kirpotin D B et al., *Cancer Res* 66(13): 6732, 2006.
59. Park J W et al., *Clin Cancer Res* 8(4): 1172, 2002.
60. Owens D E, *Int J Pharm* 307(1): 93, 2006.
61. Vonarbourg A et al., *Biomaterials* 27(24): 4356, 2006.
62. Moghimi S M et al., *Pharmacol Rev* 53(2): 283, 2001.
63. Dou H et al., *Blood* 108(8): 2827, 2006.
64. Cole C et al., *Nat Med* 11(10): 1073, 2005.
65. Qiao J et al., *Nat Med* 14(1): 37, 2008.
66. Monine M I et al., *Biophys J* 88(4): 2384, 2005.
67. Lauffenburger D A et al., *Proc Natl Acad Sci USA* 95(26): 15368, 1998.
68. Joslin E J et al., *J Cell Sci* 120(Pt 20): 3688, 2007.
69. Klebanoff C A et al., *Proc Natl Acad Sci USA* 102(27): 9571, 2005.
70. Overwijk W W et al., *J Exp Med* 188(2): 277, 1998.
71. Sahaf B et al., *Proc Natl Acad Sci USA* 100(7): 4001, 2003.
72. Stachowiak A N et al., *J Immunol* 177(4): 2340, 2006.
73. Chacon M et al., *Int J Pharmaceutics* 141(1-2): 81, 1996.
74. Diwan M et al., *Curr Drug Deliv* 1(4): 405, 2004.
75. Elamanchili P et al., *Vaccine* 22(19): 2406, 2004.
76. Li Y et al., *J Control Release* 71(2): 203, 2001.
77. Zhang Z P et al., *Biomaterials* 28(10): 1889, 2007.
78. Heit A et al., *Eur J Immunol* 37(8): 2063, 2007.
79. Hamann A et al., *Eur J Immunol* 30(11): 3207, 2000.

EQUIVALANTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for maintaining, stimulating or enhancing activity of a T cell, comprising administering to a subject a T cell that homes to a tumor and is covalently bound to a liposome that comprises an immunostimulatory cytokine that maintains, stimulates or enhances activity of a T cell, wherein the T cell does not significantly internalize the liposome and maintains the liposome on the cell surface, and wherein release of the immunostimulatory cytokine from the liposome maintains, stimulates or enhances activity of the T cell relative to an unmodified T cell.

2. The method of claim 1, wherein the liposome is 20-500 nm in diameter.

3. The method of claim 1, wherein the liposome comprises maleimide reactive groups on its surface.

4. The method of claim 1, wherein the cytokine is IL-15/IL-15Rα.

5. The method of claim 1, wherein the cytokine is IL-2.

6. The method of claim 1, wherein the T cell is a tumor-reactive T cell.

7. The method of claim 1, wherein the T cell is covalently bound to a plurality of liposomes.

8. The method of claim 1, wherein release of the immunostimulatory cytokine enhances survival of the T cell.

9. The method of claim 1, wherein release of the immunostimulatory cytokine enhances proliferation of the T cell.

10. The method of claim 1, wherein covalent binding of the liposome to the T cell does not inhibit cytokine production of the T cell.

11. The method of claim 1, wherein covalent binding of the liposome to the T cell does not inhibit cytolytic activity of the T cell.

12. A method for maintaining, stimulating or enhancing activity of a T cell located in the environment of a tumor, comprising administering to a subject having a tumor a carrier T cell that homes to the tumor and is covalently bound to a liposome that comprises an immunostimulatory cytokine that maintains, stimulates or enhances activity of a T cell, wherein the carrier T cell does not significantly internalize the liposome and maintains the liposome on the cell surface, and wherein release of the immunostimulatory cytokine from the liposome maintains, stimulates or enhances activity of a T cell located in the environment of the tumor.

13. The method of claim 12, wherein the liposome is biodegradable.

14. The method of claim 12, wherein the liposome is 20-500 nm in diameter.

15. The method of claim 12, wherein the liposome comprises maleimide reactive groups on its surface.

16. The method of claim 12, wherein the T cell is a tumor-reactive T cell.

17. The method of claim 12, wherein the T cell is covalently bound to a plurality of liposomes.

18. The method of claim 12, wherein the cytokine is IL-15/IL-15Rα.

19. The method of claim 12, wherein the cytokine is IL-2.

20. The method of claim 12, wherein release of the immunostimulatory cytokine enhances survival of the T cell.

21. The method of claim 12, wherein release of the immunostimulatory cytokine enhances proliferation of the T cell.

22. The method of claim 12, wherein covalent binding of the liposome to the T cell does not inhibit cytokine production of the T cell.

23. The method of claim 12, wherein covalent binding of the liposome to the T cell does not inhibit cytolytic activity of the T cell.

24. A composition comprising a T cell that homes to a tumor and is covalently bound to a liposome that comprises an immunostimulatory cytokine that maintains, stimulates or enhances activity of a T cell, wherein the T cell does not significantly internalize the liposome and maintains the liposome on the cell surface, and wherein release of the immunostimulatory cytokine from the biodegradable liposome maintains, stimulates or enhances activity of the T cell relative to an unmodified T cell.

25. The composition of claim 24, wherein the cytokine is IL-15/IL-15Rα.

26. The composition of claim 24, wherein the cytokine is IL-2.

27. The composition of claim 24, wherein the liposome is biodegradable.

28. The composition of claim 24, wherein the liposome is 20-500 nm in diameter.

29. The composition of claim 24, wherein the liposome comprises maleimide reactive groups on its surface.

30. The composition of claim 24, wherein the T cell is a tumor-reactive T cell.

31. The composition of claim 24, wherein the T cell is covalently bound to a plurality of liposomes.

32. The composition of claim 24, wherein covalent binding of the liposome to the T cell does not inhibit cytokine production of the T cell.

33. The composition of claim 24, wherein covalent binding of the liposome to the T cell does not inhibit cytolytic activity of the T cell.

34. A method of maintaining, stimulating or enhancing activity of a T cell, comprising administering to a subject a population of T cells that home to a tumor and are covalently bound to a plurality of liposomes that comprise an immunostimulatory cytokine that maintains, stimulates or enhances activity of a T cell, wherein the T cells do not significantly internalize the liposomes and maintain the liposomes on the cell surface, and wherein release of the immunostimulatory cytokine from the liposomes maintains, stimulates or enhances activity of the T cells relative to unmodified T cells.

35. The method of claim 34, wherein the liposomes are biodegradable.

36. The method of claim 34, wherein the liposomes are 20-500 nm in diameter.

37. The method of claim 34, wherein the liposomes comprise maleimide reactive groups on their surface.

38. The method of claim 34, wherein the T cells are tumor-reactive T cells.

39. The method of claim 34, wherein the cytokine is IL-15/IL-15Rα.

40. The method of claim 34, wherein the cytokine is IL-2.

41. A method of maintaining, stimulating or enhancing activity of a T cell located in the environment of a tumor, comprising administering to a subject having a tumor a population of carrier T cells that home to a tumor and are covalently bound to a plurality of liposomes that comprise an immunostimulatory cytokine that maintains, stimulates or enhances activity of a T cell, wherein the carrier T cells do not significantly internalize the liposomes and maintain the liposomes on the cell surface, and wherein release of the immunostimulatory cytokine from the liposomes maintains, stimulates or enhances activity of T cells located in the environment of the tumor.

42. The method of claim 41, wherein the liposomes are biodegradable.

43. The method of claim 41, wherein the liposomes are 20-500 nm in diameter.

44. The method of claim 41, wherein the liposomes comprise maleimide reactive groups on their surface.

45. The method of claim 41, wherein the T cells are tumor-reactive T cells.

46. The method of claim 41, wherein the cytokine is IL-15/IL-15Rα.

47. The method of claim 41, wherein the cytokine is IL-2.

48. A composition comprising a population of T cells that home to a tumor and are covalently bound to a plurality of liposomes that comprise an immunostimulatory cytokine that maintains, stimulates or enhances activity of a T cell, wherein the T cells do not significantly internalize the liposomes and maintain the liposomes on the cell surface, and wherein release of the immunostimulatory cytokine from the liposomes maintains, stimulates or enhances activity of the T cells relative to unmodified T cells.

49. The composition of claim 48, wherein the liposomes are biodegradable.

50. The composition of claim 48, wherein the liposomes are 20-500 nm in diameter.

51. The composition of claim 48, wherein the liposomes comprise maleimide reactive groups on their surface.

52. The composition of claim 48, wherein the T cells are tumor-reactive T cells.

53. The composition of claim 48, wherein the cytokine is IL-15/IL-15Rα.

54. The composition of claim 48, wherein the cytokine is IL-2.

55. A composition comprising a population of carrier T cells that home to a tumor and are covalently bound to a plurality of liposomes that comprise an immunostimulatory cytokine that maintains, stimulates or enhances activity of a T cell, wherein the carrier T cells do not significantly internalize the liposomes and maintain the liposomes on the cell surface, and wherein release of the immunostimulatory cytokine from the liposomes maintains, stimulates or enhances activity of T cells located in the environment of a tumor.

56. The composition of claim 55, wherein the liposomes are biodegradable.

57. The composition of claim 55, wherein the liposomes are 20-500 nm in diameter.

58. The composition of claim 55, wherein the liposomes comprise maleimide reactive groups on their surface.

59. The composition of claim 55, wherein the T cells are tumor-reactive T cells.

60. The composition of claim 55, wherein the cytokine is IL-15/IL-15Rα.

61. The composition of claim 55, wherein the cytokine is IL-2.

62. A composition comprising a population of carrier T cells that home to a tumor and are covalently bound to a plurality of liposomes that comprise IL-15, wherein the carrier T cells do not significantly internalize the liposomes and maintain the liposomes on the cell surface, and wherein release of the IL-15 from the liposomes maintains, stimulates or enhances activity of the carrier T cells, or maintains, stimulates or enhances activity of T cells located in the environment of a tumor, or both.

63. The composition of claim 62, wherein the liposomes are biodegradable.

64. The composition of claim 62, wherein the liposomes are 20-500 nm in diameter.

65. The composition of claim 62, wherein the liposomes comprise maleimide reactive groups on their surface.

66. The composition of claim 62, wherein the T cells are tumor-reactive T cells.

* * * * *

SEQUENCE LISTING

```
<160> NUMBER OF SEQ ID NOS: 5

<210> SEQ ID NO 1
<211> LENGTH: 8
<212> TYPE: PRT
<213> ORGANISM: artificial sequence
<220> FEATURE:
<223> OTHER INFORMATION: synthetic peptide

<400> SEQUENCE: 1

Ser Ile Tyr Arg Tyr Tyr Gly Leu
1               5

<210> SEQ ID NO 2
<211> LENGTH: 40
<212> TYPE: DNA
<213> ORGANISM: artificial sequence
<220> FEATURE:
<223> OTHER INFORMATION: synthetic nucleic acid

<400> SEQUENCE: 2
acgtcgaccg atgaatagcg gtcagatccg tacctactcg                           40

<210> SEQ ID NO 3
<211> LENGTH: 40
<212> TYPE: DNA
<213> ORGANISM: artificial sequence
<220> FEATURE:
<223> OTHER INFORMATION: synthetic nucleic acid

<400> SEQUENCE: 3
acgtcgagta ggtacggatc tgcgtattgc gaacgactcg                           40
```

```
<210> SEQ ID NO 4
<211> LENGTH: 40
<212> TYPE: DNA
<213> ORGANISM: artificial sequence
<220> FEATURE:
<223> OTHER INFORMATION: synthetic nucleic acid

<400> SEQUENCE: 4
acgtcgagtc gttcgcaata cggctgtacg tatggtctcg                40

<210> SEQ ID NO 5
<211> LENGTH: 40
<212> TYPE: DNA
<213> ORGANISM: artificial sequence
<220> FEATURE:
<223> OTHER INFORMATION: synthetic nucleic acid

<400> SEQUENCE: 5
acgtcgagac catacgtaca gcaccgctat tcatcggtcg                40
```